(12) United States Patent
Fernandez et al.

(10) Patent No.: US 10,835,592 B2
(45) Date of Patent: *Nov. 17, 2020

(54) BIOCONJUGATES MADE FROM RECOMBINANT N-GLYCOSYLATED PROTEINS FROM PROCARYOTIC CELLS

(71) Applicant: GLAXOSMITHKLINE BIOLOGICALS S.A., Rixensart (BE)

(72) Inventors: Fabiana Fernandez, Unterengstringen (CH); Michael Wetter, Zurich (CH); Michael Kowarik, Zurich (CH); Michael Wacker, Unterengstringen (CH)

(73) Assignee: GlaxoSmithKline Biologicals SA, Rixensart (BE)

(*) Notice: Subject to any disclaimer, the term of this patent is extended or adjusted under 35 U.S.C. 154(b) by 0 days.

This patent is subject to a terminal disclaimer.

(21) Appl. No.: 14/522,254

(22) Filed: Oct. 23, 2014

(65) Prior Publication Data

US 2015/0044254 A1 Feb. 12, 2015

Related U.S. Application Data

(63) Continuation of application No. 12/735,773, filed as application No. PCT/IB2009/000287 on Feb. 19, 2009, now Pat. No. 8,895,014.

(60) Provisional application No. 61/064,163, filed on Feb. 20, 2008, provisional application No. 61/071,545, filed on May 5, 2008, provisional application No. 61/129,480, filed on Jun. 30, 2008, provisional application No. 61/129,852, filed on Jul. 24, 2008, provisional application No. 61/136,687, filed on Sep. 25, 2008.

(51) Int. Cl.
| | | |
|---|---|---|
| *A61K 39/00* | (2006.01) | |
| *A61K 39/385* | (2006.01) | |
| *A61K 39/116* | (2006.01) | |
| *A61K 39/02* | (2006.01) | |
| *C12P 21/06* | (2006.01) | |
| *C12N 15/09* | (2006.01) | |
| *A61K 39/112* | (2006.01) | |
| *A61K 39/108* | (2006.01) | |
| *A61K 39/104* | (2006.01) | |
| *C07K 14/195* | (2006.01) | |

(52) U.S. Cl.
CPC ...... *A61K 39/0283* (2013.01); *A61K 39/0258* (2013.01); *A61K 39/104* (2013.01); *A61K 39/105* (2013.01); *A61K 39/385* (2013.01); *C07K 14/195* (2013.01); *A61K 2039/6037* (2013.01); *A61K 2039/6068* (2013.01); *A61K 2039/6087* (2013.01); *C07K 2319/034* (2013.01); *Y02A 50/47* (2018.01); *Y02A 50/474* (2018.01); *Y02A 50/476* (2018.01)

(58) Field of Classification Search
CPC .. A61K 38/00; A61K 39/0011; A61K 39/116; A61K 39/00; C07K 2319/00
See application file for complete search history.

(56) References Cited

U.S. PATENT DOCUMENTS

| | | | |
|---|---|---|---|
| 5,643,758 A | 7/1997 | Guan et al. | |
| 8,895,014 B2 * | 11/2014 | Fernandez ......... | A61K 39/0258 424/178.1 |
| 2002/0019342 A1 | 2/2002 | Bayer | |
| 2004/0265954 A1 | 12/2004 | Aebi et al. | |
| 2005/0287628 A1 | 12/2005 | Aebi et al. | |
| 2010/0062484 A1 | 3/2010 | Aebi et al. | |
| 2011/0274720 A1 | 11/2011 | Wacker et al. | |

FOREIGN PATENT DOCUMENTS

| | | |
|---|---|---|
| CA | 1340184 | 12/1998 |
| CA | 2360205 | 8/2000 |
| CA | 2477794 | 3/2003 |
| EP | 1481057 | 2/2006 |
| JP | 2012/100678 A | 5/2012 |
| WO | 1993025690 A1 | 12/1993 |
| WO | WO 1994/026906 | 11/1994 |
| WO | WO 2000/052135 | 9/2000 |
| WO | WO 2001/088117 | 11/2001 |
| WO | WO 2002/000856 | 1/2002 |
| WO | WO 2003/074687 | 9/2003 |
| WO | WO 2004/013151 A2 | 2/2004 |
| WO | 2005012495 A2 | 2/2005 |
| WO | WO 2005/116063 A1 | 12/2005 |
| WO | WO 2006/119987 A2 | 11/2006 |
| WO | WO2006119987 A2 * | 11/2006 |
| WO | WO 2009/104074 A2 | 8/2009 |

OTHER PUBLICATIONS

Bowie et al. (Science, 1990, 257:1306-1310).*
Johansson et al., Journal of Biotechnology, 1996; 48: 9-14.*
Regnier, Science, 1983; 222(4621): 245-252 (Year: 1983).*
Abdian et al., 2000, "Identification of essential amino acids in the bacterial α-mannosyltransferase aceA", J Biol Chem; 275(51):40568-40575.
Aebi et al., 1996, "Cloning and characterization of the ALG3 gene of *Saccharomyces cerevisiae*", Glycobiology; 6:439-444.

(Continued)

*Primary Examiner* — Gary B Nickol
*Assistant Examiner* — Lakia J Jackson-Tongue
(74) *Attorney, Agent, or Firm* — Dana L. Broughton

(57) ABSTRACT

The present invention is directed to a bioconjugate vaccine, such as an O1-bioconjugate vaccine, comprising: a protein carrier comprising a protein carrier containing at least one consensus sequence, D/E-X-N-Z-S/T, wherein X and Z may be any natural amino acid except proline; at least one antigenic polysaccharide from at least one pathogenic bacterium, linked to the protein carrier; and, optionally, an adjuvant. In another aspect, the present invention is directed to a method of producing an O1-bioconjugate in a bioreactor comprising a number steps.

9 Claims, 18 Drawing Sheets

Specification includes a Sequence Listing.

(56) References Cited

OTHER PUBLICATIONS

Ahmed et al., 2006, "Safety and immunogenicity of Escherichia coli O157 O-specific polysaccharide conjugate vaccine in 2-5 year old children", J Infect Dis; 193(4):515-521.
Alaimo et al., 2006, "Two distinct but interchangeable mechanisms for flipping of lipid-linked oligosaccharides", EMBO J; 25:967-976.
Alexander et al., 1994, "Role of the rfe gene in the biosynthesis of the Escherichia coli O7-specific lipopolysaccharide and other O-specific polysaccharides containing N-acetylglucosamine", J Bacteriol; 176:7079-7084.
Allard et al., 2001, "Epimerases:structure, function and mechanism", Cell Mol Life Sci; 58:1650-1665.
Altmann et al., 1999, "Insect cells as hosts for the expression of recombinant glycoproteins", Glycoconjugate Journal; 16:109-123.
Amor et al., 1997, "Molecular and functional analysis of genes required for expression of group IB K antigens in Escherichia coli: characterization of the his-region containing gene clusters for multiple cell-surface polysaccharides", Mol Microbiol; 26:145-161.
Anderson, 1983, "Antibody responses to Haemophilus influenzae type b and diphtheria toxin induced by conjugates of oligosaccharides of the type b capsule with the nontoxic protein $CRM_{197}$", Infection and Immunity; 39(1):233-238.
Arbeit et al., 1984, "Predominance of two newly described capsular polysaccharide types among clinical isolates of Staphylococcus aureus", Diagn Microbiol Infect Dis; 2:85-91.
Avery et al., 1929, "Chemo-immunological studies on conjugated carbohydrate-proteins. II Immunological specificity of synthetic sugar-protein antigens", J Exp Med; 50(4):533-550.
Baggett et al., 2004, "Community-onset methicillin-resistant Staphylococcus aureus associated with antibiotic use and the cytotoxin Panton-Valentine leukocidin during a furunculosis outbreak in rural Alaska", J Infect Dis; 189:1565-1573.
Baneyx et al., 1999, "Recombinant protein expression in Escherichia coli", Curr Opin Biotechnol; 10:411-421.
Baqar et al., 1995, "Safety and immunogenicity of a prototype oral whole-cell killed Campylobacter vaccine administered with a mucosal adjuvant in non-human primates",Vaccine; 13(1):22-28.
Bematchez et al., 2005, "A single bifunctional UDP-C1cNAc/Glc 4-epimerase supports the synthesis of three cell surface glycoconjugates in Campylobacter jejuni", J Biol Chem; 280:4792-4802.
Berg et al., 1997, "2-oxo acid dehydrogenase multienzyme complexes: the central role of the lipoyl domain", Biological Chemistry; 378:617-634.
Berg et al., 2001, "Sequence properties of the 1,2-diacylglycerol 3-glucosyltransferase from acholeplasma laidlawii membranes", J Biol Chem; 276(25):22056-22063.
Biiasin et al., 1998, "Identification of a gene essential for O-acetylation of the Staphylococcus aureus type 5 capsular polysaccharide", Mol Microbiol; 27:9-21.
Bilge et al., 1995, "Nonselective and efficient fluorescent labeling of glycans using 2-amino benzamide and anthranilic acid", Anal Biochem; 230(2):229-238.
Bill et al., 1995, "Expression and mutagenesis of recombinant human and murine erythropoietins in Escherichia coli", Biochimica et Biophysica Acta; 1261:35-43.
Billman-Jacobe, 1996, "Expression in bacteria other than Escherichia coli", Curr Opin Biotechnol; 7:500-504.
Bligh et al., 1959, "A rapid method of total lipid extraction and purification", Can J Biochem Physiol; 37(8):911-917.
Bourne et al., 2001, "Glycoside hydrolases and glycosyltransferases: families and functional modules", Current Opinion in Structural Biology; 11:593-600.
Branden et al., 1991, "Introduction to protein structure", Garland Publishing Inc., New York; pp. 247-268.
Breton et al., 1999, "Structure/function studies of glycosyltransferases", Current Opinion in Structural Biology; 9:563-571.

Bubeck Wardenburg et al., 2008, "Panton-Valentine leukocidin is not a virulence determinant in murine models of community-associated methicillin-resistant Staphylococcus aureus disease", J Infect Dis; 198:1166-1170.
Bugg et al., 1994, "From peptidoglycan to glycoproteins: common features of lipid-linked oligosaccharide biosynthesis", FEMS Microbiol Lett; 119:255-262.
Burda et al., 1999, "The dolichol pathway of N-linked glycosylation", Biochimica et Biophysica Acta; 1426:239-257.
Burr et al., 2005, "Prevention of disease in ferrets fed an inactivated whole cell Campylobacter jejuni vaccine", Vaccine; 23:4315-4321.
Butzler, 2004, "Campylobacter, from obscurity to celebrity", Clinical Microbiology and Infection; pp. 868-876.
Campbell et al., 1997, "A classification of nucleotide-diphospho-sugar glycosyltransferases based on amino acid sequence similarities", Biochem J; 326:929-939.
Canals et al., 2006, "The UDP N-acetylgalactosamine 4-epimerase gene is essential for mesophilic Aeromaonas hydrophila serotype O34 virulence", Infect & Immun; 74(1):537-548.
Cardini et al., 1957, "Enzymatic formation of acetylgalactosamine", J Biol Chem; 225:317-327.
Casburn-Jones et al., 2004, "Traveler's diarrhea, Journal of Gastroenterology and Hepatology", 19:610-618.
CAZy (Carbohydrate-Active enZYmes) Database—GlycosylTransferase family classification (AFMB—CNRS—Universites Aix-Marseille 1 & II) last update: Oct. 25, 2010 at http://www.cazy.org/GlycosylTransferases.html.
CAZy (Carbohydrate-Active enZYmes) Database—Home (AFMB—CNRS—Universites Aix-Marseille I & II) last update: Oct. 25, 2010 at http://www.cazy.org.
Chang et al., 2003, "Infection with vancomycin-resistant Staphylococcus aureus containing the vanA resistance gene", New Engl J Med; 348:1342-1347.
Chart et al., 1991, "Serological identification of Escherichia coli O157:H7 infection in haemolytic uraemic syndrome", The Lancet; 337:138-140.
Choi et al., 2004, "Secretory and extracellular production of recombinant proteins using Escherichia coli", Appl Microbiol Biotechnol; 64:625-635.
Consortium for Functional Glycomics (CFG) Nature, Functional glycomics gateway—Nomenclature, last update: Apr. 28, 2010 at http://ww.functionalglycomics.org/static/consortium/Nomenclature.shtml.
Coutinho et al., 1999, "Life with no sugars?", J Mol Microbiol Biotech; 1(2):307-308.
Crooks et al., 2004, "WebLogo: A sequence logo generator", Genome Research; 14(6):1188-1190.
Cruezenet et al., 2000, "Expression, purification, and biochemical characterization of WbpP, a new UDP-GlcNAc C4 epimerase from Pseudomonas aeruginosa sertype O6", J Biol Chem; 275(25):19060-19067.
Crushell et al., 2004, "Enteric Campylobacter: purging its secrets?" Pediatric Research; 55(1):3-12.
Cunnion et al., 2001, "Capsule production and growth phase influence binding of complement to Staphylococcus aureus", Infect Immun; 69:6796-6803.
Datsenko et al., 2000, "One-step inactivation of chromosomal genes in Escherichia coli K-12 using PCR products", Proc Natl Acad Sci USA; 97:6640-6645.
Dean et al., 1999, "Characterization of the serogroup O11 O-antigen locus of Pseudomonas aeruginosa PA103", J Bacteriol; 181:4275-4284.
Dejonge et al., 2007, "Clinical trial of safety and efficacy of INH-A21 for the prevention of nosocomial staphylococcal bloodstream infection in premature infants", J Pediatr; 151:260-265.
Doig et al., 1996, "Characterization of a post-translational modification of Campylobacter flagellin: identification of a sero-specific glycosyl moiety", Molecular Microbiology; 19(2):379-387.
Dunphy et al., 1967, "The plurality of long chain isoprenoid alcohols (polyprenols) from natural sources", Biochim Biophys Acta; 136: 136-147.

(56) References Cited

OTHER PUBLICATIONS

Expression Library Screening (Procaryotic) Using AP-fusion proteins (last visited Nov. 1, 2010) at http://www.protocol-online.org/cgi-bin/prt/view_cache.cgi?ID=2752.
Fairweather et al, 1986, "Cloning, nucleotide sequencing, and expression of tetanus toxin fragment C in *Escherichia coli*", Journal of Bacteriology; 165(1):21-27.
Falt et al., 1996, "Construction of recombinant aroA salmonellae stably producing the Shigella Sysenteriae sertype 1 O-antigen and structural characterization of the *Salmonella*/Shigella hybrid LPS", Microb Pathog; 20(1):11-30.
Faridmoayer et al., 2007, "Functional characterization of bacterial oligosaccharyltransferases involved in O-linked protein glycosylation", J Bacteriol; 189(22):8088-8098.
Fass et al., 1991, "Use of high densitycultures of *Escherichia coli* for high level production of recombinant Pseudomonas aeruginosa exotoxin A", Applied Microbiology and Biotechnolgy, 36(1):65-69.
Fattom et al., 1990, "Synthesis and immunologic properties in mice of vaccines composed of *Staphylococcus aureus* type 5 and type 8 capsular polusaccharides conjugated to Pseudomonas aeruginosa exotoxin A", Infect Immun; 58:2367-2374.
Fattom et al., 1993, "Laboratory and clinical evaluation of conjugate vaccines composed of *Staphylococcus aureus* type 5 and type 8 capsular polysaccharides bound to Pseudomonas aeruginosa recombinant exoprotein A", Infection and Immunity; 61(3):1023-1032.
Fattom et al., 1996, "A *Staphylococcus aureus* capsular polysaccharide (CP) vaccine and CP-specific antibodies protect mice against bacterial challenge", Infect Immun; 64:1659-1665.
Fattom et al., 1998, "Antigenic determinants of *S. aureus* type 5 and type 8 capsular polysaccharide vaccines", Infect Immun; 66:4588-4592.
Feldman et al., 2005, "Engineering N-liked protein glycosylation with diverse O antigen lipopolysaccharide structures in *Escherichia coli*", Proc Natl Acad Sci USA; 102:3016-3021.
Feng et al., 2005, "Structural and genetic characterization of the Shigella boydii type 18 O antigen", Gene; 355:79-86.
Field et al., 2003, "Structural and mechanistic basis of bacterial sugar nucleotide-modifying enzymes", Biochemistry; 42:7637-7647.
Foster et al., 1998, "Surface protein adhesins of *Staphylococcus aureus*", Trends Microbiol; 6:484-488.
Foster, 2005, "Immune evasion by staphylococci", Nature Reviews Microbiology; 3:948-958.
Francisco et al., 1992, "Transport and anchoring of β-lactamase to the external surface of *Escherichia coli*", Proc Natl Acad Sci USA: 89:2713-2717.
Fridkin et al., 2005, "Methicillin-resistant *Staphylococcus aureus* disease in three communities", N Engl J Med; 352:1436-1411.
Fry et al., 1998, "The lipopolysaccharide biosynthesis locus of Campylobacter jejuni 81116", Microbiology; 144:2049-2061.
Fujita et al., 2000, "Synthesis of neoglycoenzymes with homogenous N-linked oligosaccharides using immobilized endo-S-N-acetylglucosaminidase A", Biochmeical and Biophysical Research Communications, 267:134-138.
Gavel et al., 1990, "Sequence differences between glycosylated and non-glycosylated Asn-X-Thr/Ser acceptor sites: implications for protein engineering", Protein Eng; 3:433-442.
Gilbert et al., 2006, "Outbreak in Alberta of community-acquired (USA300) methicillin-resistant *Staphylococcus aureus* in people with a history of drug use, homelessness or incarceration", Canad Med Assoc J; 175:149-154.
Global Alliance for Vaccines and Immunization—Press releases (Mar. 11, 2006) at http://www.gavialliance.org/media_centre/press_releases/2006_03_09_en_pr_queenrania_delhi.php.
Glover et al., 2005, "Chemoenzymatic synthesis of glycopeptides with PgIB, a bacterial oligosaccharyl transferase from Campylobacter jejuni", Chemistry & Biology; 12:1311-1316.
Glover et al., 2005, "In vitro assembly of the undecaprenylpyrophosphate-linked heptasaccharide for prokaryotic N-linked glycosylation", Proc Natl Acad Sci USA; 102(40):14255-14259.
"GlycoVaxyn AG appoints renowned vaccinologist Dr. Stanley Plotkin to supervisory board", Press Release (Oct. 6, 2009) available at http://www.glycovaxyn.com/content/news/releases/09%2010%2006.pdf.
"GlycoVaxyn AG raises CHF 25 million in financing led by Edmond de Rothschild Investment Partners", Press Release (Mar. 5, 2009) available at http://www.glycovaxyn.com/downloads/GlycoVaxyn%20Financing%20Release%2005-03-09.pdf.
"GlycoVaxyn and a Harvard University affiliated hospital receive USD 3.4 million NIH grant for *Staphylococcus aureus* vaccine development", Press Release (May 4, 2010) available at http://www.glycovaxyn.com/content/news/releases/10%2005%2004.pdf.
"GlycoVaxyn appoints Philippe Dro as CEO", Press Release (May 20, 2008) available at http://www.sofinnova.fr/glycovaxy-n-appoints-phillippe-dro-as-ceo-actu-736.php.
"GlycoVaxyn opens to partnerships; series C financing round planned for 2011, CEO says mergermarket", pp. 1-2 (Nov. 25, 2009) at http://www.mergermarket.com/home/.
"GlycoVaxyn phase I clinical study shows positive data with Shigella dysenteriae vaccine candidate", (Oct. 8, 2010) available at http://www.glycovaxyn.com/content/news/releases/10%2010%2008.pdf.
"GlycoVaxyn winner of the life sciences prize 2006", Press Release (Oct. 19, 2006) available at http://www.glycovaxyn.com/content/news/releases/06%2010%2019.pdf.
"GlycoVaxyn's first clinical study with bioconjugate vaccine initiated", Press Release (Feb. 23, 2010) available at http://www.glycovaxyn.com/content/news/releases/10%2002%2023.pdf.
Goebel et al., 1929, "Chemo-immunological studies on conjugated carbohydrate-proteins" Journal of Experimental Medicine; 50(4):521-531.
Goldberg et al., 1992, "Cloning and surface expression of Pseudomonas aeruginosa O antigen in *Escherichia coli*", Proc Natl Acad Sci USA; 89(22):10716-10720.
Gordon et al., 1956, "Rapid paper chromatography of carbohydrates and related compounds", Anal Chem; 28:849-855.
Grabenhorst et al., 1999, "Genetic engineering of recombinant glycoproteins and the glycosylation pathway in mammalian host cells", Glycoconjugate Journal; 16:81-97.
Gray, 1979, "ELISA methodology for polysaccharide antigens: protein coupling of polysaccharides for adsorption to plastic tubes", J Immunol; 28:187-192.
Guan et al., 2005, "Extraction and identification by mass spectrometry of undecaprenyl diphosphate-MurNAc-pentapeptide-GlcNAc from *Escherichia coli*", Anal Biochem; 345:336-339.
Guo et al., 2007, "Three UDP-hexose 4-epimerases with overlapping substrate specificity coexist in *E. coli* O86:B7", Biochem Biophys Res Commun; 356:604-609.
Haberberger et al., 1994, "Prospects and problems for development of a vaccine against diarrhea caused by Campylobacter", Vaccine Research; 3:15-22.
Helenius et al., 2004, "Roles of N-linked glycans in the endopasmic reticulum", Annu Rev Biochem; 73:1019-1049.
Higgins et al., 2004, "Structure of the periplasmic component of a bacterial drug efflux pump", Proc Natl Acad Sci USA; 101:9994-9999.
Hoffmeister et al., 2001, "Two sequence elements of glycosyltransferases involved in urdamycin biosynthesis are responsible for substrate specificity and enzymatic activity", Chem & Bio; 8:557-567.
Hofmann et al., 1993, "A database of membrane spanning protein segments", Biol Chem; 374:166 (abstract).
Hoiseth et al., 1981, "Aromatic-dependent *Salmonella typhimurium* are non-virulent and effective as live vaccines", Nature; 291:238-239.
Ihssen et al., 2010, "Production of glycoprotein vaccines in *Escherichia coli*", Microbial Cell Factories; 9(1):61.

(56) References Cited

OTHER PUBLICATIONS

Imperiali et al., 1991, "Differences between Asn-Xaa-Thr-containing peptides; a comparison of solution conformation and substrate behavior with oligosacchary1-transferase", Biochemistry; 30:4374-4380.
International Search Report of International application No. PCT/CH03/00153, dated May 19, 2003.
International Search Report of International application No. PCT/EP2006/004397, dated Dec. 13, 2006.
International Search Report of International application No. PCT/EP2011/057111, dated Jul. 28, 2011.
Jeong et al., 2001, "Secretory production of human granulocyte colony-stimulating factor in *Escherichia coli*", Protein Expression and Purification; 23:211-318.
Johnson et al., 1999, "Alignment and structure prediction of divergent protein families: periplasmic and outer membrane proteins of bacterial efflux pumps", J Mol Biol; 287:695-715.
Johnson et al., 1999, "Synthesis of oligosaccharides by bacterial enzymes", Glycoconjugate Journal; 16:141-146.
Jones et al., 2005, "Revised structures for the capsular polysaccharides from *Staphylococcus aureus* types 5 and 8, components of novel glycoconjugate vaccines", Carbohydr Res; 340:1097-1106.
Josefsson et al., 2001, "Protection against experimental *Staphylococcus aureus* arthritis by vaccination with clumping factor A, a novel virulence determinant", Journal of Infectious Diseases; 184:1572-1580.
Jursch et al., 1994, "Histidine residues near the N terminus of staphylococcal alpha-toxin as reporters of regions that are critical for oligomerization and pore formation", Infect Immun; 62(6):2249-2256.
Kaniuk et al., 2004, "Investigation of the structural requirements in the lipopolysaccharide core acceptor for ligation of O antigens in the genus *Salmonella*: WaaL 'ligase' is not the sole determinant of acceptor specificity", J Biol Chem; 279:36470-36480.
Kapitonov et al., 1999, "Conserved domains of glycosyltransferases", Glycobiol; 9(10):961-978.
Karlyshev et al., 2004, "The Campylobacter jejuni general glycosylation system is important for attachment to human epithelial cells and in the colonization of chicks", Microbiology; 150; 1957-1964.
Kazakova et al., 2005, "A clone of methicillin-resistant *Staphylococcus aureus* among professional football players", N Engl J Med; 352:468-475.
Kean, 1966, "Separation of gluco- and galactocerebrosides by means of borate thin-layer chromatography", J Lipid Res; 7:449-452.
King et al., 2006, "Emergence of community-acquired methicillin-resistant *Staphylococcus aureus* USA 300 clone as the predominant cause of skin and soft-tissue infections", Ann Intern Med; 144:309-317.
Kiser et al., 1999, "*Staphylococcus aureus* cap5P encodes a UDP-N-acetylglucosamine 2-epimerase with functional redundancy", J Bacteriol; 181(16):4818-4824.
Klevens et al., 2007, "Invasive methicillin-resistant *Staphylococcus aureus* infections in the United States," Jama 298: 1763-71.
Knirel et al., 1988, "Somatic antigens of Shigella: structure of the O-specific polysaccharide chain of the Shigella dysenteriae type 7 lipoplysacharide.".
Kollef eta l., 2005, "Epidemiology and outcomes of health-care associated pneumonia: results from a large US database of culture-positive pneumonia." Chest 128:3854-3862.
Konadu et al. 1998, "Investigational vaccine for *Escherichia coli* O157: phase 1 study of O157 O-specific polysaccharide-pseudomonas aeruginosa recombinant exoprotein A conjugates in adults", Journal of Infectious Diseases; 177(2):383-387.
Konadu et al., 1994, "Preparation, characterization, and immunological properties in mice of *Escherichia coli* O157 O-specific polysaccharide—protien conjugate vaccines", Infection and Immunity; 62(11):5048-5054.

Konadu et al., 1999, "Syntheses and immunologic properties of *Escherichia coli* O157 O-specific polysaccharide and shiga Toxin 1 B subunit conjugates in mice," Infection and Immunity; 67(11):6191-6193.
Kowarik et al., 2006, "N-Linked glycosylation of folded proteins by the bacterial oligosaccharyltransferase", Science; 314:1148-1150.
Kowarik et al., 2006, "Definition of the bacterial N-glycosylation site consensus sequence", EMBO J; 25(9):1957-1966.
Kuwajima et al., 1986, "Nucleotide sequence of the hag gene encoding flagellin of *Escherichia coli*", J Bacteriol; 168(3):1479-1483.
Laemmill, 1970, "Cleavage of Structural Proteins during the Assembly of the Head of bacteriophage T4." Nature 227:680-685.
Law, 2000, "Virulence factors of *Escherichia coli* O157 and other Shiga Toxin-producing *E-coli*." J. App. Microbiol. 88:729-745.
Lee et al., 1997, "Protective efficacy of antibodies to the *Staphylococcus aureus* type 5 capsular polysaccharide in a modified model of endocarditis in rats." Infect Immun. 65:4146-51.
Lee et al., 1999, "Evaluation of a truncated recombinant flagellin subunit vaccine against Campy/obaeter jejuni", Infection and Immunitv; 67(11):5799-5805.
Lefebre, 2002, "Construction and Evaluation of Plasmind vectors Optimized for Consitutive and Regulated Gene Expression in Burkholderia cepacia Complex Isolates," Appl. Environ Microbiol. 68:5956-5964.
Linton et al., 2002, "Identification of N-acetylgalactosamine-containing glycoproteins PEB3 and CgpA in Campylobacter jejuni", Molecular Microbiology; 43(2):497-508.
Linton et al., 2005, "Functional analysis of the Campylobacter jejuni N-linked protein glycoylation pathway", Molecular Microbiology; 55(6):1695-1703.
Liu et al., 2008, "Structure and genetics of Shigella O antigens." FEMS Microbiol. 32:627-653.
Lodish et al., 2000 "DNA Cloning with Plasmid vectors." Molec. Cell. Biology; 7.1 at http://www/ncbi.nlm.nih.gov/bookshelf/br.fcgi?book=mcb&part=A1582.
Lodish et al., 2000 "Protein Glycosylation in the ER and Golgi Complex"; 17.7 at http://www/ncbi.nlm.nih.gov/bookshelf/br.fcgi?book=mcb&part=A4816.
Lowy, 1998, "*Staphylococcus aureus* infections." New Eng. J Med. 339:520-32.
Lukac et al., 1988, "Toxoid of pseudomonas aeruginosa exotoxin A generated by deletion of an active-site residue", Infection and Immunity; 56(12):3095-3098.
Malissard et al., 1999, "The yeast expression system for recombinant glycosyltransferases", Glycoconjugate Journal; 16:125-139.
Maras et al., 1999, "Filamentous fungi as production organisms for glycoproteins of bio-medical interest", Glycoconjugate Journal; 16:99-107.
Marolda et al., 2006, "Interplay of the wzx translocase and the corresponding polymerase and chain length regulator proteins in the translocation and periplasmic assembly of lipopolysaccharide O antigen", Journal of Bacteriology; 188(14):5124-5135.
Marth et al., 1999, "Essentials of Glycobiology" Chapter 7 (Varki et al. eds.) available at http://www/ncbi.nlm.nih.gov/bookshelf/br.fcgi?book=glyco&part=A465.
Mcdevitt eta l., 1995, "Indentification of the ligand-binding domain of the surface-located fibrinogen receptor (clumping factor) of *Staphylococcus aureus*." Molecular Microbiology 16:895-907.
Mcdougal et al., 2003, "Pulsed-field gel electrophoresis typing of oxacillin-resistant *Staphylococcus aureus* isolates from the United States; establishing a national database." J. Clin. Microbiol. 41:5113-20.
Meier-Dieter, 1990, "Biosyntehsis of enterobacterial common antigen in *Escherichia coli*." J. Biol. Chem.; 265:13490-13497.
Menzies et al., 1996, "Passive immunization with antiserum to a nontoxic alpha-toxin mutant from *Staphylococcus aureus* is protective in a murine model." Infect Immun. 64:1839-41.
Merry et al., 2002, "Recovery of intact 2-aminobenzamide-labeled O-glycans released from glycoproteins by Hhydrazinolysis." Anal Biochem; 304(1):91-99.
Messner, 1997, "Bacterial glycoproteins," Glycoconjugate Journal 14:3-11.

(56) References Cited

OTHER PUBLICATIONS

Middlebrook et al., 1984, "Bacterial toxins: cellular mechanisms of action", Microbiological Reviews; 48(3): 199-221.
Mikusova et al., 2005, "Decaprenylphosphoryl Arabinofuranose, the Donor of the D-Arabinofuranosyl Residues of Mycobacterial Arabinan, is formed via a Two-Step Epimerization of Decaprenylphosphoryl Ribose." J. Bacteriol. 187:8020-8025.
Moreillon et al., 1995, "Role of *Staphylococcus aureus* coagulase and clumping factor in pathogenesis of experimental endocarditis." Infection & Immunity; 63:4738-43.
Muller et al., 2005, "An ATP-binding cassette-type cysteine transporter in *Campylobacter jejuni* inferred from the structure of an extracytoplasmic solute receptor protein", Mol Microbiol; 57:143-155.
Nairn et al., 1990, "Solutions, emulsions, suspensions and extracts", Remington's Pharmaceutical Sciences, 18th ed., Mack Publishing Co., Chapter 83, pp. 1519-1544.
Nanra et al, 2009, "Heterogenous in vivo expression of clumping factor A and capsular polysacchardie *Staphylococcus aureus*: Implications for vaccine design." Vaccine; 27:3276-80.
Nilsson et al.m, 1997, "The role of staphylococcal polysaccharide microcapsule expression in septicemia and septic arthritis." Infect Immun 65:4216-4221.
Nita-Lazar et al., 2005, "The N-X-S/T consensus sequence is required but not sufficient for bacterial N-linked protein glycosylation", Glycobiology; 15(4):361-367.
Notice of Abandonment of U.S. Appl. No. 10/506,917, dated Sep. 12, 2008.
Office Action of U.S. Appl. No. 10/506,917, dated Jan. 23, 2008.
Office Action of U.S. Appl. No. 10/506,917, dated May 9, 2007.
Office Action of U.S. Appl. No. 11/920,175, dated Nov. 9, 2011.
Office Action of U.S. Appl. No. 12/219,383, dated Jul. 23, 2009.
Office Action of U.S. Appl. No. 12/219,383, dated Mar. 20, 2009.
Office Action of U.S. Appl. No. 12/219,383, dated May 12, 2010.
Office Action of U.S. Appl. No. 12/219,383, dated Oct. 28, 2010 (Interview Summary).
Office Action of U.S. Appl. No. 12/219,383, dated Oct. 3, 2011.
O'Riordan et al., 2004, "*Staphylococcus aureus* capsular polysaccharides." Clin Microbiol Rev. 17(1):218-34.
Paetzel et al., 2002, "Signal peptidases", Chem Rev; 102:4549-4580.
Panina-Bordignon et al., 1989, "Universally immunogenic T cell epitopes: promiscuous binding to human MHC class II and promiscuous recognition by T cells" European Journal of Immunolgy; 19:2237-2242.
Parkhill et al., 2000, "The genome sequence of the food-borne pathogen Campylobacter jejuni reveals hypervariable sequences", Nature; 403:665-668.
Passwell et al., 2001, "Safety and immunogenicity of improved Shegella O-specific polysaccharide-protein conjugate vaccines in adults in Israel", Infection and Immunity, 69(3):1351-1357.
Paton & Paton, 1999, "Molecular Characterization of the Locus Encoding Biosynthesis of the Lipopolysaccharide O Antigen of *Escherichia coli* Serotype O113," Infect & Immun. 67(11): 5930-5937.
Pawlowski, 2000, "Preparation of pneumococcal capsular polysaccharide- protein conjugate vaccines utilizing new fragmentation and conjugation technologies." Vaccine 18:1873-1885.
Pearson et al., 2003, "Comparative genome analysis of Campylobacter jejuni using whole genome DNA microarrays", FEBS Letter; 554: 224-230, FEBS 27782.
Perry, 1986, "Structure of the O-chain polysaccharide of the phenol-phase soluble lipopolysaccharide of *Escherichia coli* 0:157:h7." Biochem. Cell Biol.; 64:21-28.
Petrescu et al., 2004, "Statistical analysis of the protein environment of N-glycosylation sites: implications for occupancy, structure, and folding", Glycobiology; 14(2):103-114.

Pozscay et al., 1999, "Protein conjugates of synthetic saccharides elicit higher levels of serum IgG lipopolysaccharide antibodies in mice than do those of the O-specific polysaccharide from Shigella dysenteriae type 1", Proc Natl Acad Sci USA; 96:5194-5197.
Pozsgay, 1998, "Synthesis of glycoconjugate vaccines again Shigella dysenteriae type 1", Journal of Organic Chemistry; 63:5983-5999.
Qian et al., 2007, "Conjugating recombinant proteins to Psudomonas aeruglnosa Exoprotein A: A strategy for enhancing immunogenicity to malaria vaccine candidates." Vaccine 25:3923-3933.
Raetz et al., 2002, "Lipopolysaccharide endotoxins", NIH-PA author manuscript, pp. 1-57, 19-25 (published in final edited form as: Annual Rev Biochem; 71:635-700, 2002.
Reeves et al., 1996, "Bacterial polysaccharide synthesis and gene nomenclature", Reviews, Elseview Science Ltd., pp. 495-503.
Robbins et al, 2009, "Synthesis, characterization, and immunogenicity in mice on Shigella sonnei O-specific oligosacchardie-core-protein conjugates." Proc. Natl. Acad Sci USA 106:7974-7978.
Royle et al., 2002, "An analytical and structural database provides a strategy for sequencing O-glycans from microgram quantities of glycoproteins." Anal Biochem; 304(1): 70-90.
Rubires, 1997, "A gene (wbbL) from Serratia marcesens N28b (O4) complements the rfb-50 mutation of *Escherichia coli* K-12 derivatives" J Bacteriol 179(23):7581-7586.
Rudd et al., 1997, "Glycosylation: heterogeneity and the 3D structure of proteins", Crit Rev Biochem Mol Biol; 32:1-100.
Rush, 1997, "Polyisoprenyl phosphate specificity of UDP-GlcNAc: undecaprenyl phosphate N-acetylgluosaminyl 1-P transferase from *E. coli*" Glycobiology; 7:315-322.
Sambrook & Russell, 2006, "Screening Bacterial Colonies by Hybridization: Small Numbers." Cold Spring Harb. Protoc; doi:10.1101/pdb.prot3925 at http://cshprotocols.cshlp.org/cgi/content/full/2006/2/pdb.prot3925.
Samuel, 2003, "Biosynthesis of O-antigens: genes and pathways involved in nucleotide sugar precursor synthesis and O-antigen assembly." Carbohydrate Res. 338: 2503-2519.
Sau et al., 1997, "The *Staphylococcus aureus* allelic genetic loci for serotype 5 and 8 capsule expression contain the type-specific genes flanked by common genes." Microbiology 143: 2395-405.
Schaad et al., 1991, "Safety and immunogenicity of Pseudomonas aeruginosa conjugate A vaccine in cystic fibrosis", The Lancet; 338:1236-1237.
Schaffer et al, 2008, "Vaccination and passive immunisation against *Staphylococcus aureus*" Ing J Antimicrob Agents 32 Suppl. 1:S71-78.
Schneerson et al., 1991, "Preparation, characterization, and immunogenicity of Haemophilus influenzae type B polysaccharide-proteins conjugates", Journal of Experimental Medicine; 152:361-376.
Schultz et al., 1998, "Prototype of a heme chaperone essential for cytochrome c maturation", Science; 281:1197-1200.
Schwimmer et al., 1956, "Reagent for Differentiation on 1,4- and 1,6-Linked Glucosaccharides." Science; 123:543-544.
Scott, 1997, "Vaccines against Campylobacter jejuni", Journal of Infectious Diseases; 176(Suppl. 2):S183-S188.
Seffernick et al., 2001, "Melamine deaminase and atrazine chlorohydrolase: 98 percent identical but functionally different", J Bacteriol; 183(8):2405-2410.
Shorr, 2007, "Epidemiology and economic impact of meticillin-resistant *Staphylococcus aureus*: review and analysis of the literature." Phamacoeconomis 25: 751-68.
Simons et al., 1984, "High-level expression of human interferon gamma in *Escherichia coli* under control of the $p_L$ promoter of bacteriophage lambda", Gene; 28:55-64.
Spears et al., 2006, "A comparison of enterphathogenic *Escherichia coli* pathogenesis," FEMS Microbiol. Lett 255:187-202.
Spirig et al., 1997, "The STT3 protein is a component of the yast oligosaccharyltransferase complex." Mol. Gen Genet 356:628-637.
Stenutz, 2006, "The structures of *Escherichia coli* O-polysaccharide antigens." FEMS Microbiol. Rev. 30: 382-403.
Stephan et al., 2004, "First isolation and further characterization of enteropathogenic *Escherichia coli* (EPC) O157:H45 strains from cattle" BMC Microbiol. 4:10.

(56) References Cited

OTHER PUBLICATIONS

Stevenson, 1994, "Structure of the O Antigen of *Escherichia coli* K-12 and the Sequence of rfb Gene Cluster." J Bacteriol.; 176:4144-4156.
Sullam, 1996, "Diminished platelet binding in vitro by *Staphylococcus areus* is associated reduced virulence in a rabbit model of infective endocarditis." Infection & Immun. 66:5183-5189.
Szu et al., 1994, "Laboratory and preliminary clinical characterization of Vi capsular polysaccharide-protein conjugate vaccines", Infection and Immunity; 62(10):4440-4444.
Szymanski et al., 1999, "Evidence for a system of general protein glycosylation in Campylobacter jejuni", Molecular Microbiology; 32(5):1022-1030.
Szymanski et al., 2002, "Campylobacter protein glycosyation affects host cell interactions", Infection and Immunity; 70(4):2242-2244.
Szymanski et al., 2005, "Protein glycosylation in bacterial mucosal pathogens", Nature Reviews, Microbiology; 3:225-237.
Taylor et al., 1993, "Synthesis, characterization and clinical evaluation of conjugate vaccines composed of the O-specific polysaccharides of Shigella dysenteriae type 1, Shigella flexneri type 2a, and Shigella sonnei (Plesiomonas shigelloides) bound to bacterial toxoids", Infection and Immunity; 61(9):3678-3687.
Thakker et al., 1998, "*Staphylococcus aureus* serotype 5 capsular polysaccharide is antiphagocytic and enhances bacterial virulence in a murine bactermia model." Infect Immun. 66:5183-5189.
Thibault et al., 2001, "Identification of the carbohydrate moieties and glycosylation motifs in Campylobactor jejuni flagellin", J Biol Chem; 276(37):34862-34870.
Tsai et al., 1982, "A sensitive silver stain for detecting lipopolysaccharides in polyacrylamide gels." Anal Biochem. 119:115-119.
Tuchscherr, 2008, "Antibodies to capsular polysaccharide and clumping factor A prevent mastitis and the emergence of uncapsulated and small-colony variants of *Staphylococcus aureus* in mice." Infect Immun 76:5738-44.
Unligil et al., 2000, "Glycosyltransferase structre and mechanism." Curr. Op. Struct. Bio. 10:510-517.
Valvano, 2003, "Export of O-specific lipopolysaccharide", Front Biosci; 8:s452-471.
Vanbleu et al., 2004, "Genetic and physical map of the pLAFR1 vector DNA seq." 15(3): 225-227.
Vandaux et al, 1995, "Use of adhesion-defective mutants of *Staphylococcus aureus* to define the role of specific plasma proteins in promoting bacterial adhesion to canine arteriovenous shuts." Infect & Immunity 63:585-90.
Varki et al., 1999, "Essentials of Glycobiology", Cold Spring Harbor Laboratory Press; Cold Spring Harbor, New York pp. 85-100.
Vernachio et al., 2003, "Anti-clumping factor A immunoglobulin reduces the duration of methicillin-resistant *Staphylococcus aureus* bacteremia in an experimental model of infective endocarditis," Antimicrobial Agents & Chemotherapy, 47:3400-3406.
Wacheter et al., 1976, "Lipid Intermediates Involved in the Assembly of Membrane-Associated Glycoproteins in Calf Brain White Matter." Arch Biochem Biophys.; 174:726-737.
Wacker et al., 2001, "PglB, an oligosaccharyltransferase in the eubacterium Campylobacter jejuni?", Glycobiology; 11:871.
Wacker et al., 2002, "N-linked glycosylation in Campylobacter jejuni and its functional transfer into *E. coli*", Science; 298:1790-1793.
Wacker et al., 2006, "Substrate specificity of bacterial oligosaccharyltransferase suggests a common transfer mechanism for the bacterial and eukaryotic systems", Proc Natl Acad Sci; 103:7088-7093.
Waechter et al., 1977, "Evidence for the Enzymatic Transfer of N-Acetylglucosamine form UDP-N-Acetylglucosamine into Dolichol Derivates and glycoproteins by Calf Brain Membrane." Arch. Biochem. Biophys. 181:185-198.
Wang et al., 2002, "The O-Antigen gene Cluster of *Escherichia coli* O55:H7 and Identification of a New UDP-GlcNAc C4 Epimerase Gene." J Bacteriol 184:2620-2625.
Wang et al.,1998, "Organization of *Escherichia coli* O157 O Antigen Gene cluster and Identification of its specific genes." Infect. Immune 66:3545-3551.
Watts et al., 2005, "*Staphylococcus aureus* strains that express serotype 5 of srotype 8 capsular polysaccharides differ in virulence," Infect Immun. 73:3502-11.
Wernerus et al., 2004, "Biotechnological applications for surface-engineered bacteria", Biotechnol Appl Biochem; 40:209-228.
Whisstock et al., 2003, "Prediction of protein function from protein sequence and structure", Q Rev Biophys; 36(3):307-340.
Whitfield et al., 1999, "Structure, assembly and regulation of express of capsules in *Escherichia coli*", Molecular Microbiology; 31(5):1307-1319.
Whitfield et al., 2006, "Biosynthesis and Assembly of Capsular Polysaccharides in *Escherichia coli*." Annu Rev. Biochem. 75:39-68.
Witkowski et al., 1999, "Conversion of a beta-ketoacyl synthase to a malonyl decarboxylase by replacement of the active-site cysteine with glutamine", Biochemistry; 38(36):11643-11650.
Wolfe et al., 1993, "Reactions adding Sugar Units to Proteins in the ER and Golgi Complex, Molecular and Cellular Biology." Wadsworth Publishing Co., CA 873-75.
Wyszynska et al., 2004, "Oral immunization of chickens with avirlent *salmonella* vaccine strain carrying C. jejuni 72Dz/92 cjaA gene elicits specific humoral immune response associated with protection against challenge with wild-type Campylobacter", Vaccine; 22:1379-1389.
Yao et al., 1994, "Isolation of motile and non-motile insertional mutants of Campylobacter jejuni: the role of motility in adherence and invasion of eukaryotic cells", Molecular Microbiology; 14(5):883-893.
Young et al., 2002,"Structure of the N-linked glycan present on multiple glycoproteins in the gramnegative bacterium, Campylobacter jejuni", J Biol Chem; 277(45):42530-42539.
Zhang et al., 1997, "Molecular and chemical characterization of the lipopolysaccharide O-antigen and its role in the virulence of Yersinia enterocolitica serotype O:8." Mol. Microbiol. 23:63-76.
Zufferey eta l., 1995, "STT3, a highly conserved protein required for yeast oligosaccharyl transferase activity in vivo." The EMBO Journal 14(20):4949-4960.
Nita-Lazar, et al., Annual Conference of the Society for Glycobiology; Oct. 2002; vol. 12, No. 10; pp. 686; abstract #131.
Corey D. R., Synthesis of Oligonucleotide-Peptide and Oligonucleotide-Protein Conjugates. Bioconjugation Protocols Strategies and Method, Jul. 1, 2004, vol. 283, pp. 1-319 p. 204.

\* cited by examiner

FIGURE 6A 2 fermentation runs, various purification steps

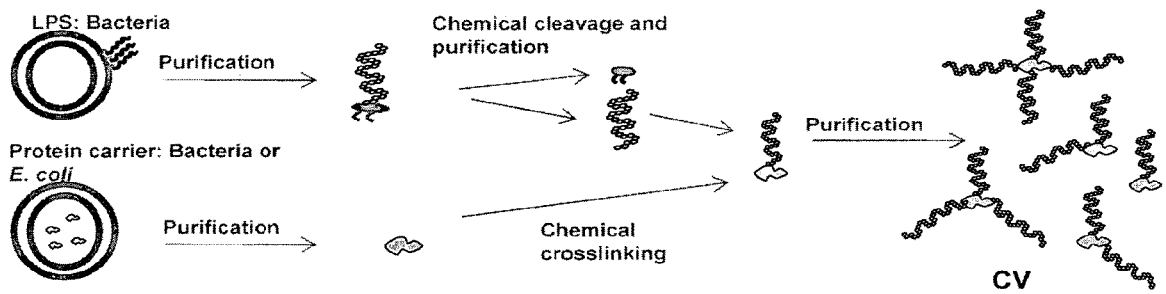

1 fermentation run, fewer purification steps

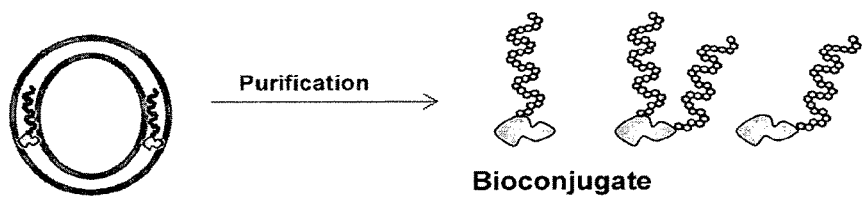

FIGURE 6B galF:   subunit of glucose-1-phosphate uridylyltransferase
rmlB:   dTDP-glucose 4,6-dehydratase
rmlD:   dTDP-4-dehydrorhamnose reductase
rmlA:   dTDP-glucose pyrophosphorylase
rmlC:   dTDP-4-dehydrorhamnose 3,5-epimerase
wzx:    O-antigen flippase
wzy:    O-antigen polymerase
wbbR:   rhamnosyl transferase II
wbbQ:   rhamnosyl transferase I
rfpA:   not required
wbbP:   galactosyl transferase

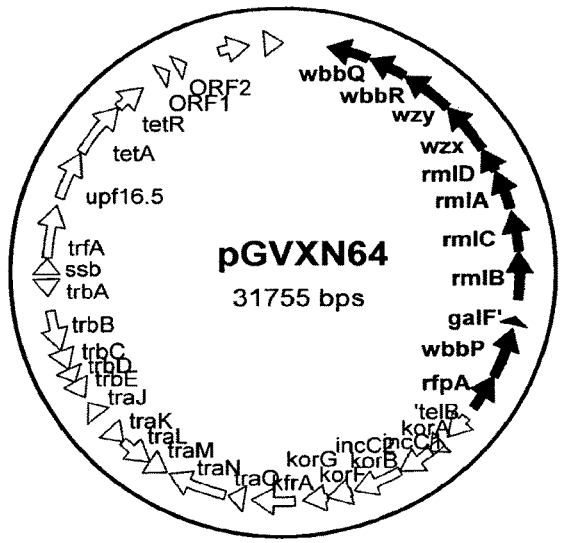

FIGURE 9
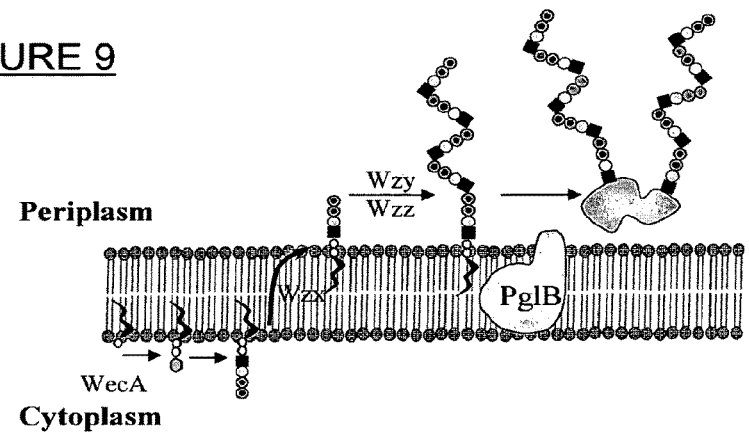
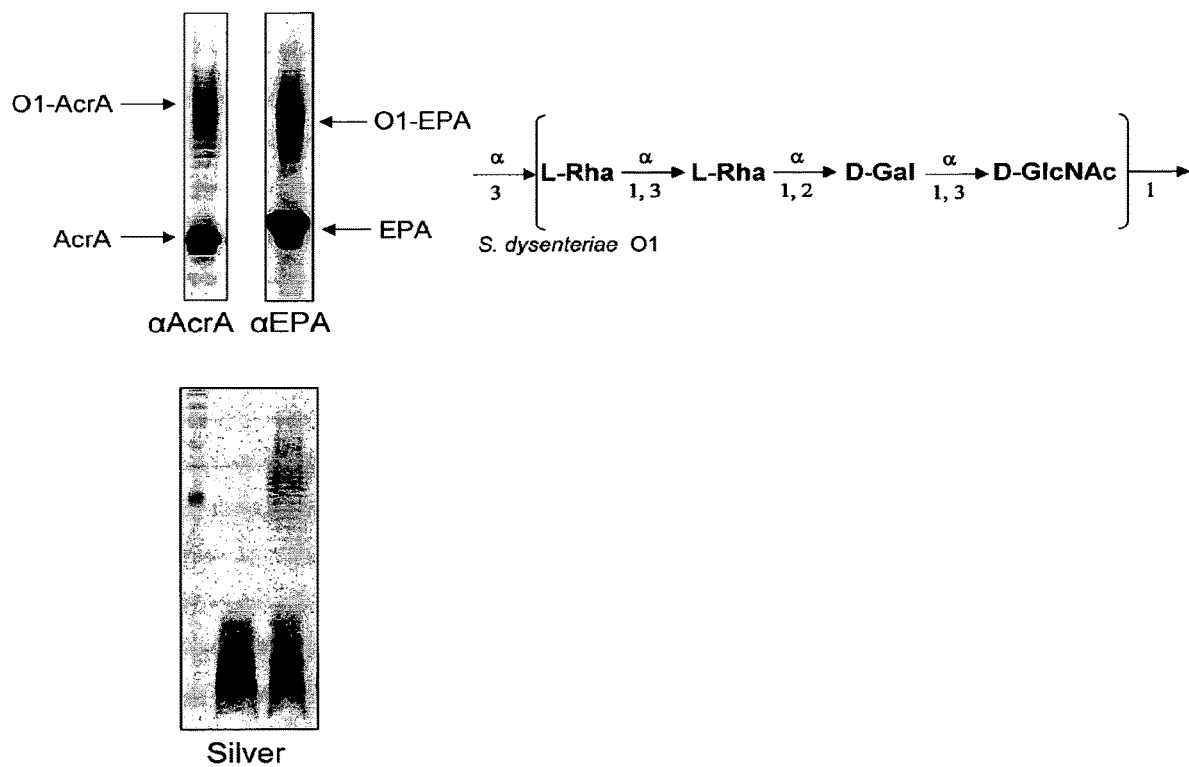

FIGURE 11
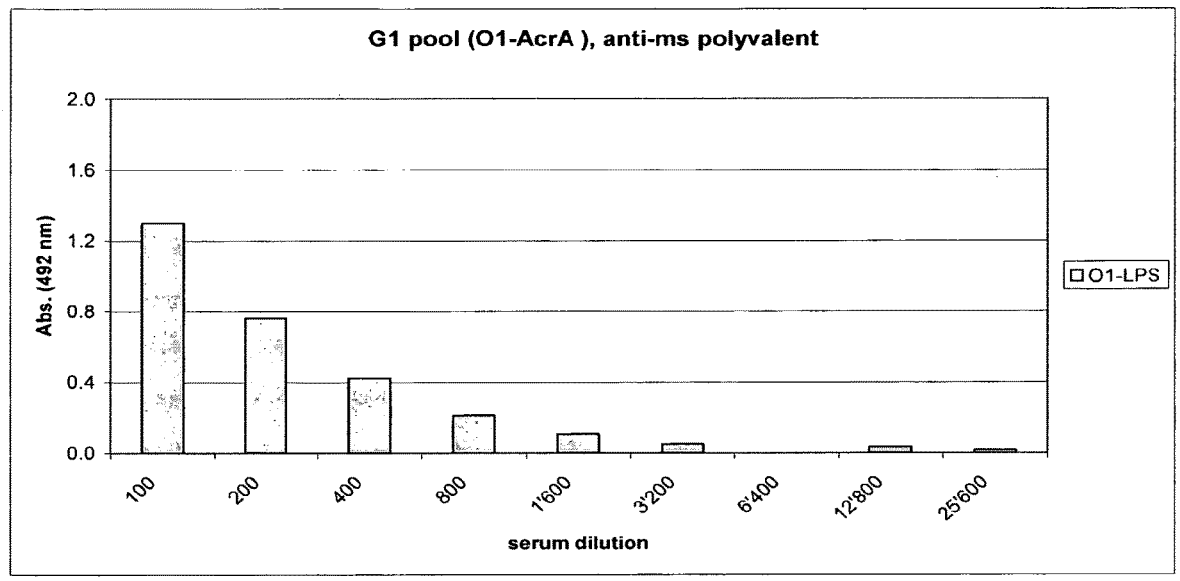
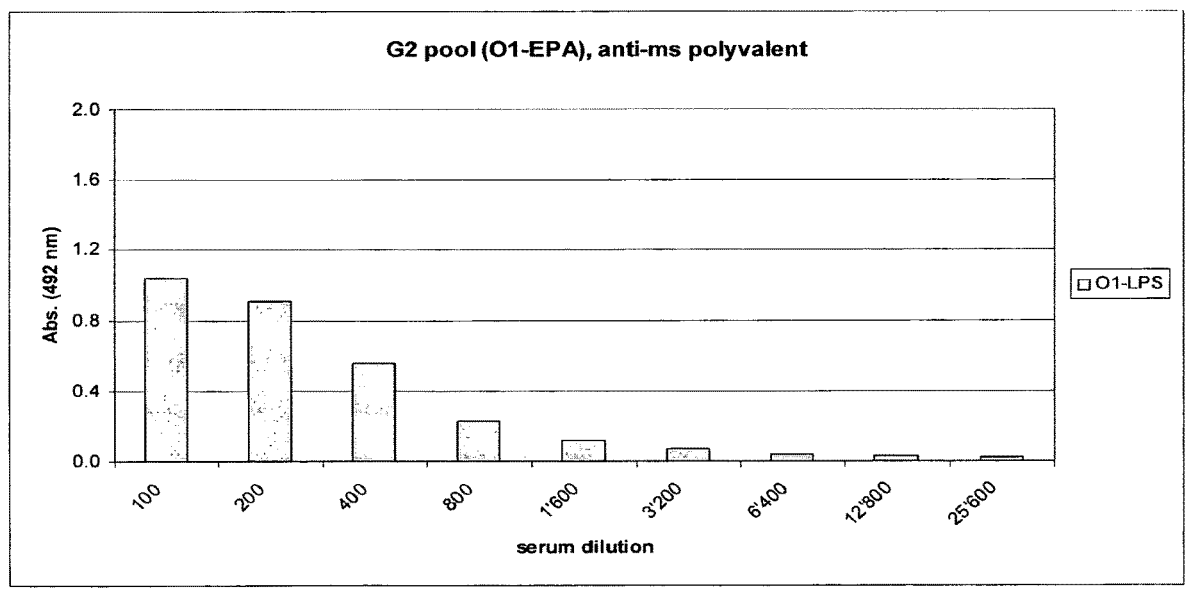

1. Whole cells
2. Periplasmic Extract
3. IEX Load (Source Q)
4. IEX Eluate 1
5. IEX Eluate 2
6. Eluate 1 (Fluoroapatite)

Expansion of anomeric region of $^1$H NMR spectrum of O1-EPA

BIOCONJUGATES MADE FROM RECOMBINANT N-GLYCOSYLATED PROTEINS FROM PROCARYOTIC CELLS

This application is a continuation of U.S. patent application Ser. No. 14/735,773, filed Dec. 14, 2010, which is a U.S. national stage entry of International Patent Application No. PCT/IB2009/000287, filed Feb. 19, 2009, which claims benefit of U.S. Provisional Patent Application Nos. 61/064,163, filed Feb. 20, 2008; 61/071,545, filed May 5, 2008; 61/129,480, filed Jun. 30, 2008; 61/129,852, filed Jul. 24, 2008; and 61/136,687, filed Sep. 25, 2008, each of which are incorporated herein by reference in their entirety.

FIELD OF THE INVENTION

The present invention relates to bioconjugates, specifically bioconjugate vaccines, made from recombinant glycoproteins, namely N-glycosylated proteins. The invention comprises one or more introduced N-glycosylated proteins with optimized amino acid consensus sequence(s), nucleic acids encoding these proteins as well as corresponding vectors and host cells. In addition, the present invention is directed to the use of said proteins, nucleic acids, vectors and host cells for preparing bioconjugate vaccines. Furthermore, the present invention provides methods for producing bioconjugate vaccines.

BACKGROUND OF THE INVENTION

Glycoproteins are proteins that have one or more covalently attached sugar polymers. N-linked protein glycosylation is an essential and conserved process occurring in the endoplasmic reticulum of eukarotic organisms. It is important for protein folding, oligomerization, stability, quality control, sorting and transport of secretory and membrane proteins (Helenius, A., and Aebi, M. (2004). Roles of N-linked glycans in the endoplasmic reticulum. Annu. Rev. Biochem. 73, 1019-1049).

Protein glycosylation has a profound influence on the antigenicity, the stability and the half-life of a protein. In addition, glycosylation can assist the purification of proteins by chromatography, e.g. affinity chromatography with lectin ligands bound to a solid phase interacting with glycosylated moieties of the protein. It is therefore established practice to produce many glycosylated proteins recombinantly in eukaryotic cells to provide biologically and pharmaceutically useful glycosylation patterns.

It has been demonstrated that a bacterium, the food-borne pathogen *Campylobacter jejuni*, can also N-glycosylate its proteins (Szymanski, et al. (1999). Evidence for a system of general protein glycosylation in *Campylobacter jejuni*. Mol. Microbiol. 32, 1022-1030). The machinery required for glycosylation is encoded by 12 genes that are clustered in the so-called pgl locus. Disruption of N-gylcosylation affects invasion and pathogenesis of *C. jejuni* but is not lethal as in most eukaryotic organisms (Burda P. and M. Aebi, (1999). The dolichol pathway of N-linked glycosylation. Biochim Biophys Acta 1426(2):239-57). It is possible to reconstitute the N-glycosylation of *C. jejuni* proteins by recombinantly expressing the pgl locus and acceptor glycoprotein in *E. coli* at the same time (Wacker et al. (2002). N-linked glycosylation in *Campylobacter jejuni* and its functional transfer into *E. coli*. Science 298, 1790-1793).

Diarrheal illness is a major health problem associated with international travel in terms of frequency and economic impact. Traveller's diarrhea refers to an enteric illness acquired when a person travels from a developed to a developing country. Today, over 50 million people travel each year from developed countries to developing countries and up to 50% of these travelers report having diarrhea during the first 2 weeks of their week of their stay. There has been no significant decline in the incidence of traveller's diarrhea since the 1970s, despite efforts made by the tourism industry to improve local infrastructure.

Traveller's diarrhea is acquired through the ingestion of faecally contaminated food and less commonly water. Bacteria are the main cause of traveller diarrhea's, being responsible for up to 80% of the infections. Enterotoxigenic *E. coli*(ETEC) is the most frequently isolated bacterium in all parts of the world associated with traveler's diarrhea, followed by *Shigella* spp and *C. jejuni*.

Shigellosis remains a serious and common disease. In addition to causing watery diarrhea, Shigellae are a major cause of dysentery (fever, cramps, and blood and/or mucus in the stool). Man is the only natural host for this bacterium. The estimated number of *Shigella* infections is over 200 million annually. About 5 million of these cases need hospitalization and a million people die. Three serogroups are mostly responsible for the disease described as bacillary dysentery: *S. dysenteriae*, *S. flexneri* and *S. sonnei*.

*S. dysenteriae* and *S. flexneri* are responsible for most infections in the tropics, with case fatalities up to 20%. Shigellosis occurs both endemically and as epidemics. In many tropical countries, endemic infection is largely due to *S. flexneri* whereas major epidemics of *S. dysenteriae* have occurred in Central America, Central Africa and Southeast Asia. These epidemics are major public-health risks. Infections, primarily due to *S. sonnei* and less frequently *flexneri* continue to occur in industrialized countries.

Conjugate vaccines have shown promising results against *Shigella* infections. O-specific polysaccharides of *S. dysenteriae* type 1 have been used to synthesize a conjugate vaccine that has elicited an immune response in mice. Such vaccines have been synthesized chemically and conjugated to human serum albumin or has been developed where the O-polysaccharide has been purified from *Shigella*. The O-specific polysaccharides of *S. sonnei* and *S. flexneri* also have been conjugated chemically to *P. aeruginosa* exotoxin and have elicited a significant immune response in mice. Additionally, they have been shown to be immunogenic and safe in humans. However, chemical conjugation is an expensive and time-consuming process that does not always yield reliable and reproducible vaccines. This leads to good manufacturing practices (GMP) problems when seeking to develop such bioconjugate vaccines on a commercial scale.

SUMMARY OF THE INVENTION

In one aspect, the present invention is directed to a bioconjugate vaccine comprising: a protein carrier comprising an inserted consensus sequence, D/E-X-N-Z-S/T, wherein X and Z may be any natural amino acid except proline; at least one antigenic polysaccharide from at least one bacterium, linked to the protein carrier, wherein the at least one antigenic polysaccharide is at least one bacterial O-antigen from one or more strains of *Shigella*, *E. coli* or *Pseudomonas aeruginosa*; and, optionally, an adjuvant.

In another aspect, the present invention is directed to a *Shigella* bioconjugate vaccine comprising: a protein carrier comprising Exotoxin of *Pseudomonas aeruginosa* (EPA) that has been modified to contain at least one consensus sequence D/E-X-N-Z-S/T, wherein X and Z may be any natural amino acid except proline; at least one polysaccharide chain linked to the protein carrier and having the following structure:

$$\xrightarrow{\alpha}_{3}\left[\text{L-Rha} \xrightarrow[1,3]{\alpha} \text{L-Rha} \xrightarrow[1,2]{\alpha} \text{D-Gal} \xrightarrow[1,3]{\alpha} \text{D-GlcNAc}\right]_{1} ;$$

and, optionally, an adjuvant.

In yet another aspect, the present invention is directed to a Shigella dysenteriae O1 bioconjugate vaccine comprising: a protein carrier having the sequence provided in SEQ. ID NO.: 7; at least one polysaccharide chain linked to the protein carrier and having the following structure:

$$\xrightarrow{\alpha}_{3}\left[\text{L-Rha} \xrightarrow[1,3]{\alpha} \text{L-Rha} \xrightarrow[1,2]{\alpha} \text{D-Gal} \xrightarrow[1,3]{\alpha} \text{D-GlcNAc}\right]_{1} ;$$

and an adjuvant.

In yet additional aspects, the present invention is directed to: a plasmid comprising SEQ. ID NO. 5; a genetic sequence comprising SEQ. ID NO. 5; an amino acid sequence comprising SEQ. ID NO. 6; an amino acid sequence comprising SEQ. ID NO. 7; or vector pGVXN64.

In another aspect, the present invention is directed to an expression system for producing a bioconjugate vaccine against at least one bacterium comprising: a nucleotide sequence encoding an oligosaccharyl transferase (OST/OTase); a nucleotide sequence encoding a protein carrier; and at least one antigenic polysaccharide synthesis gene cluster from the at least one bacterium, wherein the antigenic polysaccharide is a bacterial O-antigen.

In still another aspect, the present invention is directed to an expression system for producing a bioconjugate vaccine against Shigella dysenteriae O1 comprising: a nucleotide sequence encoding PglB having SEQ. ID NO. 2; a nucleotide sequence encoding a modified EPA having SEQ. ID NO. 6; and a polysaccharide synthesis gene cluster comprising SEQ. ID NO. 5.

In yet another aspect, the present invention contemplates a method of producing an O1-bioconjugate in a bioreactor comprising the steps: expressing in bacteria: modified EPA containing at least one consensus sequence, D/E-X-N-Z-S/T, wherein X and Z may be any natural amino acid except proline, or AcrA; PglB; and one or more O1-polysaccharides; growing the bacteria for a period of time to produce an amount of the O1-bioconjugate comprising the AcrA or the modified EPA linked to the one more O1-polysaccharides; extracting periplasmic proteins; and separating the O1-bioconjugate from the extracted periplasmic proteins.

In an additional aspect, the present invention contemplates a method of producing an S. dysenteriae bioconjugate vaccine, said method comprising: assembling a polysaccharide of S. dysenteriae in a recombinant organism through the use of glycosyltransferases; linking said polysaccharide to an asparagine residue of one or more target proteins in said recombinant organism, wherein said one or more target proteins contain one or more T-cell epitopes.

In a further aspect, the present invention contemplates a method of producing an S. dysenteriae bioconjugate vaccine, said method comprising: introducing genetic information encoding for a metabolic apparatus that carries out N-glycosylation of a target protein into a prokaryotic organism to produce a modified prokaryotic organism, wherein the genetic information required for the expression of one or more recombinant target proteins is introduced into said prokaryotic organism, and wherein the metabolic apparatus comprises specific glycosyltransferases for the assembly of a polysaccharide of S. dysenteriae on a lipid carrier and an oligosaccharyltransferase, the oligosaccharyltransferase covalently linking the polysaccharide to an asparagine residue of the target protein, and the target protein containing at least one T-cell epitope; producing a culture of the modified prokaryotic organism; and obtaining glycosylated proteins from the culture medium.

Figure 4:
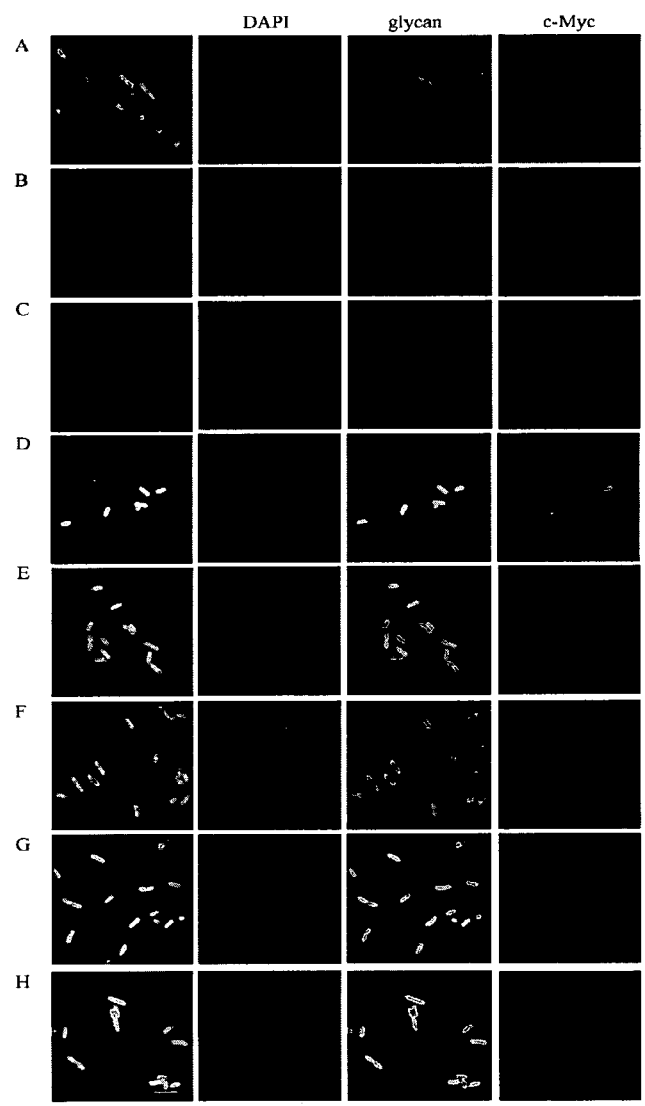

FIG. 4. shows fluorescence microscopy of cells expressing various OmpH1 variants. Fluorescence microscopy was performed by the using an Axioplan2 microscope (Carl Zeiss). Images were combined by using Adobe Photoshop, version CS2. SCM6 cells expressing OmpH1 (panel A), OmpH1$^{N139S}$ (panel B), OmpH1$^{C20S}$ (panel C), OmpH1$^{KGN \rightarrow NIT,HFGDD \rightarrow DSNIT}$ (panel D), OmpH1$^{RGD \rightarrow NIT,HFGDD \rightarrow DSNIT}$ (panel E), OmpH1$^{KGN \rightarrow NIT\ RGD \rightarrow NIT}$ (panel F), OmpH1$^{V83T,KGN \rightarrow NIT}$ (panel G), and OmpH1$^{KGN \rightarrow NIT,RGD \rightarrow NIT,HFGDD \rightarrow DSNIT}$ (panel H). The first column is a merge of the pictures in columns 2, 3, and 4 represented in greytones on black background. Column 2: blue fluorescence in greytones from DAPI stain, column 3: green fluorescence from glycan specific fluorescence, column 4: red fluorescence from anti-myc staining.

Figure 5A:
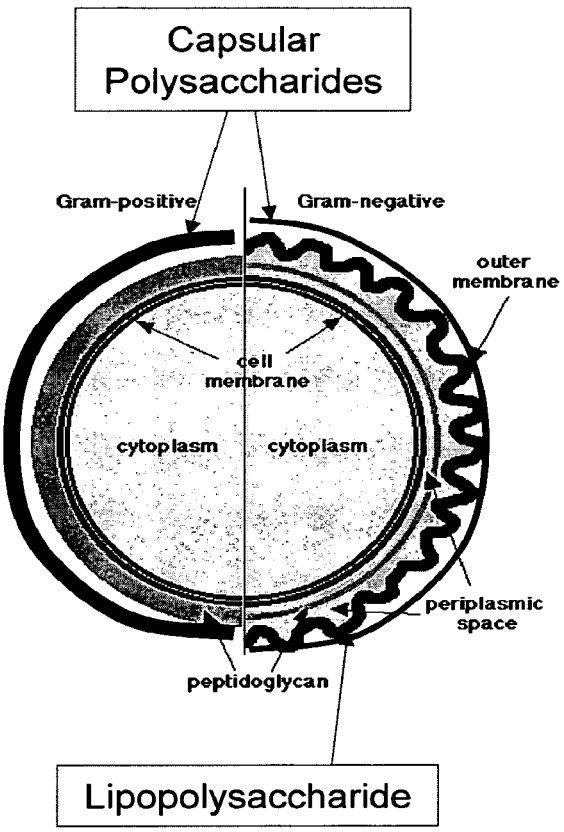

FIG. 5A shows a schematic of the capsular polysaccharides and lipopolysacharides in Gram-positive and Gram-negative bacteria.

Figure 5B:
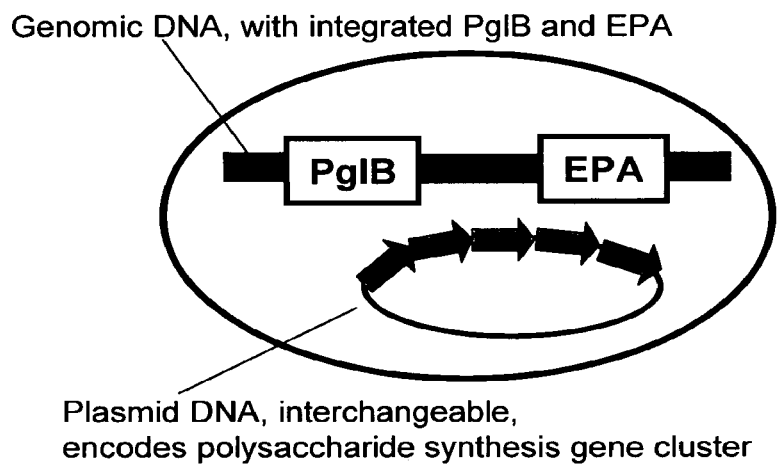

FIG. 5B shows genomic DNA, with integrated PglB and EPA, and plasmid DNA, which is interchangeable (i.e., exchangeable), encoding a polysaccharide synthesis gene cluster.

FIG. 6A shows the production process of conjugate vaccines using technology of the invention.

FIG. 6B shows the construction of the *Shigella dysenteriae* O1 antigen expression plasmid pGVXN64.

Figure 7A:
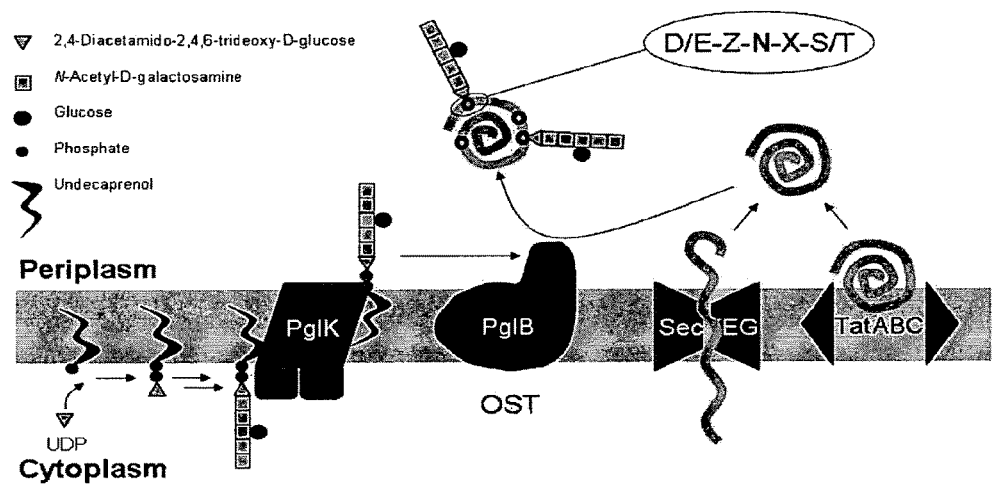
Figure 7B:
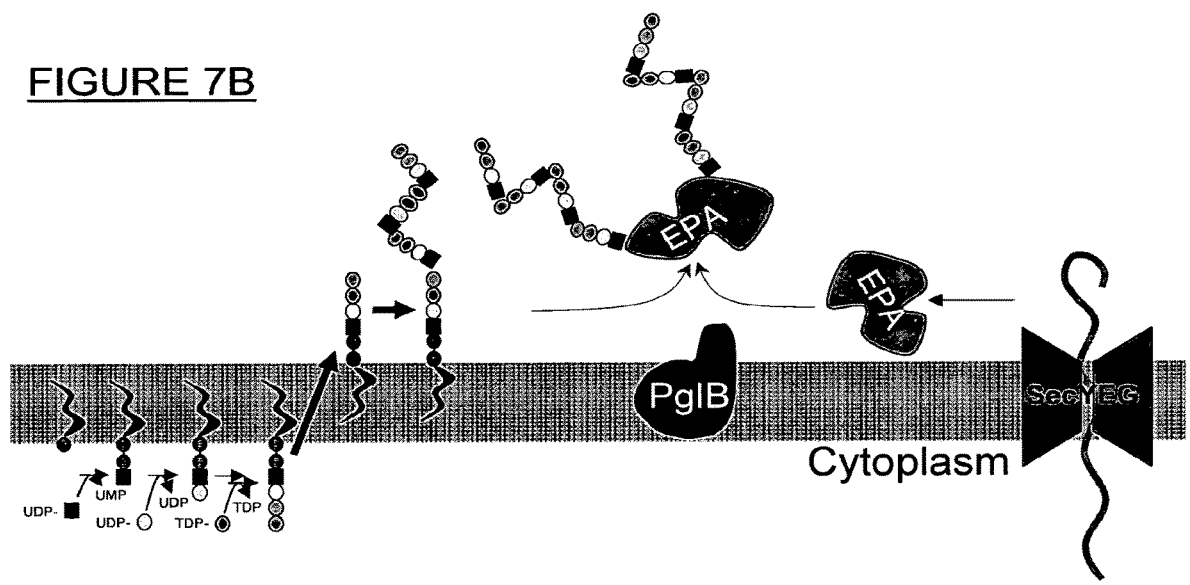

FIGS. 7A and 7B show schematics of the protein glycosylation pathway utilized in the present invention.

Figure 8A:
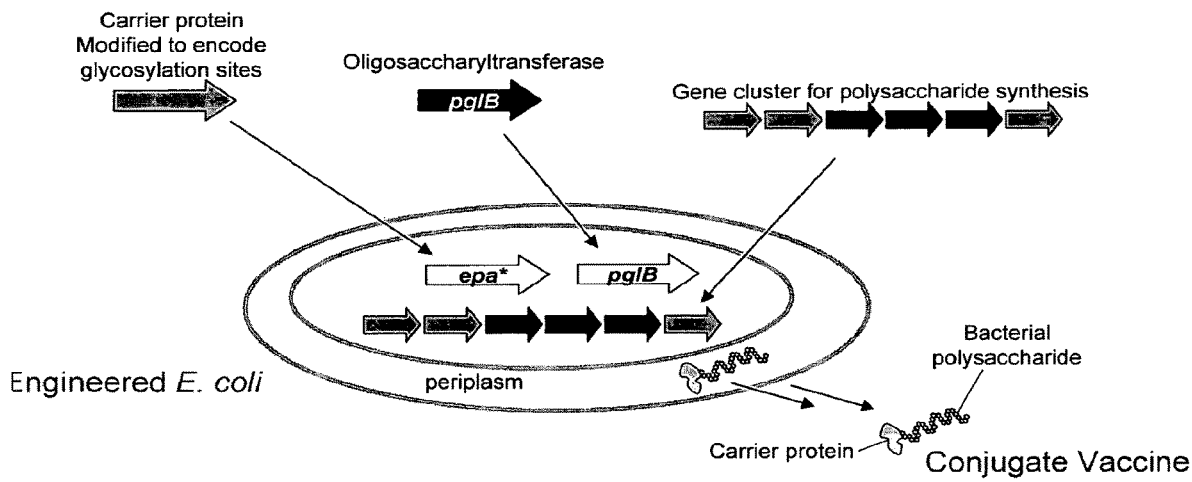
Figure 8B:
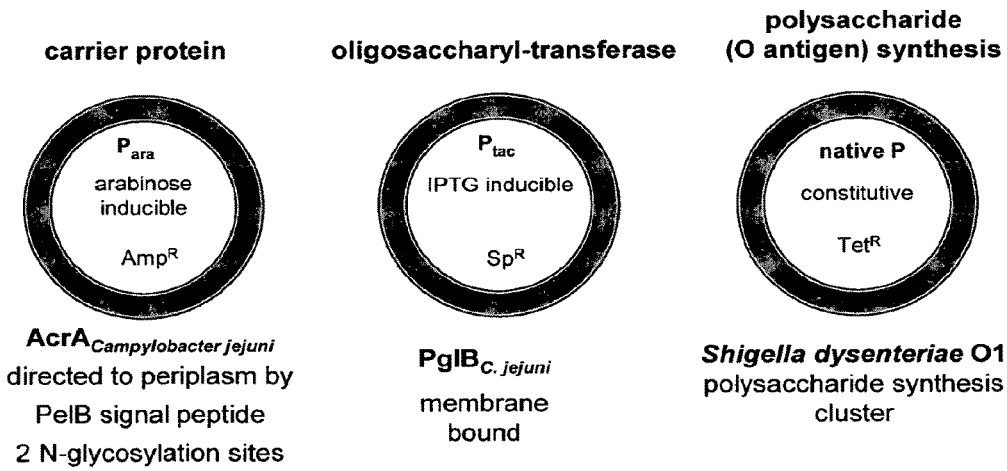

FIGS. 8A and 8B are schematics depicting expression platforms for bioconjugate production of the present invention.

FIG. 9 shows production of *Shigella* bioconjugates.

Figure 10A:
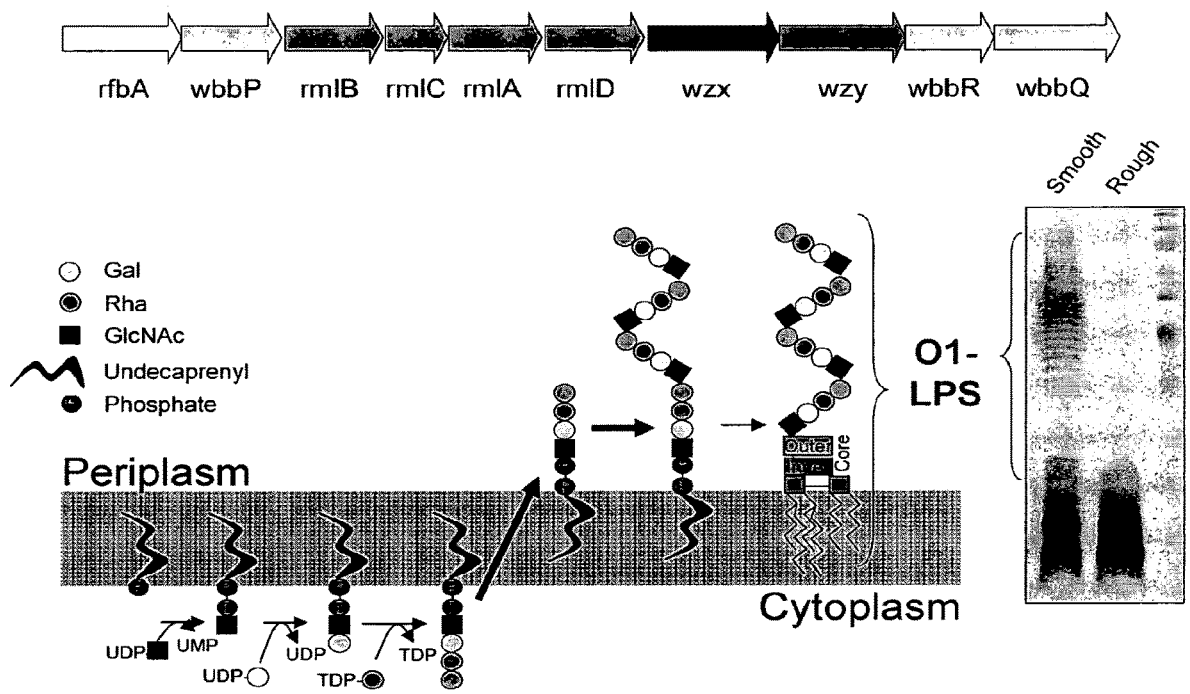

FIG. 10A shows polysaccharide biosynthesis of the O-antigen of *S. dysenteriae* Serotype O1 on undecaprenolpyrophosphate (UPP).

Figure 10B:
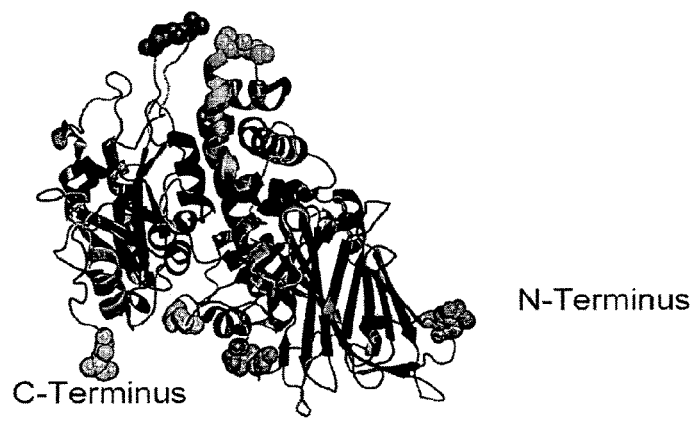

FIG. 10B shows a schematic of a carrier protein, such as EPA, onto which N-glycosylation sites can be designed.

FIG. 11 shows bicoonjugates that elicit an immune response against *Shigella* O1 polysaccharide in mice.

Figure 12:
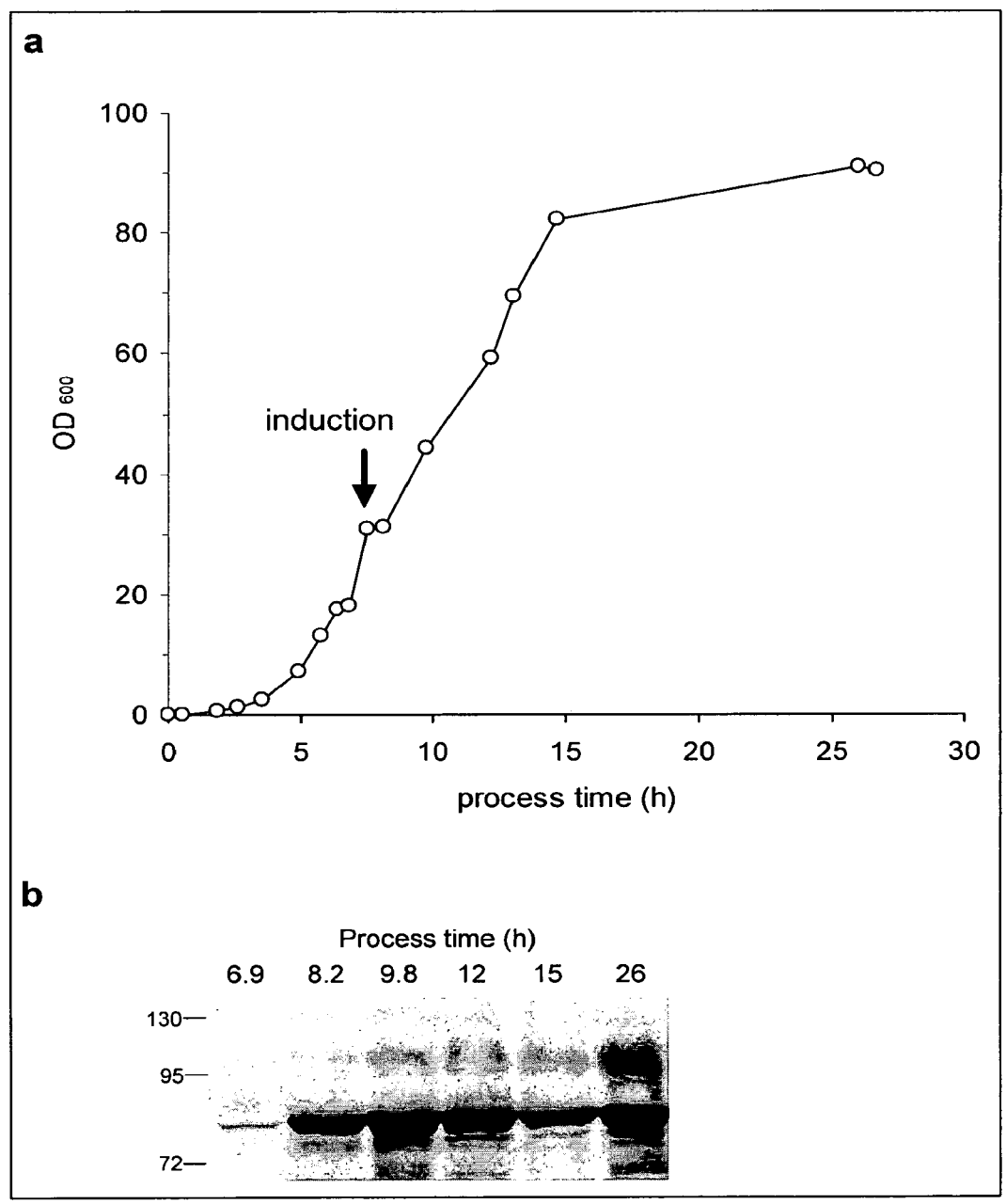

FIG. 12 shows results from the production of a *Shigella* O1-EPA bioconjugate (e.g., O1-EPA) in a bioreactor.

Figure 13:
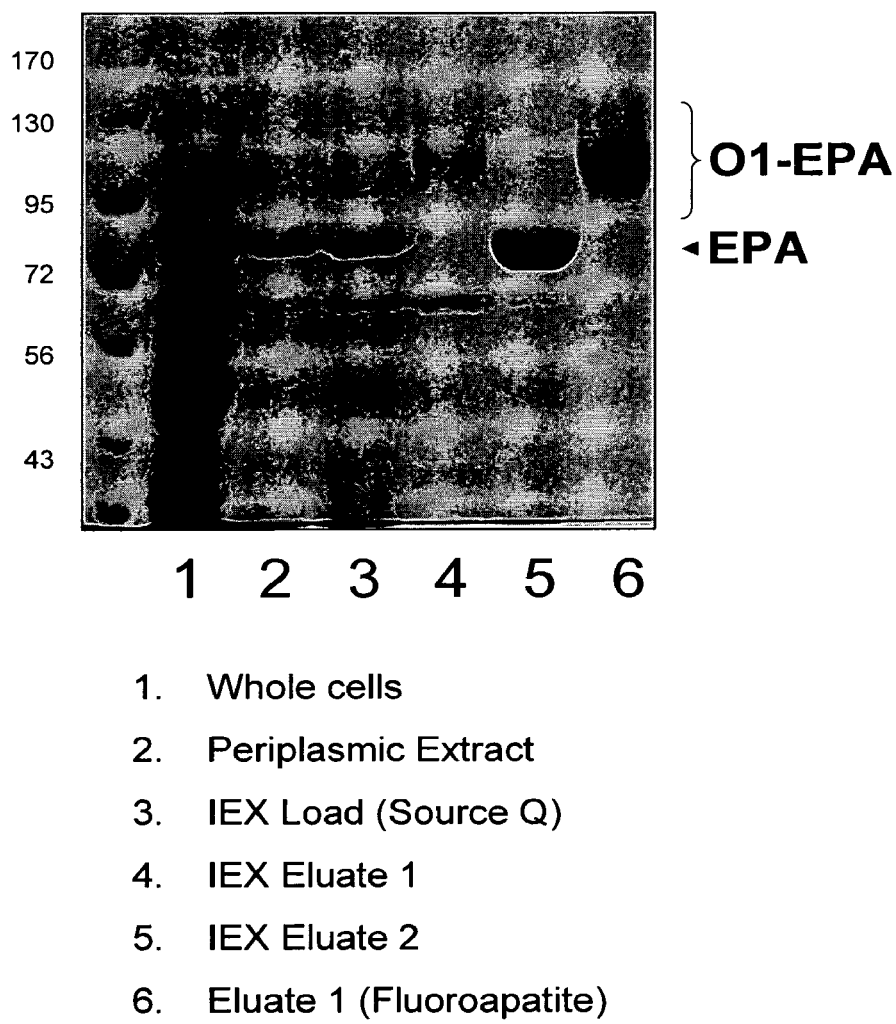

FIG. 13 shows purification of O1-EPA.

Figure 14A:
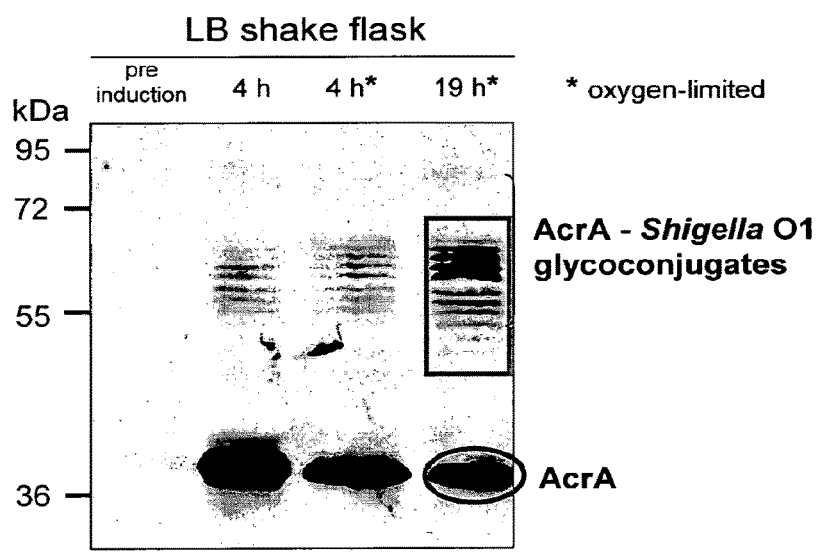

FIG. 14A shows a Western blot analysis of a series of specimens of *Shigella* O1-AcrA bioconjugates produced in an LB shake flask taken under various conditions.

Figure 14B:
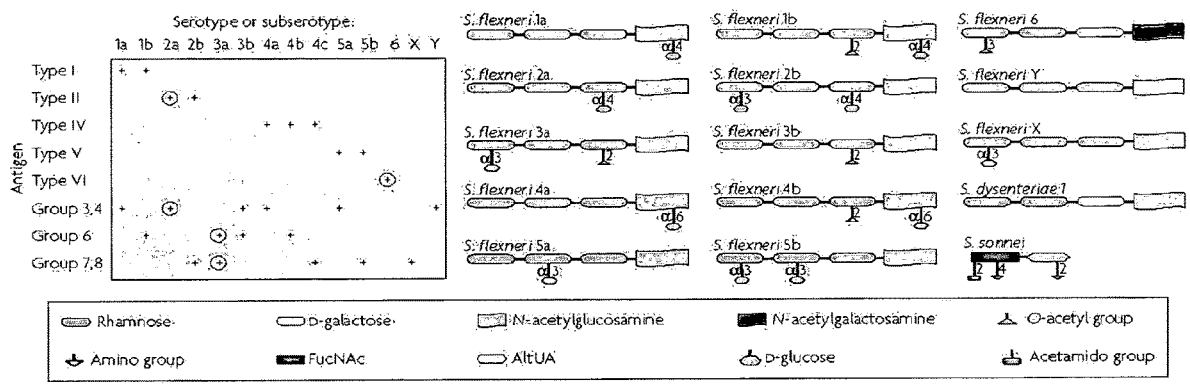

FIG. 14B provides different serotypes of *Shigella* and the polysaccharide structure that defines their antigenicity (i.e., *Shigella* O-antigens).

Figure 15:
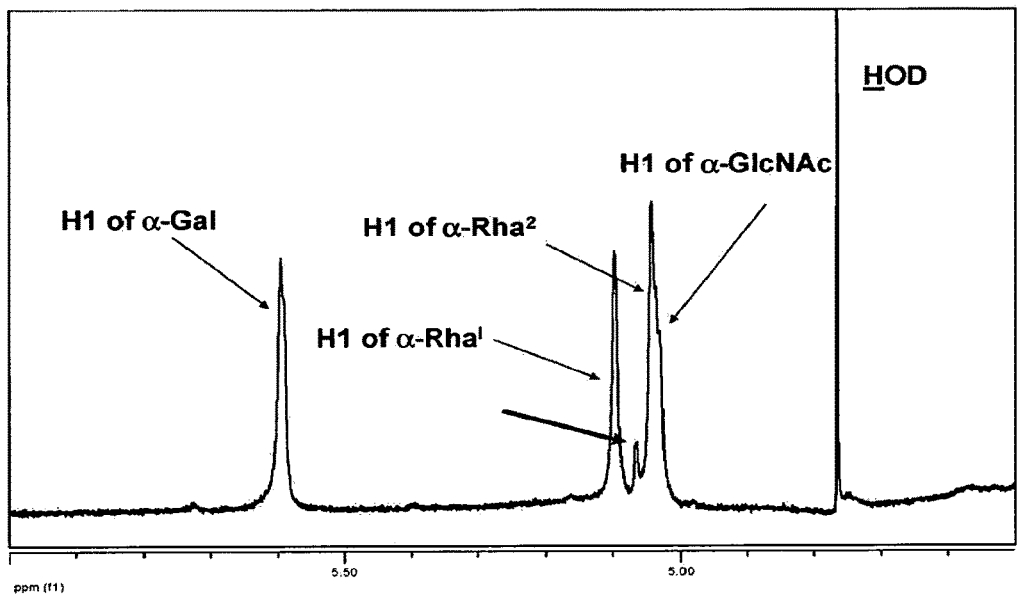

FIG. 15 shows the expansion of the anomeric region of 1H NMR spectrum of an example of a *S. dysenteriae* Serotype O1 bioconjugate of the invention.

Figure 16A:
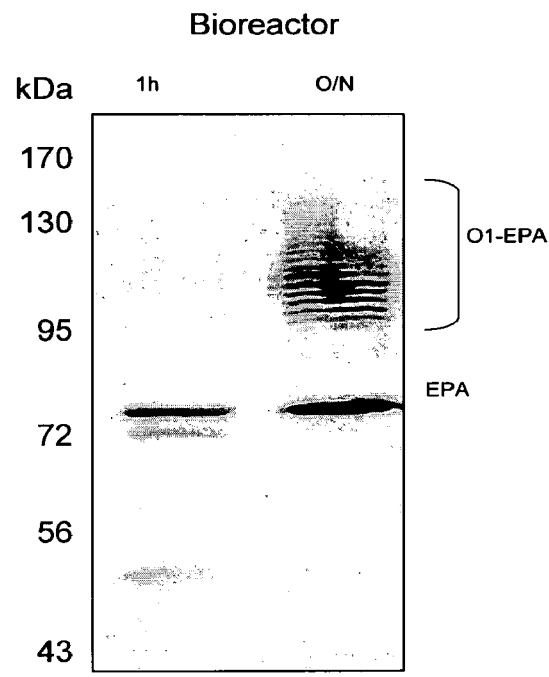

FIG. 16A shows protein samples of a *Shigella* O1 Bioconjugate (e.g., EPA-O1) normalized to biomass concentration (0.1 $OD_{600nm}$ of cells/lane).

Figure 16B:
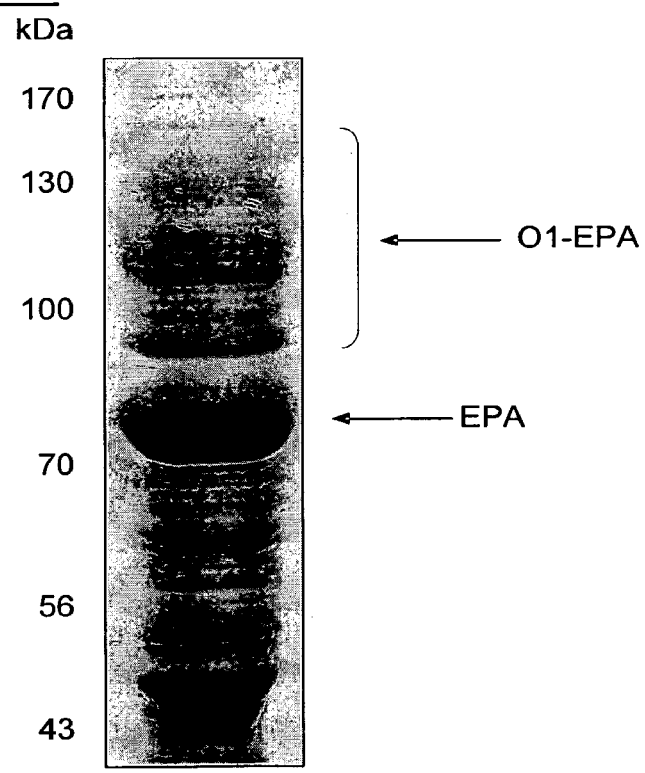

FIG. 16B shows the periplasmic extract from a *Shigella* O1 Bioconjugate production process which was loaded on a 7.5% SDS-PAGE, and stained with Coomasie to identify EPA and EPA-O1.

Figure 17A:
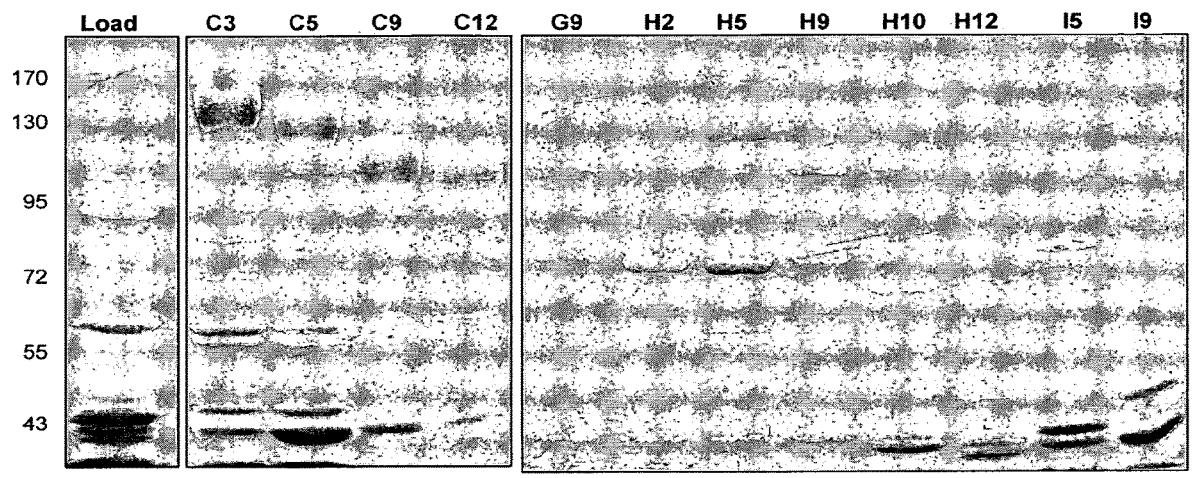

FIG. 17A shows protein fractions from 1. Source Q analyzed by SDS-PAGE and stained by Coomassie to identify the *Shigella* O1 bioconjugate.

Figure 17B:
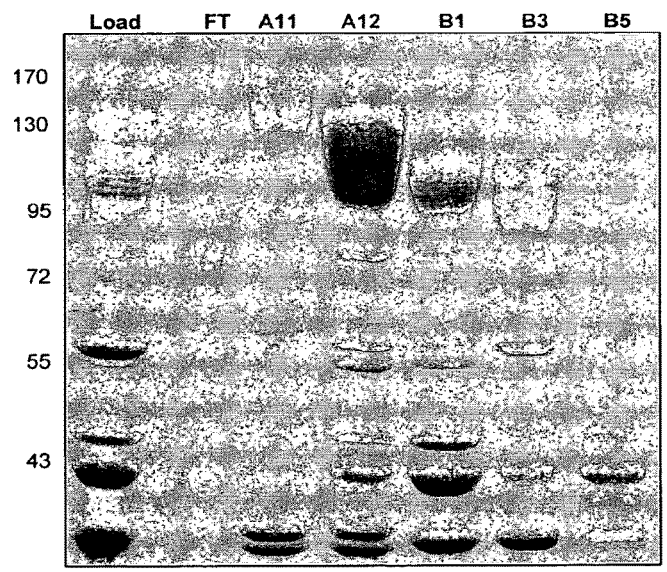

FIG. 17B shows protein fractions from 2. Source Q column analyzed on SDS-PAGE and stained by Coomassie to identify the *Shigella* O1 bioconjugate.

Figure 18A:
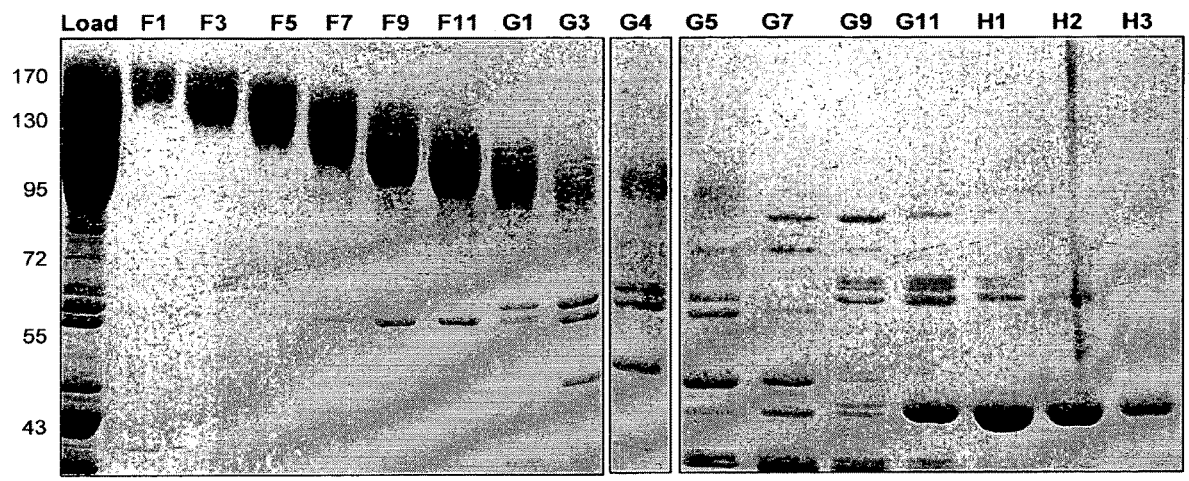

FIG. 18A shows protein fractions from Superdex 200 column analyzed by SDS-PAGE and stained by Coomassie stained to identify the *Shigella* O1 bioconjugate.

Figure 18B:
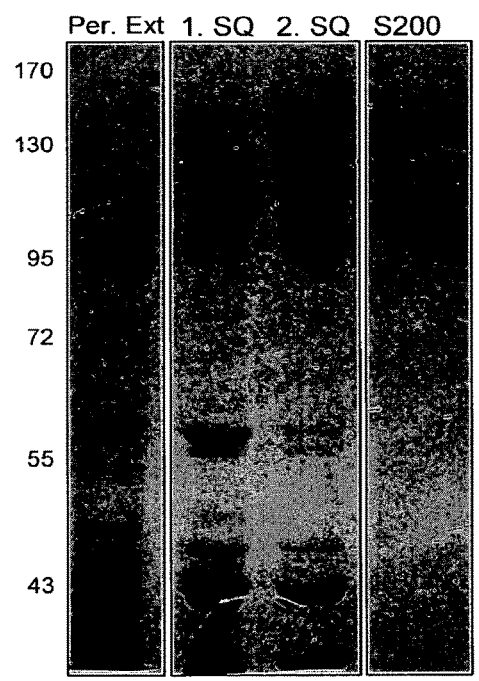

FIG. 18B shows *Shigella* bioconjugates from different purification steps analyzed by SDS-PAGE and stained by Coomassie.

DETAILED DESCRIPTION OF THE INVENTION

Introduction to Invention

The present invention provides a versatile in vivo glycosylation platform.

European Patent Application No. 03 702 276.1 (European Patent 1 481 057) teaches a procaryotic organism into which is introduced a nucleic acid encoding for (i) specific glycosyltransferases for the assembly of an oligosaccharide on a lipid carrier, (ii) a recombinant target protein comprising a consensus sequence "N-X-S/T", wherein X can be any amino acid except proline, and (iii) an oligosaccharyl transferase of *C. jejuni* (OTase) that covalently links said oligosaccharide to the consensus sequence of the target protein. Said procaryotic organism produces N-glycans with a specific structure which is defined by the type of the specific glycosyltransferases.

The known N-glycosylation consensus sequence in a protein allows for the N-glycosylation of recombinant target proteins in procaryotic organisms comprising the oligosaccharyl transferase (OTase) of *C. jejuni*.

The object of the present invention is to provide proteins as well as means and methods for producing such proteins having an optimized efficiency for N-glycosylation that can be produced in procaryotic organisms in vivo. Another object of the present invention aims at the more efficient introduction of N-glycans into recombinant proteins for modifying antigenicity, stability, biological, prophylactic and/or therapeutic activity of said proteins. A further object is the provision of a host cell that efficiently displays recombinant N-glycosylated proteins of the present invention on its surface.

In a first aspect, the present invention provides a recombinant N-glycosylated protein, comprising one or more of the following N-glycosylated optimized amino acid sequence(s):

D/E-X-N-Z-S/T, (optimized consensus sequence)

wherein X and Z may be any natural amino acid except Pro, and wherein at least one of said N-glycosylated partial amino acid sequence(s) is introduced.

It was surprisingly found that the introduction of specific partial amino acid sequence(s) (optimized consensus sequence(s)) into proteins leads to proteins that are efficiently N-glycosylated by the oligosacharyl transferase (OST, OTase) from *Campylobacter* spp., preferably *C. jejuni*, in these introduced positions.

The term "partial amino acid sequence(s)" as it is used in the context of the present invention will also be referred to as "optimized consensus sequence(s)" or "consensus sequence(s)". The optimized consensus sequence is N-glycosylated by the oligosaccharyl transferase (OST, OTase) from *Campylobacter* spp., preferably *C. jejuni*, much more efficiently than the regular consensus sequence "N-X-S\T" known in the prior art.

In general, the term "recombinant N-glycosylated protein" refers to any heterologous poly- or oligopeptide produced in a host cell that does not naturally comprise the nucleic acid encoding said protein. In the context of the present invention, this term refers to a protein produced recombinantly in any host cell, e.g. an eukaryotic or prokaryotic host cell, preferably a procaryotic host cell, e.g. *Escherichia* ssp., *Campylobacter* ssp., *Salmonella* ssp., *Shigella* ssp., *Helicobacter* ssp., *Pseudomonas* ssp., *Bacillus* ssp., more preferably *Escherichia coli*, *Campylobacter jejuni*, *Salmonella typhimurium* etc., wherein the nucleic acid encoding said protein has been introduced into said host cell and wherein the encoded protein is N-glycosylated by the OTase from *Campylobacter* spp., preferably *C. jejuni*, said transferase enzyme naturally occurring in or being introduced recombinantly into said host cell.

In accordance with the internationally accepted one letter code for amino acids the abbreviations D, E, N, S and T denote aspartic acid, glutamic acid, asparagine, serine, and threonine, respectively. Proteins according to the invention differ from natural or prior art proteins in that one or more of the optimized consensus sequence(s) D/E-X-N-Z-S/T is/are introduced and N-glycosylated. Hence, the proteins of the present invention differ from the naturally occurring *C. jejuni* proteins which also contain the optimized consensus sequence but do not comprise any additional (introduced) optimized consensus sequences.

The introduction of the optimized consensus sequence can be accomplished by the addition, deletion and/or substitution of one or more amino acids. The addition, deletion and/or substitution of one or more amino acids for the purpose of introducing the optimized consensus sequence can be accomplished by chemical synthetic strategies well known to those skilled in the art such as solid phase-assisted chemical peptide synthesis. Alternatively, and preferred for larger polypeptides, the proteins of the present invention can be prepared by standard recombinant techniques.

The proteins of the present invention have the advantage that they may be produced with high efficiency and in any procaryotic host comprising a functional pgl operon from *Campylobacter* spp., preferably *C. jejuni*. Preferred alternative OTases from *Campylobacter* spp. for practicing the aspects and embodiments of the present invention are *Campylobacter coli* and *Campylobacter lari* (see Szymanski, C. M. and Wren, B. W. (2005). Protein glycosylation in bacterial mucosal pathogens. Nat. Rev. Microbiol. 3:225-237). The functional pgl operon may be present naturally when said procaryotic host is *Campylobacter* spp., preferably *C. jejuni*. However, as demonstrated before in the art and mentioned above, the pgl operon can be transferred into cells and remain functional in said new cellular environment.

The term "functional pgl operon from *Campylobacter* spp., preferably *C. jejuni*" is meant to refer to the cluster of nucleic acids encoding the functional oligosaccharyl transferase (OTase) of *Campylobacter* spp., preferably *C. jejuni*, and one or more specific glycosyltransferases capable of assembling an oligosaccharide on a lipid carrier, and wherein said oligosaccharide can be transferred from the lipid carrier to the target protein having one or more optimized amino acid sequence(s): D/E-X N-Z-S/T by the OTase. It to be understood that the term "functional pgl operon from *Campylobacter* spp., preferably *C. jejuni*" in the context of this invention does not necessarily refer to an operon as a singular transcriptional unit. The term merely requires the presence of the functional components for N-glycosylation of the recombinant protein in one host cell. These components may be transcribed as one or more separate mRNAs and may be regulated together or separately. For example, the term also encompasses functional components positioned in genomic DNA and plasmid(s) in one host cell. For the purpose of efficiency, it is preferred that all components of the functional pgl operon are regulated and expressed simultaneously.

It is important to realize that only the functional oligosaccharyl transferase (OTase) should originate from *Campylobacter* spp., preferably *C. jejuni*, and that the one or more specific glycosyltransferases capable of assembling an oligosaccharide on a lipid carrier may originate from the host cell or be introduced recombinantly into said host cell, the only functional limitation being that the oligosaccharide assembled by said glycosyltransferases can be transferred from the lipid carrier to the target protein having one or more optimized consensus sequences by the OTase. Hence, the selection of the host cell comprising specific glycosyltransferases naturally and/or incapacitating specific glycosyltransferases naturally present in said host as well as the introduction of heterologous specific glycosyltransferases will enable those skilled in the art to vary the N-glycans bound to the optimized N-glycosylation consensus site in the proteins of the present invention.

As a result of the above, the present invention provides for the individual design of N-glycan-patterns on the proteins of the present invention. The proteins can therefore be individualized in their N-glycan pattern to suit biological, pharmaceutical and purification needs.

In a preferred embodiment, the proteins of the present invention may comprise one but also more than one, preferably at least two, preferably at least 3, more preferably at least 5 of said N-glycosylated optimized amino acid sequences.

The presence of one or more N-glycosylated optimized amino acid sequence(s) in the proteins of the present invention can be of advantage for increasing their antigenicity, increasing their stability, affecting their biological activity, prolonging their biological half-life and/or simplifying their purification.

The optimized consensus sequence may include any amino acid except proline in position(s) X and Z. The term "any amino acids" is meant to encompass common and rare natural amino acids as well as synthetic amino acid derivatives and analogs that will still allow the optimized consensus sequence to be N-glycosylated by the OTase. Naturally occurring common and rare amino acids are preferred for X and Z. X and Z may be the same or different.

It is noted that X and Z may differ for each optimized consensus sequence in a protein according to the present invention.

The N-glycan bound to the optimized consensus sequence will be determined by the specific glycosyltransferases and their interaction when assembling the oligosaccharide on a lipid carrier for transfer by the OTase. Those skilled in the art can design the N-glycan by varying the type(s) and amount of the specific glycosyltransferases present in the desired host cell.

N-glycans are defined herein as monO-, oligO- or polysaccharides of variable compositions that are linked to an ε-amide nitrogen of an asparagine residue in a protein via an N-glycosidic linkage. Preferably, the N-glycans transferred by the OTase are assembled on an undecaprenol-pyrophosphate lipid-anchor that is present in the cytoplasmic membrane of gram-negative or positive bacteria. They are involved in the synthesis of O antigen, O polysaccharide and peptidoglycan (Bugg, T. D., and Brandish, P. E. (1994). From peptidoglycan to glycoproteins: common features of lipid-linked oligosaccharide biosynthesis. FEMS Microbiol Lett 119, 255-262; Valvano, M. A. (2003). Export of O-specific lipopolysaccharide. Front Biosci 8, s452-471).

In a preferred embodiment, the recombinant protein of the present invention comprises one or more N-glycans selected from the group of N-glycans from *Campylobacter* spp., preferably *C. jejuni*, the N-glycans derived from oligO- and polysaccharides transferred to O antigen forming O polysaccharide in Gram-negative bacteria or capsular polysaccharides from Gram-positive bacteria, preferably: *P. aeruginosa* 09, 011; *E. coli* 07, 09, 016, 0157 and *Shigella dysenteriae* O1 and engineered variants thereof obtained by inserting or deleting glycosyltransferases and epimerases affecting the polysaccharide structure.

In a further preferred embodiment, the recombinant protein of the present invention comprises two or more different N-glycans.

For example, different N-glycans on the same protein can prepared by controlling the timing of the expression of specific glycosyltransferases using early or late promoters or introducing factors for starting, silencing, enhancing and/or reducing the promoter activity of individual specific glycosyltransferases. Suitable promoters and factors governing their activity are routinely available to those in the art.

There is no limitation on the origin of the recombinant protein of the invention. Preferably said protein is derived from mammalian, bacterial, viral, fungal or plant proteins. More preferably, the protein is derived from mammalian, most preferably human proteins. For preparing antigenic recombinant proteins according to the invention, preferably for use as active components in vaccines, it is preferred that the recombinant protein is derived from a bacterial, viral or fungal protein.

In a further preferred embodiment, the present invention provides for recombinant proteins wherein either the protein and/or the N-glycan(s) is (are) therapeutically and/or prophylactically active. The introduction of at least one optimized and N-glycosylated consensus sequence can modify or even introduce therapeutic and/or prophylactic activity in a protein. In a more preferred embodiment, it is the protein and/or the N-glycan(s) that is (are) immunogenically active. In this case, the introduced N-glycosylation(s) may have a modifying effect on the proteins biological activity and/or introduce new antigenic sites and/or may mask the protein to evade degrading steps and/or increase the half-life.

The recombinant proteins of the present invention can be efficiently targeted to the outer membrane and/or surface of host cells, preferably bacteria, more preferably gram-negative bacteria. For assisting the surface display and/or outer membrane localization, it is preferred that the recombinant protein of the invention further comprise at least one polypeptide sequence capable of targeting said recombinant protein to the outer membrane and/or cell surface of a bacterium, preferably a gram-negative bacterium.

In a preferred embodiment, the recombinant protein of the invention is one, wherein said targeting polypeptide sequence is selected from the group consisting of type II signal peptides (Paetzel, M., Karla, A., Strynadka, N. C., and Dalbey, R. E. 2002. Signal peptidases. Chem Rev 102: 4549-4580.) or outer membrane proteins (reviewed in Wemerus, H., and Stahl, S. 2004. Biotechnological applications for surface-engineered bacteria. Biotechnol Appl Biochem 40: 209-228.), preferably selected from the group consisting of the full length protein or the signal peptides of OmpH1 from *C. jejuni*, JlpA from *C. jejuni*, outer membrane proteins from *E. coli*, preferably OmpS, OmpC, OmpA, OprF, PhoE, LamB, Lpp'OmpA (a fusion protein for surface display technology, see Francisco, JA$_1$ Earhart, C. F., and Georgiou, G. 1992. Transport and anchoring of beta-lactamase to the external surface of *Escherichia coli*. Proc Natl Acad Sci USA 89: 2713-2717.), and the Inp protein from *Pseudomonas aeruginosa*.

In a different aspect, the present invention relates to a nucleic acid encoding a recombinant protein according to the invention. Preferably, said nucleic acid is a mRNA, a DNA or a PNA, more preferably a mRNA or a DNA, most preferably a DNA. The nucleic acid may comprise the sequence coding for said protein and, in addition, other sequences such as regulatory sequences, e.g. promoters, enhancers, stop codons, start codons and genes required to regulate the expression of the recombinant protein via the mentioned regulatory sequences, etc. The term "nucleic acid encoding a recombinant protein according to the invention" is directed to a nucleic acid comprising said coding sequence and optionally any further nucleic acid sequences regardless of the sequence information as long as the nucleic acid is capable of producing the recombinant protein of the invention in a host cell containing a functional pgl operon from *Campylobacter* spp., preferably *C. jejuni*. More preferably, the present invention provides isolated and purified nucleic acids operably linked to a promoter, preferably linked to a promoter selected from the group consisting of known inducible and constitutive prokaryotic promoters, more preferably the tetracycline promoter, the arabinose promoter, the salicylate promoter, lac-, trc-, and lac promotors (Baneyx, F. (1999). Recombinant protein expression in *Escherichia coli*. Curr Opin Biotechnol 10, 411-421; Billman-Jacobe, H. (1996). Expression in bacteria other than *Escherichia coli*. Curr Opin Biotechnol 7, 500-504.). Said operably linked nucleic acids can be used for, e.g. vaccination.

Furthermore, another aspect of the present invention relates to a host cell comprising a nucleic acid and/or a vector according to the present invention. The type of host cell is not limiting as long as it accommodates a functional pgl operon from *C. jejuni* and one or more nucleic acids coding for recombinant target protein(s) of the present invention. Preferred host cells are prokaryotic host cells, more preferably bacteria, most preferably those selected from the group consisting of *Escherichia* ssp., *Campylobacter* ssp., *Salmonella* ssp., *Shigella* ssp., *Helicobacter* ssp., *Pseudomonas* ssp., *Bacillus* ssp., preferably *Escherichia coli*, more preferably *E. coli* strains Top10, W3110, CLM24, BL21, SCM6 and SCM7 (Feldman et al., (2005). Engineering N-linked protein glycosylation with diverse O antigen lipopolysaccharide structures in *Escherichia coli*. Proc. Natl. Acad. Sci. USA 102, 3016-3021; Alaimo, C, Catrein, I., Morf, L., Marolda, C. L., Callewaert, N., Valvano, M. A., Feldman, M. F., Aebi, M. (2006). Two distinct but interchangeable mechanisms for flipping of lipid-linked oligosaccharides. EMBO Journal 25, 967-976) and *S. enterica* strains SL3261 (*Salmonella enterica* sv. *Typhimu-*

*rium* LT2 (delta) aroA, see Hoiseth, S. K., and Stocker, B. A. 1981, Aromatic-dependent *Salmonella typhimurium* are non-virulent and effective as live vaccines. Nature 291:238-239), SL3749 (*Salmonella enterica* sv. *Typhimurium* LT2 waaL, see Kaniuk et al., J. Biol. Chem. 279: 36470-36480) and SL3261 ΔwaaL.

In a more preferred embodiment, the host cell according to the invention is one that is useful for the targeting to the outer membrane and/or surface display of recombinant proteins according to the invention, preferably one, wherein said host cell is a recombinant gram-negative bacterium having:
i) a genotype comprising nucleotide sequences encoding for
  a) at least one natural or recombinant specific glycosyltransferase for the assembly of an oligosaccharide on a lipid carrier,
  b) at least one natural or recombinant prokaryotic oligosaccharyl transferase (OTase) from *Campylobacter* spp., preferably *C. jejuni*,
  c) at least one recombinant protein according to the invention, preferably a protein further comprising a targeting polypeptide, and
ii) a phenotype comprising a recombinant N-glycosylated protein according to the invention that is located in and/or on the outer membrane of the gram-negative bacterium.

The host cell for the above embodiment is preferably selected from the group consisting of *Escherichia* ssp., *Campylobacter* ssp., *Shigella* ssp, *Helicobacter* ssp. and *Pseudomonas* ssp., *Salmonella* ssp., preferably *E. coli*, more preferably *E. coli* strains Top10, W3110, CLM24, BL21, SCM6 and SCM7, and *S. enterica* strains SL3261, SL3749 and SL326iδwaaL (see Hoiseth, S. K., and Stocker, B. A. 1981. Aromatic-dependent *Salmonella typhimurium* are non-virulent and effective as live vaccines. Nature 291: 238-239), SL3749 (Kaniuk, N. A., Vinogradov, E., and Whitfield, C. 2004. Investigation of the structural requirements in the lipopolysaccharide core acceptor for ligation of O antigens in the genus *Salmonella*: WaaL "ligase" is not the sole determinant of acceptor specificity. J Biol Chem 279: 36470-36480).

Because preferred proteins of the present invention may have a therapeutic or prophylactic activity by themselves and/or due to the introduced N-glycosylation sites, they can be used for the preparation of a medicament. The type of protein for practicing the invention is not limited and, therefore, proteins of the invention such as EPO, IFN-alpha, TNFalpha, IgG, IgM, IgA, interleukins, cytokines, viral and bacterial proteins for vaccination like *C. jejuni* proteins such as HisJ (CjO734c), AcrA (CjO367c), OmpH1 (CjO982c), Diphteria toxin (CRM 197), Cholera toxin, *P. aeruginosa* exoprotein, to name just a few, and having introduced therein the optimized N-glycosylated consensus sequence are useful for preparing a medicament (Wyszynska, A., Raczko, A., Lis, M., and Jagusztyn-Krynicka, E. K. (2004). Oral immunization of chickens with avirulent *Salmonella* vaccine strain carrying *C. jejuni* 72Dz/92 cjaA gene elicits specific humoral immune response associated with protection against challenge with wild-type *Campylobacter*. Vaccine 22, 1379-1389).

In addition, the nucleic acids and/or vectors according to the invention are also useful for the preparation of a medicament, preferably for use in gene therapy.

Moreover, a host cell according to the invention, preferably one that has a phenotype comprising an N-glycosylated recombinant protein of the invention that is located in and/or on the outer membrane of a bacterium, preferably a gram-negative bacterium, more preferably one of the above-listed gram-negative bacteria, is particularly useful for the preparation of a medicament.

More preferably, a protein of the invention is used for the preparation of a medicament for the therapeutic and/or prophylactic vaccination of a subject in need thereof.

In a more preferred embodiment, the present invention relates to the use of a nucleic acid and/or a vector according to the invention for the preparation of a medicament for the therapeutic and/or prophylactic vaccination of a subject in need thereof, preferably by gene therapy.

The host cells of the invention displaying said N-glycosylated recombinant proteins are particularly useful for preparing vaccines, because the displayed N-glycosylated proteins are abundantly present on the host cell's surface and well accessible by immune cells, in particular their hydrophilic N-glycans, and because the host cells have the added effect of an adjuvant, that, if alive, may even replicate to some extent and amplify its vaccination effects.

Preferably, the host cell for practicing the medical aspects of this invention is an attenuated or killed host cell.

Another advantage of the use of the inventive host cells for preparing medicaments, preferably vaccines, is that they induce IgA antibodies due to the cellular component.

Preferably, said host cells are used according to the invention for inducing IgA antibodies in an animal, preferably a mammal, a rodent, ovine, equine, canine, bovine or a human. It is preferred that said subject in need of vaccination is avian, mammalian or fish, preferably mammalian, more preferably a mammal selected from the group consisting of cattle, sheep, equines, dogs, cats, and humans, most preferably humans. Fowls are also preferred.

A further aspect of the present invention relates to a pharmaceutical composition, comprising at least one protein, at least one nucleic acid, a least one vector and/or at least one host cell according to the invention. The preparation of medicaments comprising proteins or host cells, preferably attenuated or killed host cells, and the preparation of medicaments comprising nucleic acids and/or vectors for gene therapy are well known in the art. The preparation scheme for the final pharmaceutical composition and the mode and details of its administration will depend on the protein, the host cell, the nucleic acid and/or the vector employed.

In a preferred embodiment, the pharmaceutical composition of the invention comprises a pharmaceutically acceptable excipient, diluent and/or adjuvant.

The present invention provides for a pharmaceutical composition comprising at least one of the following, (i) a recombinant protein, a host cell, a nucleic acid and/or a recombinant vector being/encoding/expressing a recombinant protein according to the present invention, and (ii) a pharmaceutically acceptable excipient, diluent and/or adjuvant.

Suitable excipients, diluents and/or adjuvants are well-known in the art. An excipient or diluent may be a solid, semi-solid or liquid material which may serve as a vehicle or medium for the active ingredient. One of ordinary skill in the art in the field of preparing compositions can readily select the proper form and mode of administration depending upon the particular characteristics of the product selected, the disease or condition to be treated, the stage of the disease or condition, and other relevant circumstances (Remington's Pharmaceutical Sciences, Mack Publishing Co. (1990)). The proportion and nature of the pharmaceutically acceptable diluent or excipient are determined by the solubility and chemical properties of the pharmaceutically active compound selected, the chosen route of administration, and standard pharmaceutical practice. The pharmaceutical preparation may be adapted for oral, parenteral or topical use and may be administered to the patient in the form of tablets, capsules, suppositories, solution, suspensions, or the like. The pharmaceutically active compounds of the present invention, while effective themselves, can be formulated and administered in the form of their pharmaceutically acceptable salts, such as acid addition salts or base addition salts, for purposes of stability, convenience of crystallization, increased solubility, and the like.

A further aspect of the present invention is directed to a method for producing N-linked glycosylated proteins, comprising the steps of:
a) providing a recombinant organism, preferably a prokaryotic organism, comprising nucleic acids coding for
   i) a functional pgl operon from *Campylobacter* spp., preferably *C. jejuni*, and
   ii) at least one recombinant target protein comprising one or more of the following N-glycosylated optimized amino acid consensus sequence(s):

D/E-X-N-Z-S/T, wherein X and Z may be any natural amino acid except Pro, and wherein at least one of said N-glycosylated optimized amino acid consensus sequence(s) is introduced, and
b) culturing the recombinant organism in a manner suitable for the production and N-glycosylation of the target protein(s).

Preferably, the target protein is one of the above described recombinant proteins according to the invention.

In a preferred method of the invention, the functional pgl operon from *Campylobacter* spp., preferably *C. jejuni*, comprises nucleic acids coding for
   i) recombinant OTase from *Campylobacter* spp., preferably *C. jejuni*, and
   ii) recombinant and/or natural specific glycosyltransferases from *Campylobacter* spp., preferably *C. jejuni*, and/or
   iii) recombinant and/or natural specific glycosyltransferases from species other than *Campylobacter* spp., for the assembly of an oligosaccharide on a lipid carrier to be transferred to the target protein by the OTase.

Moreover, in a preferred embodiment the present invention relates to a method for preparing a host cell according to the invention comprising the steps of:
i) providing a gram-negative bacterium,
ii) introducing into said bacterium at least one nucleotide sequence encoding for
   a) at least one recombinant specific glycosyltransferase for the assembly of an oligosaccharide on a lipid carrier, and/or
   b) at least one recombinant oligosaccharyl transferase (OTase) from *Campylobacter* spp., preferably *C. jejuni*, and/or
   c) at least one recombinant protein comprising one or more of the following N-glycosylated optimized amino acid consensus sequence(s):

D/E-X-N-Z-S/T, wherein X and Z may be any natural amino acid except Pro, and wherein at least one of said N-glycosylated optimized amino acid consensus sequence(s) is introduced, and iii) culturing said bacterium until at least one recombinant N-glycosylated protein coded by the nucleotide sequence of c) is located in and/or on the outer membrane of the gram-negative bacterium.

For practicing the preferred methods above, the recombinant procaryotic organism or host cell is preferably selected from the group of bacteria consisting of *Escherichia* ssp., *Campylobacter* ssp., *Salmonella* ssp., *Shigella* ssp., *Helicobacter* ssp., *Pseudomonas* ssp., *Bacillus* ssp., preferably *Escherichia coli*, preferably *E. coli* strains Top 10, W3110, W3110ΔwaaL, BL21, SCM6 and SCM7, and *S. enterica* strains SL3261, SL3749 and SL3261 ΔwaaL.

Another preferred method for producing, isolating and/or purifying a recombinant protein according to the invention comprises the steps of:
a) culturing a host cell,
b) removing the outer membrane of said recombinant gram-negative bacterium; and
c) recovering said recombinant protein.

Exemplary methods for removing the outer membrane of a cell, preferably a prokaryotic cell, more preferably a gram-negative bacterial cell, are suitable enzymatic treatment methods, osmotic shock detergent solubilisation and the French press method.

Most preferred, the present invention relates to a method, wherein recombinant or natural specific glycosyltransferases from species other than *Campylobacter* spp., preferably *C. jejuni*, are selected from the group of glycosyltransferases and epimerases originating from bacteria, archea, and/or eukaryota that can be functionally expressed in said host cell.

Bioconjugate Vaccines

An embodiment of the invention involves novel bioconjugate vaccines. A further embodiment of the invention involves a novel approach for producing such bioconjugate vaccines that uses recombinant bacterial cells that directly produce immunogenic or antigenic bioconjugates. In one embodiment, bioconjugate vaccines can be used to treat or prevent bacterial diseases, such as diarrhea, nosocomial infections and meningitis. In further embodiments, bioocon-jugate vaccines may have therapeutic and/or prophylactic potential for cancer or other diseases.

Conjugate vaccines can be administered to children to protect against bacterial infections and can provide a long lasting immune response to adults. Constructs of the invention have been found to generate an IgG response in animals. It has been found that an IgG response to a *Shigella* O-specific polysaccharide-protein conjugate vaccine in humans correllates with immune protection in humans. (Passwell, J. H. et al., "Safety and Immunogenicity of Improved *Shigella* O-Specific Polysaccharide-Protein Conjugate Vaccines in Adults in Israel" Infection and Immunity, 69(3):1351-1357 (March 2001).) It is believed that the polysaccharide (i.e. sugar residue) triggers a short-term immune response that is sugar-specific. Indeed, the human immune system generates a strong response to specific polysaccharide surface structures of bacteria, such as O-antigens and capular polysaccharides. However, since the immune response to polysaccharides is IgM dependent, the immune system develops no memory. The protein carrier that carries the polysaccharide triggers an IgG response that is T-cell dependent and that provides long lasting protection since the immune system develops memory.

A typical vaccination dosage for humans is about 1 to 25 μg, preferably about 1 μg to about 10 μg, most preferably about 10 μg. Optionally, a vaccine, such as a bioconjugate vaccine of the present invention, includes an adjuvant.

Synthesized complexes of polysaccharides (i.e., sugar residues) and proteins (i.e., protein carriers) can be used as conjugate vaccines to protect against a number of bacterial infections. In one aspect, the instant invention is directed to a novel bioengineering approach for producing immunogenic conjugate vaccines that provide advantages over classical chemical conjugation methods. In one embodiment, the approach involves in vivo production of glycoproteins in bacterial cells, for example, Gram-negative cells such as *E. coli*.

The biosynthesis of different polysaccharides is conserved in bacterial cells. The polysaccharides are assembled on carrier lipids from common precursors (activated sugar nucleotides) at the cytoplasmic membrane by different glycosyltransferases with defined specificity. Lipopolysaccharides (LPS) are provided in gram-negative bacteria only, e.g. *Shigella* spp., *Pseudomonas* spp. and *E. coli* (ExPEC, EHEC).

The synthesis of lipopolysaccharides (LPS) starts with the addition of a monosaccharide to the carrier lipid undecaprenyl phosphate at the cytoplasmic side of the membrane. The antigen is built up by sequential addition of monosaccharides from activated sugar nucleotides by different glycosyltransferases and the lipid-linked polysaccharide is flipped through the membrane by a flippase. The antigen-repeating unit is polymerized by an enzymatic reaction. The polysaccharide is then transferred to the Lipid A by the Ligase WaaL forming the LPS that is exported to the surface, whereas the capsular polysaccharide is released from the carrier lipid after polymerization and exported to the surface. The biosynthetic pathway of these polysaccharides enables the production of LPS bioconjugates in vivo, capturing the polysaccharides in the periplasm to a protein carrier. Bioconjugates, such as LPS bioconjugates, are preferred in the present invention.

As shown in FIG. 5A, both Gram-positive and Gram-negative bacteria have a cell membrane that is surrounded by capsular polysaccharides. Gram-negative bacteria additionally have an outer membrane over the cell membrane, with a periplasmic space separating the two membranes. In addition, they contain lipopolysacharides at the surface. When Gram-negative bacteria, such as *E. coli*, is used to produce a conjugate vaccine of the present invention, the glycoprotein used in the conjugate vaccine is assembled in the periplasmic space.

Conjugate vaccines have been successfully used to protect against bacterial infections. The conjugation of an antigenic polysaccharide to a protein carrier is required for protective memory response, as polysaccharides are T-cell independent antigens. Polysaccharides have been conjugated to protein carriers by different chemical methods, using activation reactive groups in the polysaccharide as well as the protein carrier.

FIG. 6A shows the production process of conjugate vaccines using technology of the invention compared to the currently used process. Currently, conjugate vaccines are produced using two fermentation runs and after several purification and chemical cleavage steps, as schematically shown in the top panel. This current approach has a number of problems. First, large scale cultivation of pathogenic organisms is required. Second, the conjugation approach is dependent on the polysaccharide. Third, the approach has low reproducibility. Fourth, the approach has low homogeneity due to unspecific conjugation. Fifth, the approach also has low purity due to excess of polysaccharide in conjugation. Finally, the current approach provides yields of less than 20%.

As shown in the bottom panel of FIG. 6A, in an embodiment, the innovative technology of the invention can be used to develop conjugate vaccines (e.g., bioconjugate vaccines) completely in vivo with non-pathogenic cells, avoiding chemical reactions and providing high purity after a few purification steps. This novel method also allows for the production of bioconjugate vaccines that are not feasible using current methods. Moreover, the conjugation and purification process is independent of the polysaccharide antigen that is used. As a result, bioconjugate vaccines can be engineered faster using novel glycan structures. The increased homogeneity of resulting conjugates and the improved reproducibility (i.e., no batch to batch variability) of such conjugates makes this a highly attractive process from quality control and regulatory perspectives. In addition, the novel method provides good yield (30-60 mg/L and up to 200 mg/L).

The present invention is directed to a novel conjugation process involving engineering bacterial cells to produce the final bioconjugate vaccines. One embodiment of the invention allows the production of bioconjugate vaccines in vivo, circumventing the chemical conjugation and therefore simplifying the production process. The technology includes a novel genetic/enzymatic mechanism for the in vivo synthesis of novel bioconjugates consisting of protein-linked saccharides.

The basis of one aspect of the invention includes the discovery that *Campylobacter jejuni* contains a general N-linked protein glycosylation system, an unusual feature for prokaryotic organisms. Various proteins of *C. jejuni* have been shown to be modified by a heptasaccharide. This heptasaccharide is assembled on undecaprenyl pyrophosphate, the carrier lipid, at the cytoplasmic side of the inner membrane by the stepwise addition of nucleotide activated monosaccharides catalyzed by specific glycosyltransferases. The lipid-linked oligosaccharide then flip-flops (diffuses transversely) into the periplasmic space by a flipppase, e.g., PglK. In the final step of N-linked protein glycosylation, the oligosaccharyltransferase (e.g., PglB) catalyzes the transfer of the oligosaccharide from the carrier lipid to Asn residues within the consensus sequence Asp/Glu-Xaa-Asn-Zaa-Ser/Thr (i.e., D/E-X-N-Z-S/T), where the Xaa and Zaa can be any amino acid except Pro (FIG. 7A). We have successfully transferred the glycosylation cluster for the heptasaccharide into *E. coli* and were able to produce N-linked glycoproteins of *Campylobacter*.

We have been able to demonstrate that PglB does not have a strict specificity for the lipid-linked sugar substrate. The antigenic polysaccharides assembled on undecaprenyl pyrophosphate are captured by PglB in the periplasm and transferred to a protein carrier (Feldman, 2005; Wacker, M., et al., Substrate specificity of bacterial oligosaccharyltransferase suggests a common transfer mechanism for the bacterial and eukaryotic systems. Proc Natl Acad Sci USA, 2006. 103 (18): p. 7088-93.) The enzyme will also transfer a diverse array of undecaprenyl pyrophosphate (UPP) linked oligosaccharides if they contain an N-acetylated hexosamine at the reducing terminus. The nucleotide sequence for pglB is provided at SEQ. ID NO. 1, whereas the amino acid sequence for PglB is provided at SEQ. ID NO. 2.

FIGS. 7A and 7B show schematics of the protein glycosylation pathway (i.e., N-glycosylation system) of the present invention. In an embodiment, the protein glycosylation pathway of *C. jejuni* (e.g., including pgl operon) can be introduced into *E. coli*. In FIG. 7A, an oligosaccharide, specifically a heptasaccharide made of five N-acetyl-D-galactosamine units, one glucose unit and one 2,4-diacetamidO-2,4,6-trideoxy-D-glucose unit, is assembled onto a lipid carrier, undecaprenylpyrophosphate (UDP), using glycosyltransferases (e.g., pglA, pglC, pglH, J; I) at the cytoplasmic side of the inner membrane and is transferred to the periplasmic space by way of a flippase called PgIK. Separately, a carrier protein depicted as a spiral and containing consensus sequence D/E-X-N-Z-S/T (i.e., Asp/Glu-Xaa-Asn-Zaa-Ser/Thr) is translated in the cytoplasm and is secreted into the periplasmic space. In the final step, an oligosaccharyl transferase (OST or OTase) (e.g., PgIB) transfers the heptasaccharide to Asn residues within a consensus sequence of the carrier protein to produce a glycoprotein.

FIG. 7B also shows biosynthesis of a polysaccharide (i.e., an antigenic polysaccharide or antigen) by stepwise action of glycosyltransferases, and transfer of the O-antigen to the periplasm by way of flippase, followed by polymerization into a polysaccharide using a polymerase (e.g., wzy). Separately, a carrier protein, such as EPA, is produced and secreted into the periplasm. An oligosaccharyl transferase (OST or OTase), such as PgIB, has relaxed substrate specificity and transfers the polysaccharide from a lipid carrier to Asn in the consensus sequence within EPA.

FIG. 8A shows a schematic depicting an embodiment of the expression platform for bioconjugate production of the present invention. The technology of the invention is versatile in that various existing carrier proteins can be employed, so long as the carrier protein contains or is modified to contain the consensus sequence, as discussed earlier. In particular, FIG. 8A illustrates the construction of an expression host, such as an engineered *E. coli* bacterium in an embodiment of the invention. Such an *E. coli* contains the general components of a glycosylation system (i.e., an OST/OTase, e.g., PgIB, and a protein carrier, e.g. EPA). Such components can be integrated into the genome of an *E. coli* strain. In addition, the Ligase WaaL as well as WecG are deleted. Additionally, specific components for polysaccharide antigen expression (i.e., a polysaccharide synthesis gene cluster containing, for example, glycosyl transferase, polymerase, flippase, and sugar biosynthesis enzymes) can be provided by the addition of an exchangeable plasmid. This construction allows for specific glycosylation of the protein carrier with a polysaccharide of choice in vivo.

In an embodiment of the expression system for a bacterial bioconjugate that is compatible with Good Manufacturing Practices (GMP), DNA encoding the inducible oligosaccharyltransferase and carrier protein can be stably integrated into a bacterial (e.g., *E. coli*) genome such that genes for antibiotic selection can be omitted. For example, as shown in FIG. 5B, PgIB and EPA is integrated into genomic DNA, whereas plasmid DNA, which is interchangeable (i.e., exchangeable), encodes a polysaccharide synthesis gene cluster.

In another embodiment, FIG. 8B shows an expression system for a bacterial bioconjugate that includes three plasmids. A first plasmid codes for the carrier protein, e.g., AcrA from *Campylobacter jejuni*, which has two N-glycosylation sites and is directed to the periplasm by a PelB signal peptide. A second plasmid codes for the OST/OTase, e.g., PgIB from *C. jejuni*, which is membrane-bound. A third plasmid is a native plasmid that codes, e.g., for a polysaccharide (O antigen) synthesis cluster, such as that for *Shigella dysenteriae* O1.

In an embodiment, an expression plasmid for a bacterial O antigen, such as the *Shigella dysenteriae* O1 antigen, can be constructed as in pGVXN64 shown in FIG. 6B. This plasmid encodes all enzymes necessary to synthesize the polysaccharides in the *Shigella dysenteriae* strain that make up the O1 serotype. These enzymes are listed in the left-hand column of FIG. 6B. Vector pGVXN64 expressing the *Shigella dysenteriae* O1 antigen was constructed by digestion of pLARFR1 (Vanbleu, E. et al., "Genetic and physical map of the pLAFR1 vector" DNA Seq. 15(3):225-227 (2004)) with EcoR1 followed by insertion of an oligonucleotide cassette (5'-AATTCTGCAGGATCCTCTAGAAGCTTGG (SEQ. ID NO. 3) and 5'-AATTCCAAGCTTCTAGAGGATCCTGCAG (SEQ. ID NO. 4). The BamH1 fragment of pSDM7 (Falt, I. et al., "Construction of recombinant aroA salmonellae stably producing the *Shigella Dysenteriae* serotype 1 O-antigen and structural characterization of the *Salmonella/Shigella* hybrid LPS" Microb. Pathog. 20(1):11-30 (1996)) containing the rfb and rfp cluster of *Shigella dysenteriae* O1 was then cloned via the BamH1 site into the oligonucleotide cassette containing pLAFR1. The complete nucleotide sequence encoding the *Shigella dysenteriae* O1 antigen in the pGVXN64 plasmid is set forth as SEQ. ID NO.: 5 in the Sequence Listing provided below.

The host organism for an expression system of the invention can be, e.g., an *Escherichia coli* strain such as *Escherichia coli* W31110ΔwaaL. The deletion of WaaL prevents the transfer of any polysaccharide to the lipid A core. The chromosomal copy of WaaL can also be replaced by PglB. The strain also contains mutation in wbbL, therefore it does not produce any *E. coli O*16 polysaccharide. To further increase the production of carrier lipid linked polysaccharide, wecG has been deleted to prevent the formation of ECA (Entero Common Antigen).

In one aspect, the instant invention is further directed to the development of bioconjugate vaccines, preferably LPS bioconjugate vaccines, against one or more *Shigella* species, which are invasive, gram-negative bacteria. *Shigella* species cause Shigellosis, a severe inflammation of the colon. There are 165 million cases in the world every year, with 70% of such cases being in children under 5 years of age. In developing countries, Shigellosis causes 1.1 million of deaths per year. This is a serious disease that is spread via the fecal-oral route and is highly transmissible. Potential groups that would benefit from immunization against *Shigella* species include, for example, children, travelers and people in refugee camps.

There are four different serogroups of *Shigella*, namely, *S. dysenteriae, S. flexneri, S. sonnei* and *S. boydii*. In embodiments of the present invention, immunogenic bioconjugates can be made against each of these different serogroups of *Shigella*. For example, FIG. 14B provides different serotypes of *Shigella* and the polysaccharide structure that defines their antigenicity (i.e., *Shigella* O-antigens).

In further embodiments of the present invention, immunogenic LPS bioconjugates could be made against other bacteria using the teachings in this specification, including bacteria: (1) that cause nosocomial infections, such as *Pseudomonas aeruginosa*; and (2) that cause urinary tract infection, such as Extraintestinal *E. coli* (ExPEC).

In an embodiment, the inventors have developed a *Shigella dysenteriae* O1 LPS bioconjugate vaccine (also referred to as a *S. dysenteriae* bioconjugate), using genetically engineered *E. coli* with simple fermentation and purification methods. FIG. 9 shows production of *Shigella* bioconjugates. The top panel shows the synthesis of bioconjugates in *E. coli*. In an embodiment, the O-antigen repeating unit of *S. dysenteriae* O1 is assembled on the carrier lipid undecaprenyl pyrophosphate (UPP), flipped to the periplasmic space and polymerized. The structure of *S. dysenteriae* O1 is as follows and is also provided in the middle right of FIG. 9:
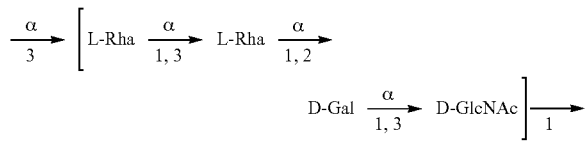

PglB transfers the activated polysaccharide to Asn residues of protein carriers, forming the *Shigella* bioconjugates. The protein carrier can be, for example, AcrA or a protein carrier that has been modified to contain the consensus sequence for protein glycosylation, i.e., D/E-X-N-Z-S/T, wherein X and Z can be any amino acid except proline (e.g., a modified Exotoxin *Pseudomonas aeruginosa* (EPA)). EPA has been used successfully in conjugate vaccines.

In an embodiment illustrated in FIG. 9, periplasmic proteins of *E. coli* cells expressing the modified EPA in the presence of PglB and the O1 polysaccharide cluster were separated by SDS page and, after transfer to nitrocellulose, EPA was immunodetected with an antiserum that was raised against EPA (lane 2). In lane 1, periplasmic proteins of *E. coli* cells expressing the *Campylobacter* protein AcrA in the presence of PglB and the O1 polysaccharide cluster were separated and immunodetected with an antiserum that was raised against AcrA. Both proteins were glycosylated with the O1-polysaccharide cluster. In the lowest panel of FIG. 9, the LPS from *E. coli* were separated by SDS-PAGE and visualized by Silver Staining. The left lane depicts the LPS extracted from a strain not expressing the WaaL, whereas the right lane shows the typical O1 LPS pattern. Both strains are expressing the polysaccharide biosynthesis cluster of *S. dysenteriae* O1.

The production of a bacterial bioconjugate, such as a *Shigella* bioconjugate, is described in an embodiment in further detail with reference to FIGS. 10A and 10B. Prior to assembly of the bacterial bioconjugate using a bacterial system, such as *E. coli*, it is necessary to introduce into the bacterial system certain genetic sequences coding for the various enzymes and proteins to be used, as discussed earlier with reference to FIGS. 8A and 8B. For example, this includes an OST/Otase, preferably from *C. jejuni* (e.g., PglB), a protein carrier (e.g. EPA) and a gene cluster directed to antigenic polysaccharide synthesis (e.g., the gene cluster for *S. dysenteriae* O1 polysaccharide synthesis).

FIG. 10A shows Step 1 in the development of a bacterial bioconjugate, namely, the biosynthesis of a polysaccharide, such as the O-antigen of *S. dysenteriae* Serotype O1. In this step, the antigen is synthesized on the carrier lipid undecaprenyl pyrophosphate (UPP), and then transferred into the periplasm using a flippase. The antigen is polymerized by the polymerase Wzy and transferred to the lipid A core by the ligase WaaL. To transfer the polysaccharide to a protein carrier, the ligase is replaced by the oligosaccharyltransferase; PglB.

Step 2 in the production of a bacterial bioconjugate involves engineering a suitable protein carrier. Protein carriers that are useful preferably should have certain immunological and pharmacological features. From an immunological perspective, preferably, a protein carrier should: (1) have T-cell epitopes; (2) be capable of delivering an antigen to antigen presenting cells (APCs) in the immune system; (3) be potent and durable; and (4) be capable of generating an antigen-specific systemic IgG response. From a pharmacological perspective, preferably, a protein carrier should: (1) be non-toxic; and (2) be capable of delivering antigens efficiently across intact epithelial barriers. More preferably, in addition to these immunological and pharmacological features, a protein carrier suitable for the production of a bacterial bioconjugate should: (1) be easily secreted into the periplasmic space; and (2) be capable having antigen epitopes readily introduced as loops or linear sequences into it.

The inventors have found genetically detoxified *Pseudomonas aeruginosa* Exotoxin (EPA) and the *Campylobacter* protein AcrA to be suitable protein carriers, most preferably EPA. AcrA contains natural glycosylation sites whereas EPA needs to be modified to encode glycosylation sites. Preferably, EPA is modified to introduce two glycosylation sites directed to the *Shigella* O1 antigen. More preferably, two consensus sequences are introduced as discussed in Example 10.

The amino acid sequence of EPA, as modified in an embodiment of this invention to contain two glycosylation sites, is provided as SEQ. ID NO.: 6 (with signal sequence) and SEQ. ID NO.: 7 (without signal sequence) in the Sequence Listing provided below. The glycosylation sites in each of SEQ. ID NO.: 6 and SEQ. ID NO.: 7 are denoted with an underline.

FIG. 10B shows a schematic of a carrier protein, such as EPA onto which N-glycosylation sites can be designed as Step 3 in the production of a bacterial bioconjugate. N-glycosylation sites require introduction of the consensus sequences discussed previously, namely, insertion of D/E-X-N-Z-S/T sequons, wherein X and Z may be any natural amino acid except proline. We have found that such consensus sequences preferably are introduced through surface loops, by insertion rather than mutation and considering using flanking residues to optimize the operation of the N-glycosylation site.

FIG. 11 shows bicoonjugates that elicit an immune response against *Shigella* O1 polysaccharide in mice. O1-AcrA and O1-EPA was purified by affinity column and anionic exchange. The pure bioconjugate was injected into mice (n=10). Serum of mice that were immunized with O1-AcrA (top) or O1-EPA (bottom) three times (day 1, 21, 60) was pooled and analyzed by ELISA at day 70 for a sugar specific IgG response. The plates (Nunc, polysorb) were coated with LPS isolated from *S. dysenteriae* O1 and incubated with the serum and anti mouse Polyvalent-HRP. Mice that received either conjugate developed an IgG response against the polysaccharide, confirming the presence of T-cell epitopes on the two protein carriers.

Consequently, the bacterial bioconjugates of the present invention show in vivo immnogenicity. In an embodiment, bacterial bioconjugates are capable of exhibiting: (1) a carbohydrate specific response; and (2) a carrier specific response or a similar response irrespective of the carrier protein. Moreover, an IgG specific response shows T-cell dependency of the immune response, such that memory of the response is expected.

FIG. 12 reflects production of a *Shigella* O1 bioconjugate, e.g., O1-EPA, in a bioreactor. *E. coli* cells expressing EPA, PglB and the O1-polysaccharide were grown in a bioreactor to $OD_{600}$=40 by two nutrient pulses. Expression of PglB and EPA was induced and the cells were grown overnight by linear feed of nutrients. The growth curve is depicted in the top panel. Whole cell extracts were separated by SDS-PAGE and expression and glycosylation of EPA was analyzed by immunodetection using a polyclonal antierserum that was raised against EPA (bottom). The cells efficiently glycosylate EPA at high cell density. The process is reproducible and leads to a total optical density (OD) of 90, which is a 45-fold increase compared to the shake flask culture. Consequently, scale-up is possible using the fed-batch process.

FIG. 13 shows an example of purification of O1-EPA. More specifically, FIG. 13 shows the fractionation and chromatographic purification of *S. dysenteriae* O1 bioconjugate. *E. coli* cells expressing the O1-EPA were grown in the bioreactor to high cell density (See FIG. 12). The cells were pelleted by centrifugation and periplasmic proteins were extracted by osmotic shock. Periplasmic proteins were separated by anionic exchange (Source Q). Fractions enriched for O1-EPA were further purified by a second column (Fluoroapatite). The different fractions were separated by SDS-PAGE and the proteins were visualized by Coomassie Blue. Lane 1 shows whole cells extracts, lane 2 periplasmic proteins after osmotic shock, lane 3 periplasmic proteins loaded on anionic exchange, lane 4 and 5 eluates from anionic exchange and lane 6 O1-EPA eluate after the second purification column. This process allows the purification of O1-EPA at large scale. In this embodiment, the purification process is: (1) efficient (at >10 mg/L culture); (2) possible at large scale; and (3) compatible with Good Manufacturing Practices (GMP). Following such purification, the EPA-O1 yield for glycerol-LB fed-batch was up to 200 mg/L, which is substantially higher than the yield for LB shake flask, which was 0.6 mg/L.

FIG. 14A shows a Western blot analysis of a series of specimens of AcrA-*Shigella* O1 bioconjugates produced in an LB shake flask taken under various conditions, including pre-induction, 4 hours after induction, and 4 hours and 19 hours after induction under oxygen-limited circumstances. After extraction and purification, periplasmic proteins were separated by SDS-PAGE. AcrA and AcrA-*Shigella* O1 bioconjugates were detected using anti-AcrA antibody and chemiluminescent detection via a secondary antibody. Loaded samples were normalized to culture $OD_{600}$ at time of sampling.

In summary, in one aspect, the technology of the present invention has been used to develop a vaccine against *S. dysenteriae* O1 infection. For example, the polysaccharide of *S. dysenteriae* O1 can be conjugated to EPA in *E. coli*. This is very beneficial since EPA previously has been successfully used in clinical trials with different conjugate vaccines. In the instant invention, the *S. dysenteriae* O1 bioconjugate was produced in a bioreactor at 31 scale. The cells were grown to high OD and the bioconjugate was extracted by osmotic shock. The bioconjugates were purified to 98% purity by anionic exchange and size exclusion chromatography. The bioconjugates were injected into different mice strains. After two as well as three injections, a sugar specific IgG response against the polysaccharide was detected using LPS from *Shigella dysenteriae* O1 for analysis (FIG. 11). As expected, IgM specific response was elicited when the LPS was injected. The bioconjugates raised a specific IgG response against the polysaccharide isolated from *S. dysenteriae*. IgG response against the corresponding sugar antigen, which was chemically coupled to a carrier protein, has been shown to correlate with protection in humans.

These results strongly suggest that our inventive *E. coli* strain is suitable for the potential production of an antigenic bacterial vaccine, such as an antigenic *Shigella* vaccine. In an embodiment, the EPA-*Shigella* bioconjugate was characterized intensively by different methods, like NMR, HPLC and MS. FIG. 15 shows the expansion of the anomeric region of 1H NMR spectrum of an example of a *S. dysenteriae* Serotype O1 bioconjugate of the invention. The bioconjugate contains a sugar/protein ratio of 0.15, with 13.2 repeating units of the antigen being linked to the protein, and 1-2 sites being glycosylated. Two consensus sequences for glycosylation were introduced into EPA and about 20% of the protein is fully glycoslyated. The polysaccharide is linked via the reducing end to the protein carrier; therefore, the antigen epitopes of the polysaccharide are unmodified. In addition, the in vivo conjugation method attaches just the O-antigen repeating units to the protein, but no monosaccharides of the lipid A core are attached.

Using this technology, bacterial bioconjugates can be produced that are immunogenic. Genetic modifications can be made allowing in vivo conjugation of bacterial polysaccharides in desired proteins and at desired positions. For example, in an embodiment and as discussed above, the antigenic polysaccharide of *S. dysenteriae* O1 can be expressed in *E. coli* and conjugated to two different protein carriers in vivo (i.e., EPA and AcrA). Both bioconjugates elicit a specific IgG response against the polysaccharide in mice. As another example, Table 1 below depicts different polysaccharide substrates for bacterial OSTs/OTases such as PglB that can be used in the in vivo method of the present invention for conjugating a protein carrier with the polysaccharide.

TABLE 1

| | |
|---|---|
| *C. jejuni* N-glycan | 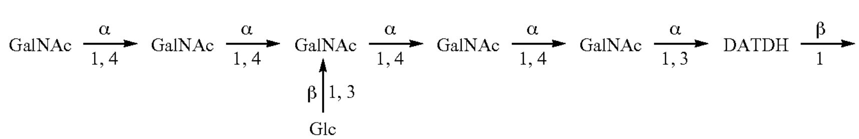  |
| *Shigella dysenteriae* O1 | 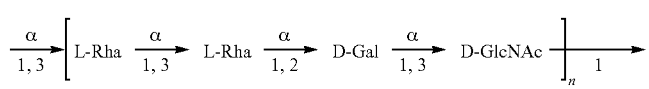  |
| *Pseudomonas aeruginosa* O11 | 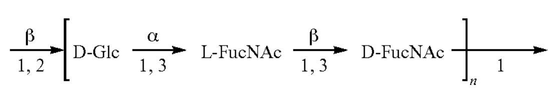  |

TABLE 1-continued
*E. coli* O16
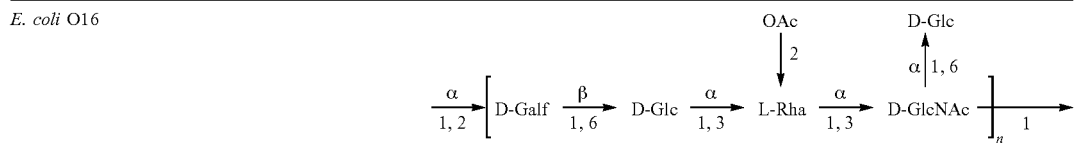
Table 2 below depicts yet additional different LPS polysaccharide substrates that could be utilized in the present invention with respect to various strains of *Shigella* and *E. coli.*, as well as of *Pseudomonas aeruginosa* O11 and *Francisella tularensis*.
TABLE 2

TABLE 2-continued

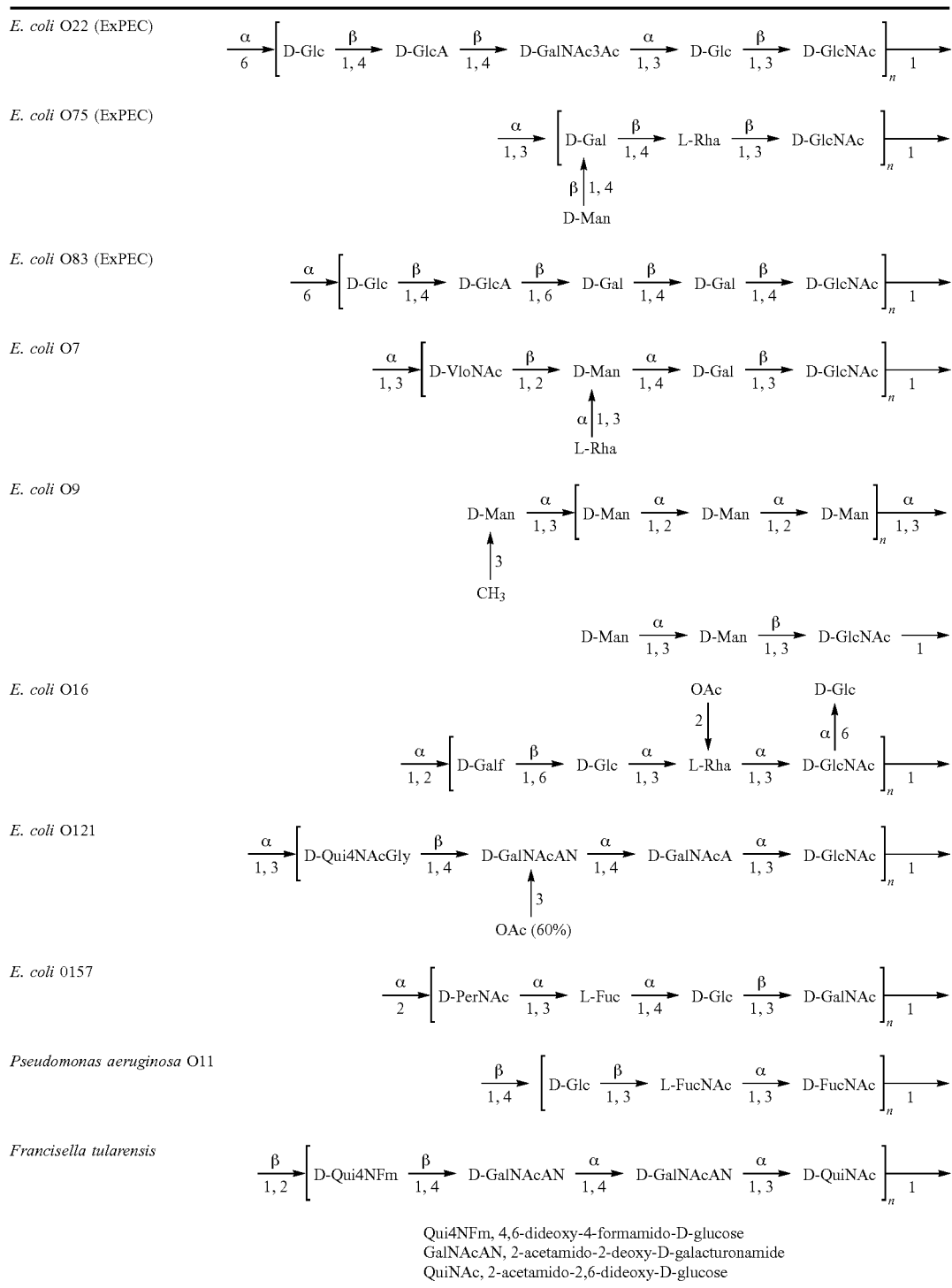

Qui4NFm, 4,6-dideoxy-4-formamido-D-glucose
GalNAcAN, 2-acetamido-2-deoxy-D-galacturonamide
QuiNAc, 2-acetamido-2,6-dideoxy-D-glucose For example, in a further embodiment of the invention, bioconjugate vaccines against *E. coli* can also be developed. *E. coli* is a well-known bacterial species. From a genetic and clinical perspective, *E. coli* strains of biological significance to humans can be broadly categorized as commensal strains, intestinal pathogenic strains and extraintestinal pathogenic *E. coli* (ExPEC). ExPEC strains can be part of the normal intestinal flora and are isolated in 11% of healthy individuals. They do not cause gastroenteritis in humans but their main feature is their capacity to colonize extraintestinal sites and to induce infections in diverse organs or anatomical sites. They are the main cause of urinary tract infections (UTI), are involved in septicemia, diverse abdominal infections and meningitis. Bacteremia can arise with a risk of severe sepsis. Severe sepsis due to ExPEC was associated with 41,000 estimated deaths in 2001. ExPEC strains have been susceptible to antibiotics; however more and more antibiotic resistant strains have evolved, both in hospital and in the community. This antimicrobial resistance is making the management of ExPEC infections more difficult; therefore, new vaccines would be an alternative strategy to prevent these infections.

In animal models, passive or active immunization against capsule, O-specific antigen and different outer membrane proteins have afforded protection against systemic infections and immunization with these different antigens are protective against urinary tract infections from ExPEC strains expressing these virulence factors. The serotypes O4, O6, O14, O22, O75 and O83 cause 75% of UTI. In one embodiment, the novel technology of the present invention can be used to develop a monovalent LPS bioconjugate including one antigen (e.g., serotype O6, one of the major serotypes) and even a multivalent LPS bioconjugate including these 6 antigens. For example, the gene cluster encoding for the enzymes that synthesize the O-antigen for ExPEC could be amplified and then expressed in the Shigella production strain.

The instant invention involves a highly efficient production process with high potential yields that can be used for industrial scale preparations in a cost-efficient process. This novel, cost efficient bioengineering approach to producing bioconjugate can be applied to other conjugates and for other applications. An additional feature of the invention involves a considerable simplification of the production of bacterial vaccines with high reproducibility and a potentially reduced risk of lot failures.

Process for Manufacturing Conjugate Vaccine

It is now possible to engineer bacterial expression systems so that specific bioconjugates are produced that are biologically active. For example, the O-specific polysaccharide of S. dysenteriae has been conjugated to different protein carriers and the resulting bioconjugate has elicited a specific IgG response against the polysaccharide in mice. In an embodiment, the technology of the invention makes use of an oligosaccharyl transferase, for example, PglB of Campylobacter jejuni to couple bacterial polysaccharides (O antigens) in vivo to simultaneously express recombinant carrier proteins, yielding highly immunogenic bioconjugate vaccines.

A production process has been established that can be used on an industrial scale. This opens up the possibility that a multitude of various conjugate vaccines can be developed and manufactured using simple bacterial fermentation. The process has several advantages compared to the in vitro conjugation method depicted in the top panel of FIG. 6A. As it is a complete in vivo process, the cost and risk of failures are reduced significantly and the process is more reproducible. In addition, the consensus capture sequence allows the conjugation of polysaccharides to defined proteins at specific built-in sites, thereby facilitating regulatory acceptance and quality control. Finally, the development of conjugate vaccines is much faster since the process is simplified and requires only biotechnology tools. In addition, the in vivo conjugation process is suited for application where polysaccharide compositions prevent chemical cross-linking.

In an embodiment, the instant invention relates to the scaled-up production of recombinant glycosylated proteins in bacteria and factors determining glycosylation efficiency. For example, recombinant glycosylated proteins of the present invention can be made using the shakeflask process. Bioconjugates have previously been mainly produced in LB shake flask cultures. More preferably, in one aspect of the invention, a first fed-batch process can be used for the production of recombinant glycosylated proteins in bacteria. In a preferred manufacturing process, the aim is to achieve markedly increased final biomass concentrations while maintaining glycosylation efficiency and recombinant protein yield per cell and while maintaining simplicity and reproducibility in the process.

In one embodiment, bacterial bioconjugates of the present invention can be manufactured on a commercial scale by developing an optimized manufacturing method using typical E. coli production processes. First, one can use various types of feed strategies, such as batch, chemostat and fed-batch. Second, one can use a process that requires oxygen supply and one that does not require an oxygen supply. Third, one can vary the manner in which the induction occurs in the system to allow for maximum yield of product.

It has found been that, in contrast to expression of the carrier protein, the degree of N-linked glycosylation strongly reacts to changes in nutrient availability, type of carbon- and energy source, oxygen supply and time-point of induction. For example, in a fed-batch process, the addition of inducers to the batch and fed-batch cultures immediately leads to a 3-fold decrease in specific growth rate, indicating a high metabolic burden and/or stress due to synthesis of the carrier protein and membrane-bound oligosaccharyltransferase. Based on the inventors' finding of a recurring retardation of the appearance of glycosylated carrier protein compared to the non-glycosylated form after induction, it is concluded that glycosylation appears to be the rate-limiting step in bioconjugate biosynthesis.

Based on these results, in an example of an embodiment of the invention, the following process design for cultivation has been developed: fed-batch cultivation mode for achieving high cell densities; extended incubation after induction to facilitate maximal glycosylation; surplus nutrient supply (e.g., LB components yeast extract and tryptone) during biomass build-up until induction to provide a sufficient supply of building blocks for the production process; and glycerol as the main carbon and energy source to prevent catabolite repression and acetate formation. This bioprocess allows a 50-fold increase in yield compared to LB batch culture, paving the way towards a cost-effective production of conjugate vaccines in recombinant Escherichia coli. In this example, one can have oxic conditions throughout the production process, for example, achieved through oxygen-enriched aeration; however, low oxygen content is also feasible. Example 9 sets forth this example of a fed-batch process in greater detail. It should be recognized, however, that other processes may be used to produce the bacterial LPS bioconjugates of the present invention.

Consequently, in one embodiment of the invention, E. coli can be used for in vivo production of glycosylated proteins and is suitable for industrial production of glycosylated proteins.

The following examples serve to illustrate further the present invention and are not intended to limits its scope in any way.

EXAMPLES

Example 1: Selection of AcrA as Model Protein for Optimizing N-Glycosylation

To optimize the acceptor protein requirements for N-glycosylation detailed studies were performed on the C. jejuni glycoprotein AcrA (CjO367c). AcrA is a periplasmic lipoprotein of 350 amino acid residues. It has been shown that secretion to the periplasm but not lipid-anchoring is a prerequisite for glycosylation (Nita-Lazar et al., 2005, supra). The signal for export can either be the native AcrA signal sequence or the heterologous PelB signal when expressed in *E. coli*. Of the five potential Winked glycosylation sequons (N117, N123, N147, N273, N274) the same two ones are used in *C. jejuni* and *E. coli* (N123 and N273 (Nita-Lazar et al., 2005, supra)). AcrA was chosen as model because it is the only periplasmic N-glycoprotein of *C. jejuni* for which detailed structural information is available. Recently, the crystal structure of an AcrA homologue, the MexA protein from the Gram-negative bacterium *P. aeruginosa*, was published (Higgins et al., (2004). Structure of the periplasmic component of a bacterial drug efflux pump. Proc. Natl. Acad. Sci. USA 7Of$_1$ 9994-9999). Both proteins are members of the so-called periplasmic efflux pump proteins (PEP,(Johnson, J. M. and Church, G. M. (1999). Alignment and structure prediction of divergent protein families: periplasmic and outer membrane proteins of bacterial efflux pumps. J. Mol. Biol. 287, 695-715)). The elongated molecule contains three linearly arranged subdomains: an α-helical, anti-parallel coiled-coil which is held together at the base by a lipoyl domain, which is followed by a six-stranded β-barrel domain. The 23-28 residues at the N-terminus and 95-101 residues in the C-terminus are unstructured in the crystals. MexA and AcrA protein sequences are 29.3% identical and 50% similar. Thus, the two proteins likely exhibit a similar overall fold.

Example 2: Elucidation of the Primary Peptide Sequence that Triggers Glycosylation It is known that lipoyl domains similar to MexA of *P. aeruginosa* and accordingly also in AcrA of *C. jejuni* form a compact protein that can be individually expressed in *E. coli* (reviewed by Berg, A., and de Kok, A. (1997). 2-Oxo acid dehydrogenase multienzyme complexes. The central role of the lipoyl domain. Biol. Chem. 378, 617-634). To check which acceptor peptide sequence was required for N-glycosylation by the pgl machinery in *E. coli* the lipoyl domain of AcrA was taken. It was used as a molecular scaffold to transport peptides of different lengths to the periplasm and present them to the pgl machinery in vivo.

Therefore, a plasmid coding for the lipoyl domain (Lip) was constructed and N-terminally fused to the signal sequence of OmpA (Choi, J. H., and Lee, S. Y. (2004). Secretory and extracellular production of recombinant proteins using *Escherichia coli*. Appl Microbiol Biotechnol 64, 625-635) and C-terminally to a hexa histag. Cloning was performed to place the gene expression under the control of the arabinose promoter. For the Lip domain borders amino acid positions were chosen that appeared at the same positions as the domain borders of the Lipoyl domain part in MexA. To test different peptides for their ability to accept an N-glycan stretches of the sequence were inserted between the two hammerhead-like parts of the Lip domain. The stretches consisted of sequences comprising the N-glycosylation site N123 of *C. jejuni* AcrA. The resulting open reading frames consisted of the sequences coding for the OmpA signal sequence, the N-terminal hammerhead-like part of AcrA (D60-D95, the numbering of the amino acids refers to the mature AcrA polypeptide sequence numbering), the different stretches containing the native N123 glycosylation site of AcrA (see below), the C-terminal hammerhead-like part of AcrA-Lip (L167-D210) and the C-terminal his-tag.

Construction of the plasmids was achieved by standard molecular biology techniques. Three stretches containing the native N123 glycosylation site of AcrA of different lengths were inserted between the two halves of Lip resulting in three different ORFs:

Construct A contains A118-S130 resulting in a protein sequence of:

(SEQ. ID NO. 8)
MKKTAIAIAVALAGFATVAQADVIIKPQVSGVIVNKLFKAGDKVKKGQT

LFIIEQDQASKDFNRSKALFSQLDHTEIKAPFDGTIGDALVNIGDYVSA

STTELVRVTNLNPIYADGSHHHHHH.

Construct B contains F122-E138 resulting in a protein sequence of:

(SEQ. ID NO. 9)
MKKTAIAIAVALAGFATVAQADVIIKPQVSGVIVNKLFKAGDKVKKGQ

TLFIIEQDQFNRSKALFSQSAISQKELDHTEIKAPFDGTIGDALVNIG

DYVSASTTELVRVTNLNPIYADGSHHHHHH.

Construct C contains D121-A127 resulting in a protein sequence of:

(SEQ. ID NO. 10)
MKKTAIAIAVALAGFATVAQADVIIKPQVSGVIVNKLFKAGDKVKKG

QTLFIIEQDQDFNRSKALDHTEIKAPFDGTIGDALVNIGDYVSASTT

ELVRVTNLNPIYADGSHHHHHH.

The underlined stretches of sequence indicate the OmpA signal peptide, singly underlined residues were introduced for cloning reasons or to render the protein resistant to degradation. Bold: glycosylation site corresponding to N123 of AcrA. Italics: hexa-histag. The corresponding genes were expressed under the control of the arabinose promoter in the backbone of the plasmid pEC415 (Schulz, H., Hennecke, H., and Thony-Meyer, L. (1998). Prototype of a heme chaperone essential for cytochrome c maturation. Science 281, 1197-1200).

To check which of the three stretches triggered glycosylation of the Lip proteins protein expression experiments were performed. *E. coli* Top 10 cells (Invitrogen, Carlsbad, Calif., USA) carrying pACYCpgl or pACYCpglmut (Wacker et al., 2002, supra) and a plasmid coding constructs A$_1$ B or C were grown in LB medium containing ampicillin and chloramphenicol up to an OD of 0.5 at 37° C. For induction 1/1000 volume 20% arabinose (w/v) solution was added and the cells were grown for another 2 hrs. The cells were then harvested by centrifugation and resuspended in 20 mM Tris/HCl, pH 8.5, 20% sucrose (w/v), 1 mM EDTA, 1 mM PMSF, and 1 g/l (w/v) lysozyme and incubated at 4° C. for 1 hr. Periplasmic extracts were obtained after pelletting of the spheroblasts and diluted with 1/9 volume (v/v) of 10× buffer A (3 M NaCl, 0.5 M Tris/HCl, pH 8.0 and 0.1 M imidazole) and MgSO$_4$ added to 2.5 mM. Ni-affinity purification was performed on 1 ml Ni-Sepharose columns from Amersham Pharmacia Biotech (Uppsala, Sweden) in buffer A. Proteins were eluted in buffer A containing 0.25 M imidazole.

Figure 1:
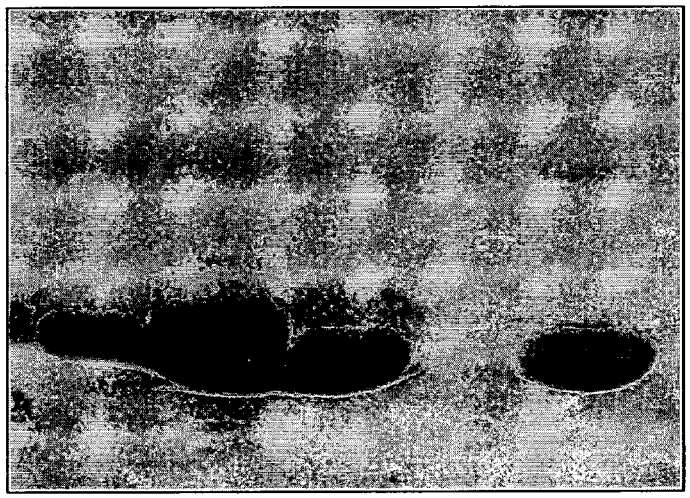
FIG. 1 illustrates the N-glycosylation of Lip proteins derived from constructs A to C (see example 1). E. coli Top 10 cells carrying a functional pgl operon from C. jejuni (Wacker et al., 2002, supra) and a plasmid coding for constructs A (lane 2), B (lane 1), and C (lane 3) or a mutant of construct C with the mutation D121A (lane 4). Proteins were expressed and purified from periplasmic extracts. Shown is the SDS-PAGE and Coomassie brilliant blue staining of the purified protein fractions.

FIG. 1 shows Coomassie brilliant blue stained SDS-PAGE gel of the peak elution fractions from the Ni-purified periplasmic extracts. The expression analysis showed that construct B produced a prominent single protein species (FIG. 1, lane 1). Constructs A and C both lead, in addition to the prominent protein, to a second protein band with slower electrophoretic mobility (FIG. 1, lanes 2 and 3). That the heavier protein species was indeed glycosylated was proven by MALDI-TOF/TOF (not shown). The only amino acid missing in construct B but present in A and C was D121, the aspartate residue 2 positions N-terminally to the glycosylated N123. This demonstrates that D121 plays an important role for glycosylation by the OTase. To verify that D121 is essential for glycosylation it was mutated to alanine in construct C. Expression analysis resulted in only one protein band (FIG. 1, lane 4), thus showing that D121 is important for glycosylation. Furthermore, the fact that an artificial peptide display protein can be glycosylated shows that a short peptide of the D/E-X-N-Y-S/T type contains all information for *C. jejuni*-borne N-glycosylation to occur.

Example 3: Verification of Example 2;
AcrA-D121A is not Glycosylated at N123

To confirm the findings from the peptide display approach an aspartate to alanine mutation was inserted at position 121 (D121A, i.e. 2 residues before the glycosylated N123) in the full length soluble version of the AcrA protein and it was tested whether the site N123 could still be glycosylated in *E. coli*. In order to test this AcrA-D121A was expressed and its glycosylation status was analyzed. For the analysis an engineered AcrA was used. It differed from the original *C. jejuni* gene in that it contains the PelB signal sequence (Choi and Lee, 2004, supra) for secretion into the periplasm and a C-terminal hexa histag for purification. It has been shown that this AcrA variant gets secreted, signal peptide-cleaved and glycosylated as the lipid anchored, native protein (Nita-Lazar et al., 2005, supra). The following is the amino acid sequence of the soluble AcrA protein:

```
                                            (SEQ. ID NO. 11)
MKYLLPTAAAGLLLLAAQPAMAMHMSKEEAPKIQMPPQPVTTMSAKSE

DLPLS/TYPAKLVSDYDVIIKPQVSGVIVNKLFKAGDKVKKGQTLFII

EQDKFKASVDSAYGQALMAKATFENASKDFNRSKALFSKSAISQKEYD

SSLATFNNSKASLASARAQLANARIDLDHTEIKAPFDGTIGDALVNIG

DYVSASTTELVRVTNLNPIYADFFISDTDKLNLVRNTQSGKWDLDSIH

ANLNLNGETVQGKLYFIDSVIDANSGTVKAKAVFDNNNSTLLPGAFAT

ITSEGFIQKNGFKVPQIGVKQDQNDVYVLLVKNGKVEKSSVHISYQNN

EYAIIDKGLQNGDKIILDNFKKIQVGSEVKEIGAQLEHHHHHH
```

The underlined residues are the PelB signal peptide, italics the hexa-histag, and bold the two natural glycosylation sites at N123 and N273. A plasmid containing the ORF for the above protein in the pEC415 plasmid (Schulz et al., 1998) was constructed to produce pAcrAper.

The assay to test the glycosylation status of AcrA and mutants thereof (see below) was as follows: expression of AcrA was induced with 0.02% arabinose in exponentially growing *E. coli* CLM24 (Feldman et al., 2005, supra) cells containing the plasmid-borne pgl operon in its active or inactive form (pACYCpg/or pACYCpg/mut, see (Wacker et al., 2002, supra)) and a plasmid coding for AcrA (pAcrAper). After four hours of induction, periplasmic extracts were prepared as described above and analyzed by SDS-PAGE, electrotransfer and immunodetection with either anti-AcrA antiserum or R12 antiserum. The latter is specific for *C. jejuni* N-glycan containing proteins (Wacker et al., 2002, supra).

Figure 2:
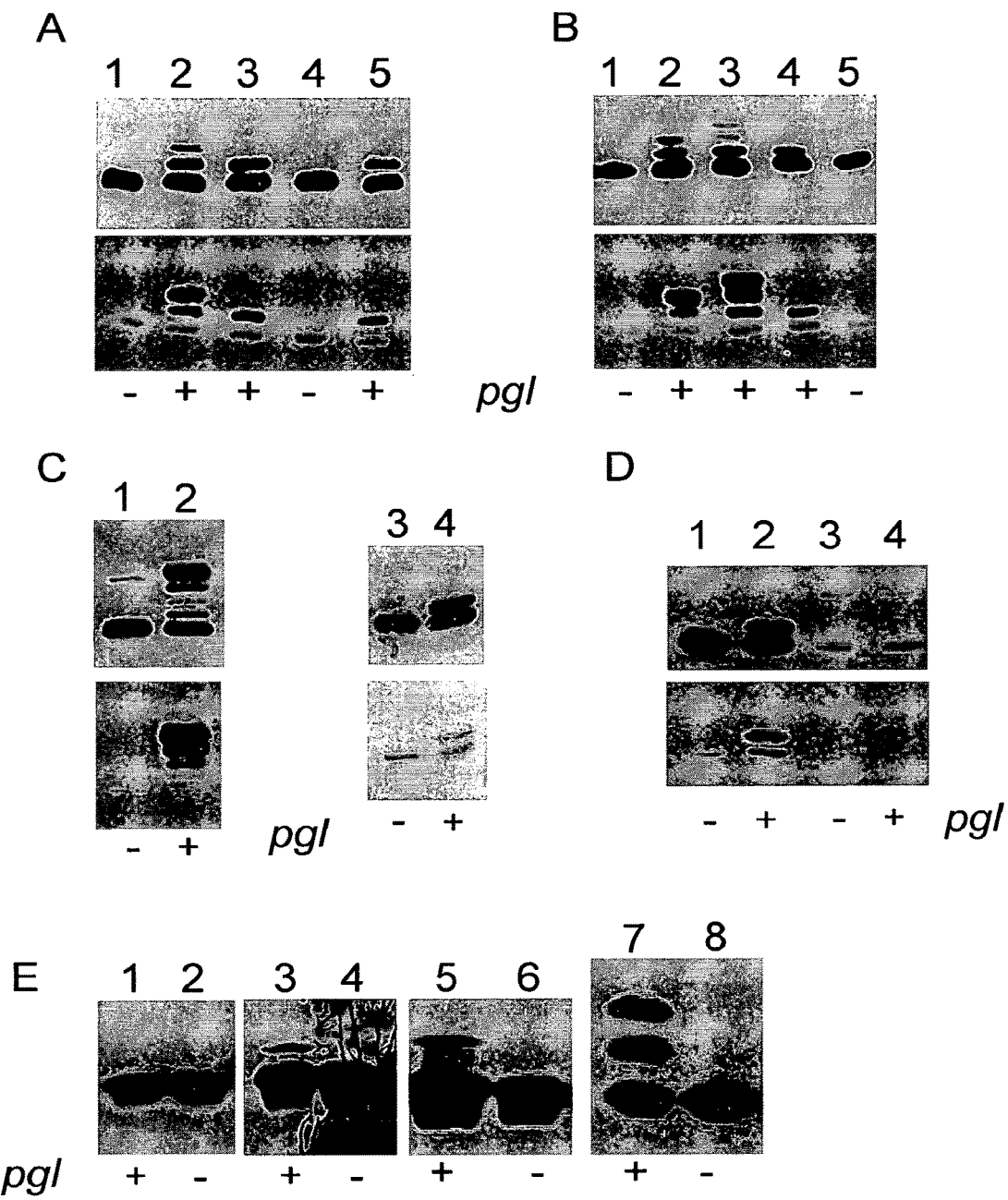
FIG. 2 shows the N-glycosylation analysis of the different proteins that were analyzed for the sequence specific N-glycosylation by the C. jejuni pgl operon (Wacker et al., 2002, supra) in CLM24 cells (Feldman et al., (2005). Engineering N-linked protein glycosylation with diverse O antigen lipopolysaccharide structures in Escherichia coli. Proc. Natl. Acad. Sci. USA 102, 3016-3021) or Top10 cells (panel E lanes 1-6) or SCM7 cells (Alaimo, C, Catrein, I., Morf, L., Marolda, C. L., Callewaert, N., Valvano, M. A., Feldman, M. F., Aebi, M. (2006). Two distinct but interchangeable mechanisms for flipping of lipid-linked oligosaccharides. EMBO Journal 25, 967-976) (panel E, lanes 7, 8) expressing said proteins from a plasmid. Shown are SDS-PAGE separated periplasmic extracts that were transferred to a nitrocellulose membrane and visualized with specific antisera. In panels A-D, the top panels show immunoblots probed with anti AcrA antiserum (Wacker et al. 2002, supra; Nita-Lazar, M., Wacker, M., Schegg, B., Amber, S., and Aebi, M. (2005). The N-X-S/T consensus sequence is required but not sufficient for bacterial N-linked protein glycosylation. Glycobiology 15, 361-367), whereas the bottom panels show immunoblots probed with R12 antiserum (Wacker et al., 2002, supra). + and − indicate the presence of the functional or mutant pgl operon in the cells. Panel A contains samples of the soluble wildtype AcrA with the pelB signal sequence and the hexa histag (lanes 1, 2), AcrA-N273Q (lane 3, 4), and AcrA-D121A (lane 5). Panel B: AcrA (lanes 1, 2), AcrA-T145D (lane 3), AcrA-N123Q-N273Q-T145D (lanes 4, 5). Panel C: AcrA-F115D-T145D (lanes 1, 2), AcrA-N123Q-N273Q-N272D (lanes 3, 4). Panel D: AcrA-N273Q (lanes 1, 2), AcrA-N273Q-F122P (lanes 3, 4). Panel E: CtxB (lanes 1, 2), CtxB-W88D (lanes 3, 4), CtxB-Q56/DSNIT (lanes 5, 6), and CtxB-W88D-Q56/DSNIT.

The first two lanes of FIG. 2A show AcrA in the absence and presence of a functional pgl operon. Only one band appears in the absence but three in the presence of the functional pgl operon (FIG. 2A, top panel). These correspond to unglycosylated AcrA (lane 1) and un-, monO- and diglycosylated AcrA (lane 2). That the two heavier proteins in lane 2 were glycosylated was confirmed by the R12 western blot (lane 2, bottom panel). When the mutant AcrA-N273Q was expressed the same way, only the monoglycosylated AcrA was detected in presence of the functional glycosylation pgl operon (lane 3). Unglycosylated AcrA was detected in absence of the functional pgl locus (lane 4). Analysis of the mutant AcrA-D121A produced only two bands, one of them glycosylated (lane 5) as observed with AcrA-N273Q in lane 3. This means that D121 is essential for efficient glycosylation at position 123-125.

Example 4: Introducing Artificial Glycosylation Sites into AcrA

To test if the introduction of an aspartate residue could generate a glycosylation site, AcrA mutants were generated in which the residue in the −2 position of the not used glycosylation sites in positions N117 and N147 of soluble AcrA were exchanged for aspartate (F115D, T145D). It was then tested whether the modified glycosylation sites could be glycosylated by the same assay as described in example 2. Both mutations were individually inserted either into the wildtype sequence of the soluble version of AcrA or in the double mutant in which both used glycosylation sites were deleted (N123Q and N273Q). Periplasms extracts of cultures induced for 4 hrs were prepared, separated by SDS page and analyzed by Western blotting (FIG. 2B). As controls the samples of wildtype glycosylated and non glycosylated AcrA were run on the same gel (lanes 1 and 2). The T145D mutation affected the −2 position of the natively not used glycosylation sequon N147-S149. Upon expression of AcrA-T145D Western blotting with anti AcrA antiserum resulted in four bands, the highest of them with slower electrophoretic mobility than the doubly glycosylated protein in lane 2 (lane 3 in FIG. 2B). The R12 blot confirmed that the fourth band was a triply glycosylated AcrA. Despite the low intensity towards anti AcrA the heaviest band gave the strongest signal with the glycosylation specific R12 antiserum. When the same mutant AcrA-T145D was expressed in the absence of the native N-glycosylation sequence (AcrA-N123Q-N273Q-T145D), only monoglycosylated AcrA was detected in the presence of a functional pgl operon (FIG. 2B, lane 4), that was missing in absence of a functional pgl operon (lane 5). This demonstrates that the heavier band in lane 4 was glycosylated. Hence, by simply introducing the T145D mutation an optimized glycosylation site was generated (DFNNS).

To further confirm that it is possible to introduce a glycosylation site by inserting an aspartate residue in the −2 position, the natively not used sites N117-S119 and N274-T276 were changed to optimize N-glycosylation. For this purpose further mutants were generated (FIG. 2C). Expression of AcrA-F115D-T145D in the above described system resulted in five protein species detected with the anti AcrA antiserum (lane 2). This is indicative for four glycosylates taking place on the same AcrA molecule. When the detection was performed with the *C. jejuni* N-glycan-specific R12 antiserum, a ladder of five bands was detected. The lowest faint band is unglycosylated AcrA because it is also present in the absence of glycosylation (lane 1), the highest results in a strong signal probably due to the five antigenic determinants in a fourfold glycosylated AcrA. Thus, the two introduced sites (at NI 17 and N147) and the two natively used sites (N123 and N273) are used and glycosylated by the pgl machinery. Expression of AcrA-N123Q-N273Q-N272D with and without the pgl operon demonstrated that a third artificially introduced glycosylation site, N274 (DNNST), was also recognized by the pgl operon (FIG. 2C, lanes 3 and 4).

The above experiments confirm the finding that the bacterial N-glycosylation site recognized by the OTase of *C. jejuni* consists partly of the same consensus as the eukaryotic one (N-X-S/T, with X≠P) but, in addition, an aspartate in the −2 position is required for increasing efficiency. Furthermore, they demonstrate that it is possible to glycosylate a protein at a desired site by recombinantly introducing such an optimized consensus sequence.

Example 5: Verification of Position −1 in the Optimized N-Glycosylation Sequence A further experiment was performed to test whether the −1 position in the bacterial glycosylation site exhibits the same restrictions as the +1 position in eukaryotes (Imperiali, B., and Shannon, K. L. (1991). Differences between Asn-Xaa-Thr-containing peptides: a comparison of solution conformation and substrate behaviour with oligosaccharyltransferase. Biochemistry 30, 4374-4380; Rudd, P. M., and Dwek, R. A. (1997). Glycosylation: heterogeneity and the 3D structure of proteins. Crit. Rev. Biochem. Mol. Biol. 32, 1-100). A proline residue at +1 is thought to restrict the peptide in such a way that glycosylation is inhibited. To test if a similar effect could also be observed in the −1 position a proline residue was introduced at that position of the first natively used site in a point mutant that had the second native site knocked out (AcrA-N273Q-F122P). The control expression of AcrA-N273Q showed a monoglycosylated protein in the presence of a functional pgl operon (FIG. 2D, lane 1 and 2). However, AcrA-N273Q-F122P was not glycosylated (FIG. 2D, lanes 3 and 4). This indicates that proline inhibited bacterial N-glycosylation when it constitutes the residue between the asparagine and the negatively charged residue of the −2 position.

Sequence alignments of all the sites known to be glycosylated by the *C. jejuni* pgl machinery indicate that they all comprise a D or E in the −2 position (Nita-Lazar et al., 2005, supra; Wacker et al., 2002, supra; Young et al., (2002). Structure of the N-linked glycan present on multiple glycoproteins in the Gram-negative bacterium, *Campylobacter jejuni*. J. Biol. Chem. 277, 42530-42539). Thus, it was established that the glycosylation consensus sequence for bacteria can be optimized by a negatively charged amino acid in the −2 position, resulting in D/E-X-N-Z-S/T, wherein X & Z≠P.

Example 6: N-Glycosylation of a Non-*C. jejuni* Protein

To demonstrate that the primary sequence requirement (optimized consensus sequence) is sufficient for N-glycosylation in bacteria, it was tested whether a non-*C. jejuni* protein could be glycosylated by applying the above strategy. Cholera toxin B subunit (CtxB) was employed as a glycosylation target. The corresponding gene was amplified from *Vibrio cholerae* in such a way that it contained the coding sequence of the OmpA signal sequence on the N-terminus and a hexahistag at the C-terminus, just the same as constructs A through C in example 1. The resulting DNA was cloned to replace construct A in the plasmids employed in example 1. A point mutation of W88 to D or a D insertion after W88 generated an optimized glycosylation site (DNNKT). The wildtype and W88D CtxB proteins containing the signal sequence and his-tag were expressed in *E. coli* Top 10 and other cell types in the presence and absence of the functional pgl locus from *C. jejuni*. When periplasmic extracts from Top 10 cells were analyzed by SDS-PAGE, electrotransfer and consecutive immunoblotting with a CtxB antiserum, only CtxB W88D produced a higher and thus glycosylated band in the pgl locus background (FIG. 2E, compare lanes 3 and 4). A consensus sequence (DSNIT) was also inserted by replacing G54 or Q56 of CtxB (the latter is denoted CtxB-Q56/DSNIT), i.e. in one of the loops that was reported to contribute to the ganglioside GM 1 binding activity of CtxB. Lanes 5 and 6 of FIG. 2E demonstrate that the engineered protein (exemplified by the construct which contains the peptide sequence DSNIT instead of Q56 expressed in Top10 cells) produced a lower mobility and thus glycosylated band in glycosylation competent but not glycosylation-deficient cells when analyzed in the same way as described above. It was also demonstrated that a CtxB containing two manipulations, i.e. the insertion of D after W88 as well as DSNIT replacing Q56, was double-glycosylated in SCM7 cells (Alaimo et al., EMBO Journal 25: 967-976 (2006)) (panel E, lanes 7 and 8). The double-glycosylated protein CtxB shown in lane 7 was Ni$^{2+}$ affinity-purified and analyzed by ESI-MS/MS after in-gel trypsinization according to standard protocols. The expected glycopeptides were detected confirming that bacterial N-glycosylation can also be directed to a non-*C. jejuni* protein by mutating or inserting the optimized consensus sequence according to the invention for bacterial N-glycosylation (not shown). Examples of other suitable exemplary *E. coli* strains for practicing the present invention are W3110, CLM24, BL21 (Stratagene, La Jolla, Calif., USA), SCM6 and SCM7.

The amino acid sequence of the CtxB protein used here is indicated below (recombinant OmpA signal sequence underlined, hexa-histag italics, W88 bold):

(SEQ. ID NO. 12)
<u>MKKTAIAIAVALAGFA</u>TVAQATPQNITDLCAEYHNTQIHTLNDKIFS

YTESLAGKREMAIITFKNGATFQVEVPGSQHIDSQKKAIERMKDTLR

IAYLTEAKVEKLCVWNNKTPHAIAAISMANGSH*HHHHH*

Example 7: Introduction of Artificial N-Glycosylation Sites into the *C. jejuni* Outer Membrane Protein, OmpH1

A potential application of the N-glycosylation in bacteria is the display of the glycan on the surface of a bacterial host cell in order to link the phenO- to the genotype and thereby select for specific genetic mutations. To demonstrate that N-glycans can be presented on outer membrane proteins the OmpH1 protein was engineered in a way that it contained multiple optimized consensus sites according to the invention. The sites were engineered into loop regions of the protein as deduced from the known crystal structure (Muller, A., Thomas, G. H., Horler, R., Brannigan, J. A., Blagova, E., Levdikov, V. M., Fogg, M. J., Wilson, K. S., and Wilkinson, A. J. 2005. An ATP-binding cassette-type cysteine transporter in *Campylobacter jejuni* inferred from the structure of an extracytoplasmic solute receptor protein. Mol. Microbiol.

Figure 3:
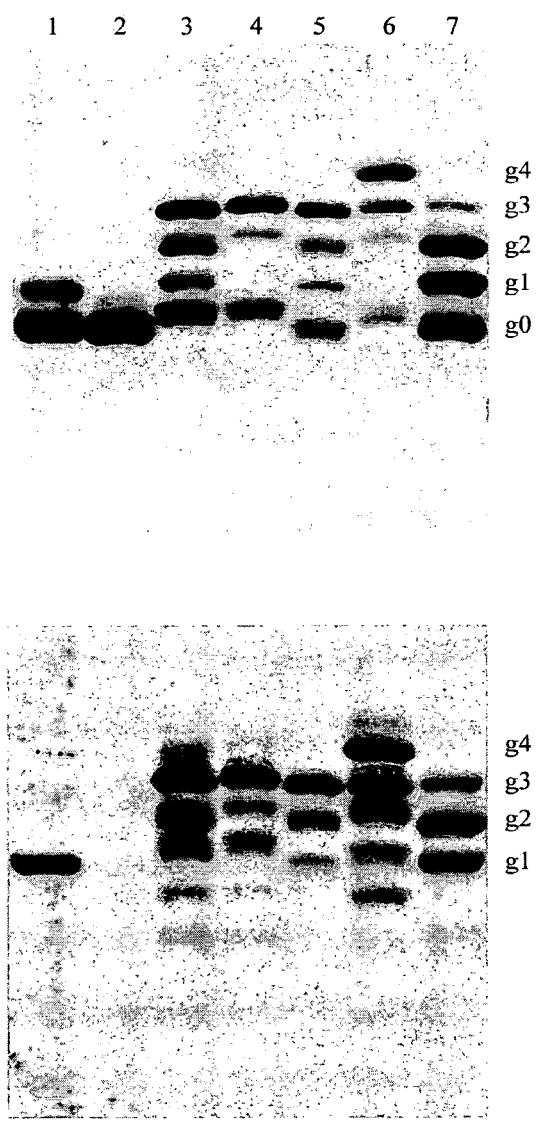
FIG. 3 shows the engineering of multiple glycosylation sites in OmpH1. The ΔwaaL strain SCM6 was co-transformed with plasmid pACYCpgl (encoding entire pgl locus) and plasmids expressing wild type OmpH1 (lane 1), OmpH1$^{N139S}$-myc (lane 2), OmpH1$^{KGN \to NIT\ HFGDD \to DSNIT}$- myc (lane 3), QmpH1$^{RGD \rightarrow NIT, HFGDD \rightarrow DSNT}$-myc (lane 4), OmpH1$^{KGN \rightarrow NIT, RGD \rightarrow NIT}$-myc (lane 5)$^{KGN-NIT, HFGDD \rightarrow DSNIT}$-myc (lane 6) or OmpH1$^{RGD \rightarrow NIT, V83T}$-myc (lane 7). The cells were grown aerobically, induced with 0.5% arabinose for 3 hours prior to analysis. Whole cell lysates were TCA precipitated after equalizing the optical density of the cultures as described in the materials and methods section. The proteins were separated by 15% SDS-PAGE and transferred onto a PVDF membrane. First panel, immunoblot of whole cell lysates probed with anti-myc tag antobodies. Bottom panel, immunoblot of whole cell lysates probed with glycan-specific antiserum. The positions of unglycosylated- and glycosylated OmpH1 are indicated on the right.

57: 143-155). Previous experiments showed that the best glycosylation sequons were generated by the mutations V83T, K59N-G601-N61T, R190N-G191I-D192T and H263D-F264S-G265N-D2661-D267T. For surface display it was desired to evaluate different combinations of those introduced sites in order to establish the most N-glycan-specific sample. The combinations were generated in a wild type OmpH1 encoding plasmid construct and tested in a similar manner as described for AcrA. FIG. 3 shows the analysis of various OmpH1 variants harboring multiple glycosylation sequons in addition to the existing wild type sequon. OmpH1 variants were generated with three (lane 3, 4, 5 and 7) and four glycosylation sequons (lane 6). A wild type OmpH1 with only one glycosylation sequon and a mutant lacking the critical asparagine for glycosylation were also included in the experiment. All variants tested here did not only demonstrate a high level of glycosylation efficiency but also that every glycosylation sequon was utilized. The results were confirmed with *Campylobacter* N-glycan specific immuneserum (FIG. 3 lower panel).

The following is the amino acid sequence of the OmpH1 protein of *Campylobacter jejuni* (strain 81-176) with attached myc tag in italics:

(SEQ. ID NO. 13)
MKKILLSVLTTFVAVVLAACGGNSDSKTLNSLDKIKQNGWRIGVFGDK

PPFGYVDEKGNNQGYDIALAKRIAKELFGDENKVQFVLVEAANRVEFL

KSNKVDIILANFTQTPERAEQVDFCLPYMKVALGVAVPKDSNITSVED

LKDKTLLLNKGTTADAYFTQDYPNIKTLKYDQNTETFAALMDKRGDAL

SHDNTLLFAWVKDHPDFKMGIKELGNKDVIAPAVKKGDKELKEFIDNL

IIKLGQEQFFHKAYDETLKAHFGDDVKADDWIEGGKILEQKL/*SEEDL*

The native glycosylation site in the protein is bold, the signal sequence underlined.

Example 8: Surface Display of N-Glycans from *C. jejuni* on OmpH1 on the Outer Membrane of *E. coli* Cells In order to answer the question whether multiple glycosylated OmpH1 variants can be displayed on the surface of bacterial cells, immunofluorescence was performed on bacterial CLM24 or SCM6 (which is SCM7 ΔwaaL) cells expressing various OmpH1 variants. A wild type OmpH1 and a mutant lacking the critical asparagine for glycosylation were included in the experiment. In addition, a C20S mutant was constructed in order to retain the protein in the periplasm, thus serving as a control in the experiment. Immunostaining was carried out on the cells treated with paraformaldehyde. Paraformaldehyde fixes cells without destroying the cell structure or compartimentalization. The c-Myc- and N-glycan-specific immuneserum in combination with corresponding secondary antibodies conjugated to FITC and Cy3 were used to detect the protein (red fluorescence) and N-glycan (green) on the bacterial cell surface, respectively. Additionally, 4,6-diaminO-2-phenylindole (DAPI, blue) was employed to stain for bacterial DNA to unambiguously differentiate between bacterial cells and cellular debris. When the cells expressing wild type OmpH1 were stained, immunofluorescence specific to the protein as well as the N-glycan was detected (FIG. 4 A). When a mutant lacking the critical asparagine N139S was stained with both anti-Myc- and N-glycan-specific immuneserum only the protein but not glycan specific signals were obtained (panel 4 B) indicating specificity of the N-glycan-specific immune serum. When the protein was retained within the periplasm as in the C20S mutant, no protein specific, red immunofluorescence was detected indicating that the antibodies were unable to diffuse within the cell and were competent enough to detect any surface phenomenon (panel 4 C). Next, cells expressing multiple OmpH1 variants different in glycosylation were stained: OmpH1$^{KGN \to NIT, HFGDD \to DSNIT}$ (panel 4 D), OmpH1$^{RGD \to NIT, HFGDD \to DSNIT}$ (panel 4 E), OmpH1$^{KGN \to NIT, RGD \to NIT}$ (panel 4 F), OmpH1$^{V83T, KGN \to NIT}$ (panel 4 G) and OmpH1$^{KGN \to NIT, RGD \to NIT, HFGDD \to DSNIT}$ (panel 4 H). All the OmpH1 variants were double-stained indicating the presence of glycosylated protein on the bacterial surface. FIG. 4 is represented in grayscale, the first column is a merge picture of the other pictures of the same row.

FIG. 4 shows fluorescence microscopy of cells expressing various OmpH1 variants. Cultures of *E. coli* strains CLM24 or SCM6 containing the expression plasmid for the wild type OmpH1 and its variants were equalized to OD$_{600}$ of 0.25/ml. Cells were washed two times with phosphate-buffered saline (PBS), pH 7.4 and 100 µl cell suspensions was dropped onto gelatinized glass slides and incubated at room temperature (RT) for 30 min inside a humidified chamber. All subsequent steps in the whole-cell immunofluorescence labeling were done at room temperature inside a humidified chamber. The unbound cells were removed and rest was fixed with 4% paraformaldehyde containing PBS for 30 min at RT. Importantly, paraformaldehyde is considered not to permeabilize cells but keeping the compartimentalization by membranes intact. Fixed cells were washed two times with PBS and resuspended blocking buffer containing 5% BSA in PBS. After blocking, the cells were incubated with anti-myc monoclonal mouse IgG (1:50, Calbiochem) and/or anti-glycan antiserum (1:4000) for 1 h in 100 µl of PBS containing 5% BSA. The cells were washed three times with 100 µl of PBS for 5 min each and incubated with secondary anti-rabbit antibody conjugated to FITC (1:250, Jackson Immunoresearch Laboratories) and/or anti-mouse antibody conjugated to Cy3 (1:250, Jackson Immunoresearch Laboratories) for 1 h in 100 µl of PBS containing 5% BSA. If required, 4,6-diaminO-2-phenylindole (DAPI) (Sigma) (0.5 µg/ml) was added at the time of secondary antibody incubation to stain for bacterial DNA. The secondary antibody was rinsed from the cells PBS$_1$ and coverslips were mounted on slides by using vectashield (Vector Laboratories) mounting medium and sealed with nail polish. Fluorescence microscopy was performed by the using an Axioplan2 microscope (Carl Zeiss). Images were combined by using Adobe Photoshop, version CS2. SCM6 cells expressing OmpH1 (panel A), OmpH1$^{N139S}$ (panel B), OmpH1$^{C20S}$ (panel C), OmpH1$^{KGN \to NIT, HFGDD \to DSNIT}$ (panel D), OmpH1$^{RGD \to NIT, HFGDD \to DSNIT}$ (panel E), OmpH1$^{KGN \to NIT, RGD \to NIT}$ (panel F), OmpH1$^{V83T, KGN \to NIT}$ (panel G), and OmpH1$^{KGN \to NIT, RGD \to NIT, HFGDD \to DSNIT}$ (panel H). The first column is a merge of the pictures in columns 2, 3, and 4 represented in greytones on black background. Column 2: blue fluorescence in greytones from DAPI stain, column 3: green fluorescence from glycan specific fluorescence, column 4: red fluorescence from anti-myc staining.

Example 9: An Example of a Production Process for *Shigella* O1 LPS Bioconjugate This is an example of a production process; however, different conditions also lead to similar product formation.

A. Production Process

E. coli strain W3110ΔwaaL containing three plasmids expressing PglB, EPA and the enzymes for the biosynthesis of the Shigella O1 polysaccharide was used for the production of the LPS bioconjugate. A single colony was inoculated in 50 ml LB medium and grown at 37° C. O/N. The culture was used to inoculate a 1l culture in a 2l bioreactor. The bioreactor was stirred with 500 rpm, pH was kept at 7.0 by autO-controlled addition of either 2 M KOH or 20% $H_3PO_4$ and the cultivation temperature was set at 37° C. The level of dissolved oxygen (pO2) was kept between 0 and 10% oxygen. The cells were grown in a semi defined glycerol medium containing Kanamycin to an $OD_{600}$=15. The medium contained the following ingredients: 330 mM Glycerol, 10 g Yeast extract, 20 g Tryptone, 34 mM $K_2HPO_4$, 22 mM $KH_2PO_4$, 38 mM $(NH_4)_2SO_4$, 2 mM $MgSO_4.7H_2O$ and 5 mM Citric acid. After an initial batch phase around 5 h, a first nutrient pulse was added to sustain fast biomass build-up (glycerol, tryptone and yeast extract). After an additional 1.5 h the culture reached an $OD_{600}$=30. At this timepoint a second nutrient pulse of glycerol and tryptone was added together with the required inducers 1% L-arabinose and 1 mM IPTG. In order to keep induction at maximum levels and supply further amino acids for recombinant protein synthesis, a linear nutrient/inducer feed (28.8 ml/h) was started with the addition this pulse. The feed was sustained until the end of the process. The bioreactor culture was harvested after a total of 24 h cultivation, when it should have reached an OD600 of ±80.

The production process was analyzed by Western blot as described previously (Wacker, M., et at, N-linked glycosylation in Campylobacter jejuni and its functional transfer into E. coli. Science, 2002. 298(5599): p. 1790-3.). After being blotted on nitrocellulose membrane, the sample was immunostained with the specific anti-EPA (Wacker, M., et al., N-linked glycosylation in Campylobacter jejuni and its functional transfer into E. coli. Science, 2002. 298(5599): p. 1790-3.). Anti-rabbit IgG-HRP (Biorad) was used as secondary antibody. Detection was carried out with ECL™ Western Blotting Detection Reagents (Amersham Biosciences, Little Chalfont Buchinghamshire).

FIG. 16A shows proteins extracted of the Shigella O1 LPS Bioconjugate (i.e., EPA-O1) from a fed-batch process that were normalized to biomass concentration (0.1 $OD_{600\ nm}$ of cells/lane). The proteins were separated by SDS-PAGE transferred to Nitrocellulose membrane and visualized by rabbit anti EPA antibody. The induction time for PglB and EPA expression was 1 h and O/N.

B. Periplasmic Protein Extraction

The cells were harvested by centrifugation for 20 min at 10,000 g and resuspended in 1 volume 0.9% NaCl. The cells were pelleted by centrifugation during 25-30 min at 7,000 g. The cells were resuspended in Suspension Buffer (25% Sucrose, 100 mM EDTA 200 mM Tris HCl pH 8.5, 250 OD/ml) and the suspension was incubated under stirring at 4-8° C. during 30 min. The suspension was centrifuged at 4-8° C. during 30 min at 7,000-10,000 g. The supernatant was discarded, the cells were resuspended in the same volume ice cold 20 mM Tris HCl pH 8.5 and incubated under stirring at 4-8° C. during 30 min. The spheroblasts were centrifuged at 4-8° C. during 25-30 min at 10,000 g, the supernatant was collected and passed through a 0.2μ membrane.

As shown in FIG. 16B, the periplasmic extract was loaded on a 7.5% SDS-PAGE, and stained with Coomasie to identify EPA and EPA-O1. EPA is a thick band that runs above the 70 kDa marker. O1-EPA (i.e., EPA-O1) runs as a leader between 100 and 170 kDa.

C. Bioconjugate Purification

The supernatant containing periplasmic proteins obtained from 100,000 OD of cells was loaded on a Source Q anionic exchange column (XK 26/40≈180 ml bed material) equilibrated with buffer A (20 mM Tris HCl pH 8.0). After washing with 5 column volumes (CV) buffer A, the proteins were eluted with a linear gradient of 15CV to 50% buffer B (20 mM Tris HCl+1M NaCl pH 8.0) and then 2CV to 100% buffer B. Protein were analyzed by SDS-PAGE and stained by Coomassie. Fractions containing O1-EPA were pooled. Normally the bioconjugate eluted at conductivity between 6-17 mS. The sample was concentrated 10 times and the buffer was exchanged to 20 mM Tris HCl pH 8.0.

As shown in FIG. 17A, protein fractions from 1. Source Q were analyzed by SDS-PAGE and stained by Coomassie. Fractions C1 to G9 contained O1 bioconjugate and were pooled.

The O1-Bioconjugate was loaded a second time on a Source Q column (XK 16/20≈28 ml bed material) that has been equilibrated with buffer A: 20 mM Tris HCl pH 8.0. The identical gradient that was used above was used to elute the bioconjugate. Protein were analyzed by SDS-PAGE and stained by Coomassie. Fractions containing O1-EPA were pooled. Normally the bioconjugate eluted at conductivity between 6-17 mS. The sample was concentrated 10 times and the buffer was exchanged to 20 mM Tris HCl pH 8.0.

As shown in FIG. 17B, protein fractions from 2. Source Q column were analyzed on SDS-PAGE and stained by Coomassie. Fractions A11 to B3 containing O1 bioconjugate were pooled.

The O1-Biconjugate was loaded on Superdex 200 (Hi Load 26/60, prep grade) that was equilibrated with 20 mM Tris HCl pH 8.0.

As shown in FIG. 18A, protein fractions from Superdex 200 column were analyzed by SDS-PAGE and stained by Coomassie stained. Fractions F1 to F11 were pooled.

As shown in FIG. 18B, Shigella bioconjugate from different purification steps were analyzed by SDS-PAGE and stained by Coomassie. O1-EPA was purified to more than 98% purity using the process, showing that O1-EPA bioconjugate can be successfully produced using this technology.

Example 10: Engineering of Exotoxin a of Pseudomonas aeruginosa for Glycosylation with Antigenic Carbohydrates Exotoxin A of Pseudomonas aeruginosa (EPA) is a 67 kDa extracellulary secreted protein encoding mature 613 amino acids in its mature form and containing four disulfide bridges (C11-C15, C197-C214, C265-C287, C372-C379). To enable its glycosylation in E. coli, the protein must locate to the periplasmic space for glycosylation to occur. Therefore, a the signal peptide of the protein DsbA from E. coli was genetically fused to the N-terminus of the mature EPA sequence. A plasmid derived from pEC415 [Schulz, H., Hennecke, H., and Thony-Meyer, L., Prototype of a heme chaperone essential for cytochrome c maturation, Science, 281, 1197-1200, 1998] containing the DsbA signal peptide code followed by a RNase sequence was digested (NdeI to EcoRI) to keep the DsbA signal and remove the RNase insert. EPA was amplified using PCR (forward oligo was 5'-AAGCTAGCGCCGCCGAGGAAGCCTTCGACC (SEQ. ID NO. 14) and reverse oligo was 5'-AAGAATTCTCAGTGGTGGTGGTGGTGGTGCTTCAGGTC- CTCGCGCGGCGG (SEQ. ID NO. 15)) and digested NheI/EcoRI and ligated to replace the RNase sequence removed previously. The resulting construct (pGVXN69) encoded a protein product with an DsbA signal peptide, the mature EPA sequence and a hexa-histag. Detoxification was achieved by mutating/deleting the catalytically essential residues L552VΔE553 according to [Lukac, M., Pier, G. B., and Collier, R. J., Toxoid of *Pseudomonas aeruginosa* exotoxin A generated by deletion of an active-site residue, Infect Immun, 56, 3095-3098, 1988] and [Ho, M. M., et al., Preclinical laboratory evaluation of a bivalent *Staphylococcus aureus* saccharide-exotoxin A protein conjugate vaccine, Hum Vaccin, 2, 89-98, 2006] using quick change mutagenesis (Stratagene) and phosphorylated oligonucleotides 5'-GAAGGCGGGCGCGTGACCATTCTCGGC (SEQ. ID NO. 16) and 5'-GCCGAGAATGGTCACGCGCCCGCCTTC (SEQ. ID NO. 17) resulting in construct pGVXN70.

It is known that insertion of a pentapeptide sequence of the type D/E-Z-N-X-S/T into a suitable position results in glycosylation. To glycosylate EPA in *E. coli* cells, two different glycosylation sites were inserted into the previously described constructs according to the following description.

To insert a site at position 375, two steps were performed. First, quick change mutagenesis using oligos 5'-CCTGACCTGCCCCGGGGAATGCGCGG (SEQ. ID NO. 18) and 5'-CCGCGCATTCCCCGGGGCAGGTCAGG (SEQ. ID NO. 19) with pGVXN70 as a template resulted in a construct containing a single SmaI site at amino acid position 375 of EPA protein sequence by deleting three residues but otherwise keeping the starting protein sequence intact. In a second step, an insert composed of two complementary, phosphorylated oligonucleotides coding for (i) the previously deleted residues (when inserting the SmaI site), (ii) the pentapeptide glycosylation sequon and (iii) additional lysine residues flanking the consensus for optimization of glycosylation efficiency (as was found by further experiments) was ligated into this SmaI site (5'-GTCGCCAAAGATCAAAATAGAACTAAA (SEQ. ID NO. 20) and 5'-TTAGTTCTATTTTGATCTTTGGCGAC (SEQ. ID NO. 21). The resulting construct was pGVXN137.

To insert an additional glycosylation site in the construct at amino acid 240, a one step procedure using quick change mutagenesis with oligonucleotides 5'-CATGACCTGGACATCAAGGATAATAATAATTCTACTCCCACGGTCATCAGTCATC (SEQ. ID NO. 22) and 5'-GATGACTGATGACCGTGGGAGTAGAATTATTATTATCCTTGATGTCCAGGTCATG (SEQ. ID NO. 23) was applied on construct pGVXN137. The resulting construct thus contained various changes compared to the wild type EPA protein: two glycosylation sites, a DsbA signal peptide, detoxification mutation.

While this invention has been particularly shown and described with references to embodiments thereof, it will be understood by those skilled in the art that various changes in form and detail may be made therein without departing from the scope of the invention encompassed by the claims. Moreover, in instances in the specification where specific nucleotide or amino acid sequences are noted, it will be understood that the present invention encompasses homologous sequences that still embody the same functionality as the noted sequences. Preferably, such sequences are at least 85% homologous. More preferably, such sequences are at least 90% homologous. Most preferably, such sequences are at least 95% homologous.

The invention claimed is:

1. A method of producing a composition comprising a bioconjugate separated from periplasmic proteins, wherein said bioconjugate comprises a carrier protein linked to an O antigen, said method comprising:
   (i) culturing a prokaryotic host cell that comprises (A) a nucleic acid encoding a carrier protein comprising the amino acid sequence D/E-X-N-Z-S/T, wherein X and Z may be independently any natural amino acid except proline; (B) a nucleic acid encoding an oligosaccharyl transferase; and (C) one or more nucleic acids encoding one or more glycosyltransferases capable of assembling the O antigen on a lipid carrier, wherein said culturing is done for a period of time sufficient for the host cell to produce the bioconjugate;
   (ii) extracting periplasmic proteins from the prokaryotic host cell; and (iii) separating the bioconjugate from the extracted periplasmic proteins and unconjugated carrier protein by anionic exchange, wherein said O antigen is from extraintestinal pathogenic *Escherichia coli* (ExPEC), *Shigella flexneri* 2a, *S. flexneri* 3a, *S. flexneri* 3b, *S. flexneri* 6 or *S. sonnei*.

2. The method of claim 1, wherein said 0-antigen is heterologous to said host cell.

3. The method of claim 1, wherein said carrier protein is heterologous to said host cell.

4. The method of claim 1, wherein said carrier protein is *Pseudomonas aeruginosa* exoprotein (EPA); AcrA (CjO367c), HisJ (CjO734c), or OmpH1 (CjO982c) from *Campylobacter jejuni*; Diphteria toxin (CRM197); or Cholera toxin.

5. The method of claim 4, wherein said carrier protein is *Pseudomonas aeruginosa* exoprotein (EPA).

6. The method of claim 1, wherein said oligosaccharyl transferase is heterologous to said host cell.

7. The method of claim 1, wherein said oligosaccharyl transferase is from *Campylobacter*.

8. The method of claim 7, wherein said oligosaccharyl transferase is from *Campylobacter jejuni*.

9. The method of claim 1, wherein said composition is at least 98% pure with respect to the bioconjugate.

* * * * *

SEQUENCE LISTING

<160> NUMBER OF SEQ ID NOS: 29

<210> SEQ ID NO 1
<211> LENGTH: 2169
<212> TYPE: DNA
<213> ORGANISM: Campylobacter jejuni

<400> SEQUENCE: 1

```
atgttgaaaa aagagtattt aaaaaaccct tatttagttt tgtttgcgat gattatatta      60
gcttatgttt ttagtgtatt ttgcaggttt tattgggttt ggtgggcaag tgagtttaat     120
gagtattttt tcaataatca gttaatgatc atttcaaatg atggctatgc ttttgctgag     180
ggcgcaagag atatgatagc aggttttcat cagcctaatg atttgagtta ttatggatct     240
tctttatccg cgcttactta ttggctttat aaaatcacac ctttttcttt tgaaagtatc     300
attttatata tgagtacttt tttatcttct ttggtggtga ttcctactat tttgctagct     360
aacgaataca aacgtccttt aatgggcttt gtagctgctc ttttagcaag tatagcaaac     420
agttattata atcgcactat gagtgggtat tatgatacga atatgctggt aattgttttg     480
cctatgttta ttttatttttt tatggtaaga atgattttaa aaaaagactt ttttttcattg     540 attgccttgc cgttatttat aggaatttat ctttggtggt atccttcaag ttatacttta     600
aatgtagctt taattggact ttttttaatt tatacactta tttttcatag aaaagaaaag     660
attttttata tagctgtgat tttgtcttct cttactcttt caaatatagc atggttttat     720
caaagtgcca ttatagtaat acttttttgct ttattcgcct tagagcaaaa acgcttaaat     780
tttatgatta taggaatttt aggtagtgca actttgtat ttttgatttt aagtggtggg     840
```

```
gttgatccta tactttatca gcttaaattt tatatttta gaagtgatga aagtgcgaat    900
ttaacgcagg gctttatgta ttttaatgtc aatcaaacca tacaagaagt tgaaaatgta    960
gatcttagcg aatttatgcg aagaattagt ggtagtgaaa ttgtttttt gttttctttg   1020
tttggttttg tatggctttt gagaaaacat aaaagtatga ttatggcttt acctatattg   1080
gtgcttgggt ttttagcctt aaaaggggg cttagattta ccatttattc tgtacctgta   1140
atggccttag gatttggttt tttattgagc gagtttaagg ctataatggt taaaaaatat   1200
agccaattaa cttcaaatgt tgtattgtt tttgcaacta ttttgacttt agctccagta   1260
tttatccata tttacaacta taaagcgcca acagttttt ctcaaaatga agcatcatta   1320
ttaaatcaat taaaaaatat agccaataga gaagattatg tggtaacttg ggcggcttat   1380
ggttatcctg tgcgttatta tagcgatgtg aaaactttag tagatggtgg aaagcattta   1440
ggtaaggata atttttcc ttcttttgct ttaagcaaag atgaacaagc tgcagctaat   1500
atggcaagac ttagtgtaga atatacagaa aaaagctttt atgctccgca aaatgatatt   1560
ttaaaaacag acatttgca agccatgatg aaagattata atcaaagcaa tgtggatttg   1620
tttctagctt cattatcaaa acctgatttt aaaatcgata cgccaaaaac tcgtgatatt   1680
tatctttata tgcccgctag aatgtctttg atttttcta cggtggctag tttttctttt   1740
attaatttag atacaggagt tttggataaa ccttttacct ttagcacagc ttatccactt   1800
gatgttaaaa atggagaaat ttatcttagc aacggagtgg tttaagcga tgatttaga   1860
agttttaaaa taggtgataa tgtggtttct gtaaatagta tcgtagagat taattctatt   1920
aaacaaggtg aatacaaaat cactccaatt gatgataagg ctcagtttta tattttat   1980
ttaaaggata gtgctattcc ttacgcacaa tttatttaa tggataaaac catgtttaat   2040
agtgcttatg tgcaaatgtt tttttagga aattatgata agaatttatt tgacttggtg   2100
attaattcta gagatgctaa ggttttaaaa cttaaaattt acccatacga tgttccagat   2160
tacgcttaa                                                            2169

<210> SEQ ID NO 2
<211> LENGTH: 722
<212> TYPE: PRT
<213> ORGANISM: Campylobacter jejuni

<400> SEQUENCE: 2

Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
            20                  25                  30

Val Trp Trp Ala Ser Glu Phe Asn Glu Tyr Phe Phe Asn Asn Gln Leu
        35                  40                  45

Met Ile Ile Ser Asn Asp Gly Tyr Ala Phe Ala Glu Gly Ala Arg Asp
    50                  55                  60

Met Ile Ala Gly Phe His Gln Pro Asn Asp Leu Ser Tyr Tyr Gly Ser
65                  70                  75                  80

Ser Leu Ser Ala Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
            100                 105                 110

Val Ile Pro Thr Ile Leu Leu Ala Asn Glu Tyr Lys Arg Pro Leu Met
        115                 120                 125
```

-continued

```
Gly Phe Val Ala Ala Leu Leu Ala Ser Ile Ala Asn Ser Tyr Tyr Asn
            130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
                    165                 170                 175

Phe Phe Ser Leu Ile Ala Leu Pro Leu Phe Ile Gly Ile Tyr Leu Trp
                180                 185                 190

Trp Tyr Pro Ser Ser Tyr Thr Leu Asn Val Ala Leu Ile Gly Leu Phe
            195                 200                 205

Leu Ile Tyr Thr Leu Ile Phe His Arg Lys Glu Lys Ile Phe Tyr Ile
210                 215                 220

Ala Val Ile Leu Ser Ser Leu Thr Leu Ser Asn Ile Ala Trp Phe Tyr
225                 230                 235                 240

Gln Ser Ala Ile Ile Val Ile Leu Phe Ala Leu Phe Ala Leu Glu Gln
                    245                 250                 255

Lys Arg Leu Asn Phe Met Ile Ile Gly Ile Leu Gly Ser Ala Thr Leu
                260                 265                 270

Ile Phe Leu Ile Leu Ser Gly Gly Val Asp Pro Ile Leu Tyr Gln Leu
            275                 280                 285

Lys Phe Tyr Ile Phe Arg Ser Asp Glu Ser Ala Asn Leu Thr Gln Gly
290                 295                 300

Phe Met Tyr Phe Asn Val Asn Gln Thr Ile Gln Glu Val Glu Asn Val
305                 310                 315                 320

Asp Leu Ser Glu Phe Met Arg Arg Ile Ser Gly Ser Glu Ile Val Phe
                    325                 330                 335

Leu Phe Ser Leu Phe Gly Phe Val Trp Leu Leu Arg Lys His Lys Ser
                340                 345                 350

Met Ile Met Ala Leu Pro Ile Leu Val Leu Gly Phe Leu Ala Leu Lys
            355                 360                 365

Gly Gly Leu Arg Phe Thr Ile Tyr Ser Val Pro Val Met Ala Leu Gly
370                 375                 380

Phe Gly Phe Leu Leu Ser Glu Phe Lys Ala Ile Met Val Lys Lys Tyr
385                 390                 395                 400

Ser Gln Leu Thr Ser Asn Val Cys Ile Val Phe Ala Thr Ile Leu Thr
                    405                 410                 415

Leu Ala Pro Val Phe Ile His Ile Tyr Asn Tyr Lys Ala Pro Thr Val
                420                 425                 430

Phe Ser Gln Asn Glu Ala Ser Leu Leu Asn Gln Leu Lys Asn Ile Ala
            435                 440                 445

Asn Arg Glu Asp Tyr Val Val Thr Trp Ala Ala Tyr Gly Tyr Pro Val
450                 455                 460

Arg Tyr Tyr Ser Asp Val Lys Thr Leu Val Asp Gly Lys His Leu
465                 470                 475                 480

Gly Lys Asp Asn Phe Phe Pro Ser Phe Ala Leu Ser Lys Asp Glu Gln
                    485                 490                 495

Ala Ala Ala Asn Met Ala Arg Leu Ser Val Glu Tyr Thr Glu Lys Ser
                500                 505                 510

Phe Tyr Ala Pro Gln Asn Asp Ile Leu Lys Thr Asp Ile Leu Gln Ala
            515                 520                 525

Met Met Lys Asp Tyr Asn Gln Ser Asn Val Asp Leu Phe Leu Ala Ser
530                 535                 540
```

-continued

```
Leu Ser Lys Pro Asp Phe Lys Ile Asp Thr Pro Lys Thr Arg Asp Ile
545                 550                 555                 560

Tyr Leu Tyr Met Pro Ala Arg Met Ser Leu Ile Phe Ser Thr Val Ala
            565                 570                 575

Ser Phe Ser Phe Ile Asn Leu Asp Thr Gly Val Leu Asp Lys Pro Phe
        580                 585                 590

Thr Phe Ser Thr Ala Tyr Pro Leu Asp Val Lys Asn Gly Glu Ile Tyr
    595                 600                 605

Leu Ser Asn Gly Val Val Leu Ser Asp Phe Arg Ser Phe Lys Ile
610                 615                 620

Gly Asp Asn Val Val Ser Val Asn Ser Ile Val Glu Ile Asn Ser Ile
625                 630                 635                 640

Lys Gln Gly Glu Tyr Lys Ile Thr Pro Ile Asp Asp Lys Ala Gln Phe
            645                 650                 655

Tyr Ile Phe Tyr Leu Lys Asp Ser Ala Ile Pro Tyr Ala Gln Phe Ile
        660                 665                 670

Leu Met Asp Lys Thr Met Phe Asn Ser Ala Tyr Val Gln Met Phe Phe
    675                 680                 685

Leu Gly Asn Tyr Asp Lys Asn Leu Phe Asp Leu Val Ile Asn Ser Arg
690                 695                 700

Asp Ala Lys Val Phe Lys Leu Lys Ile Tyr Pro Tyr Asp Val Pro Asp
705                 710                 715                 720

Tyr Ala
```

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aattctgcag gatcctctag aagcttgg                                       28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aattccaagc ttctagagga tcctgcag                                       28

<210> SEQ ID NO 5
<211> LENGTH: 10174
<212> TYPE: DNA
<213> ORGANISM: Unknown
<220> FEATURE:
<221> NAME/KEY: source
<223> OTHER INFORMATION: /note="Description of Unknown: Shigella
      dysenteriae O1 Antigen in the PGVXN64 plasmid"

<400> SEQUENCE: 5
atgaaaaacc ataaggttag tattatcatc ccctgtttta ataacggaaa aactatagaa 60
agatgcgttc tttccgcatt aaaacaaacc catagaaata tagagattat ttgtataaat 120
gatggaccgt cagataatag ctggaatatt ttaaagaaat taagctcatt gtatggaaat 180

```
gttttttgctt ttaataatga ggacaattca gggccgtcat tttccaggat taaaggggtt      240
tcactatcta cggggcattt tttgtcattt ttggatgcag atgattactg gcatccaaaa      300
aaactagaat tacaactatc atttattaat gatgaaaact tggatttttt aggttcaacg      360
tgttccattg gtgagaaaaa taaccaagaa attaaccaag gaattaaaaa agaacattta      420
aaattaaaaa taatttcatt taacatgatg ttgtttaaga attatttcca gactccagct      480
gtcattatga aaagagatat ttttattcca tttaatgaga atcagcgttt ttcagaggac      540
tacatgtcat ggcttgttat cgtttataat aaaaaaacaa atgtggattt aatatatgga      600
agggatttgg ttttttctcga taaatttaac tttggagtgt cagggttgag tggtaattta      660
tggttgatgg agaagtggga gttaaaaaat atatttaact tcttgttgaa aggtaaaata      720
atggcagtgc ctgcgatctt gttttctttg ataaaatatg aaagaagatg cgctttaaca      780
aagaaaaata aaggtaaggg taataaataa tgaagatctc aataataggg aacacagcaa      840
atgctatgat tttgtttaga ttggatttaa taaaaacact aaccaacaaa gggatttcag      900
tctatgcttt tgctactgac tataatgatt catccaagga ataataaaaa aaagcaggcg      960
ccattcctgt tgattataat ttaagtcgca gtggtattaa ccttgctggt gatttatgga     1020
atacttactt attaagtaaa aaactaaaga agataaaacc agatgctatt ttatcttttt     1080
tttcaaagcc ctctatcttt ggatcgttgg ctggtatttt ttcaggcgtt aaaaataata     1140
acgctatgct tgaggggtta ggttttttat ttacagagca gccacatgga actccgttaa     1200
aaacaaagtt acttaaaaat atccaggttc tcctgtataa aataatattt ccacatatca     1260
actcattaat actccttaac aaggatgatt atcatgattt gatagataaa tacaaaataa     1320
aattaaaatc ttgccatatt cttggtggca ttggtttaga tatgaataat tactgtaaaa     1380
gcacgccacc aacaaatgaa atatcattca tttttatagc tcgtttgcta gcagaaaaag     1440
gagtcaatga gtttgttgct gccgcaaaaa aaataaaaaa aacacatccc aatgttgaat     1500
ttattatact tggcgctata gataaggaaa accccggagg gttatctgaa tctgacgtag     1560
atactttaat taaatcagga gttatttctt atcccggatt tgtttctaat gtggctgatt     1620
ggattgaaaa atcaagcgta tttgttcttc cttcctatta tcgagaggga gttcctcgta     1680
gtacacaaga agcgatggct atggggaggc cgattttaac tactaattta ccaggctgca     1740
aagaaacaat tattgatggt gtgaatggat atgttgtaaa aaaatggtca catgaagatc     1800
ttgcagaaaa aatgctgaag ttaattaata atcctgaaaa aataatcagt atgggagaag     1860
aaagttataa gttagcaaga gaaagattcg atgcaaatgt aaataatgta aagttattaa     1920
aaatactagg gattcctgat taataaacga aaagcggctc tgattcattc ggaactaaga     1980
acctatctca ataggagcta aattcatgac cttacccagc catatcgacc tgcagcctga     2040
ctgatgccat tgccgaactg gcgaaaaaac agtccgttga tgccatgctg atgactggag     2100
acagctacga ctgcggaaaa aaatgggct atatgcaggc gtttgtgaag tatgggctgc     2160
gcaacctcaa agaaggggcg aagttccgta aagggattga gaagctgtta agcgaataat     2220
gaaaatctga ccgaatgtaa cggttgataa gaaaattata acggcagtga agattcgtgg     2280
cgaaagtaat ttgttgcgaa tattcctgcc gttgttttat ataaacaatc agaataacaa     2340
agagttagca ataggatttt cgtcaaagtt ttccaggatt ttccttgttt ccagagcgga     2400
ttggtaagac aattagtgtt tgaattttc gggtttagcg cgagtgggta acgctcgtca     2460
catcgtggac atgtatgcag tgctctggta gctgtaaagc caggggcggt agcgtgcatt     2520
aatacctcta ttaatcaaac tgagagccgc ttatttcaca gcatgctctg aagtaatatg     2580
```

```
gaataataaa gtgaagatac ttgttactgg tggcgcagga tttattggtt ctgctgtagt    2640
tcgtcacatt ataaataata cgcaggatag tgttgttaat gtcgataaat taacgtacgc    2700
cggaaacctg gagtcacttg ctgatgtttc tgactctaaa cgctatgttt ttgaacatgc    2760
ggatatttgc gatgctgctg caatggcgcg gattttttgct cagcatcagc cggatgcagt    2820
gatgcacctg gctgctgaaa gccatgtgga tcgttcaatt acaggccctg cggcatttat    2880
tgaaaccaat attgttggta cttatgtcct tttggaagcg gctcgcaatt actggtctgc    2940
tcttgatggc gacaagaaaa atagcttccg ttttcatcat atttctactg acgaagtcta    3000
tggtgatttg cctcatcctg acgaagtaaa taataaagaa caattacccc tctttactga    3060
gacgacagct tacgcgccta gtagtccttta ttccgcatca aaagcatcca gcgatcattt    3120
agtccgtgcg tggaaacgta cctatggttt accgaccatt gtgactaact gttcgaataa    3180
ctacggtcct tatcactttc cggaaaaatt gattccacta gtaattctta atgctctgga    3240
aggtaaggca ttacctattt atggcaaagg ggatcaaatt cgtgactggc tgtatgttga    3300
agatcatgcg cgtgcgttat atatcgtcgt aaccgaaggt aaagcgggtg aaacttataa    3360
cattggtgga cacaacgaaa agaaaaacat cgatgtagtg ctcactattt gtgatttgtt    3420
ggatgagatt gtaccgaaag agaaatctta ccgcgagcaa attacttatg ttgccgatcg    3480
cccgggacac gatcgccgtt atgcgattga tgcagagaag attagccgcg aattgggctg    3540
gaaaccgcag gaaacgtttg agagcgggat tcgtaaaacg gtgggatggt acctctccaa    3600
tacaaaatgg gttgataatg taaaaagtgg tgcctatcaa tcgtggattg aacagaacta    3660
tgagggccgc cagtaatgaa tatcctcctt ttcggcaaaa cagggcaggt aggttgggaa    3720
ctacagcgtg ctctggcacc tctgggtaat ttgattgctc ttgatgttca ctccactgat    3780
tactgtggta attttagtaa tcctgaaggt gtagctgaaa ccgtaagaag cattcggcct    3840
gatattattg tcaacgcagc cgctcacacc gcagtagaca aagcagaatc agaaccggag    3900
tttgcacaat tacttaacgc gacgagtgtc gaagcgatcg cgaaagcagc caatgaagtc    3960
ggcgcctggg ttattcacta ctctactgac tacgtatttc cggggaccgg tgaaatacca    4020
tggcaggagg cggatgcaac cgcaccgcta aatgtttacg gtgaaaccaa gttagctgga    4080
gaaaaagcat tacaagagca ttgtgcgaag cacctaattt tccgtacaag ctgggtctat    4140
gcaggtaaag gaaataactt cgccaaaacg atgttgcgtc tgggaaaaga gcgtgaagaa    4200
ttagccgtta ttaatgatca gtttggtgcg ccaacaggtg ctgaactgct ggctgattgt    4260
acggcacatg caattcgtgt ggcactgaat aaaccagaag tcgcaggctt gtaccatctg    4320
gtagccactg gtaccacaac ctggcacgat tatgctgcgc tggttttga agaggcacga    4380 aaagcaggta ttccccttgc actcaacaag ctcaacgcag taccaacaac agcttatcct    4440
acaccagctc gtcgtccaca taactctcgc cttaatacag aaaaatttca gcaaaatttt    4500
gcgcttgttt tgcctgactg gcaggttggc gtgaaacgaa tgctcaacga attatttacg    4560
actacagcaa tttaatagtt tttgcatctt gttcgtgatg atggagcaag atgaattaaa    4620
aggaatgatg taatgaaaac gcgtaaaggt attatttag cgggtggctc tggtactcgt    4680
ctttatcctg tgactatggc tgtcagtaaa cagctattac ctatttatga taagccgatg    4740
atctattacc cgctctctac actgatgttg gcgggtattc gcgatattct gattattagt    4800
acgccacagg atactcctcg ttttcaacaa ctcctgggtg atggtagcca gtggggtta    4860 aatcttcagt acaaagtgca accgagtcca gatggtcttg cgcaggcatt tatcatcggt    4920
gaagagttta tcggtggtga tgattgtgct ctggttctcg gtgataatat cttctacggt    4980
```

```
catgatctgc cgaagttaat ggatgtcgct gtcaacaaag aaagtggtgc aacggtattt   5040
gcctatcacg ttaatgatcc tgaacgctac ggtgttgttg agtttgataa aaacggtacg   5100
gcaatcagcc tggaagaaaa accgctacaa ccaaaaagta attatgcggt aaccgggctt   5160
tatttctatg ataacgacgt tgtcgaaatg gcgaaaaacc ttaagccttc tgcccgtggt   5220
gaactggaaa ttaccgatat taaccgtatt tatatggagc aggggcgttt atccgttgcc   5280
atgatgggac gtggttatgc atggctggac acggggacac atcaaagtct tattgaagca   5340
agcaacttca ttgcaacaat tgaagagcgc caagggttaa aggtatcttg cctggaagag   5400
attgcttatc gtaaaggctt tattgacgca gagcaggtta atgtattagc cgaaccgcta   5460
aagaaaaatg cttatggtca gtatctgttg aaaatgatta aaggttatta aaaatgaatg   5520
taattaaaac tgaaattcca gatgtattaa ttttcgagcc gaaagttttt ggtgatgaac   5580
gtggtttttt tatggaaagc tttaaccaga aagttttcga agaggctgta gggcggaagg   5640
ttgaatttgt tcaggataac cattctaaat caactaaggg tgtgttacgc ggactgcact   5700
atcagttgga accttatgct caaggtaaat tagttcgttg tgttgtcggt gaagttttttg   5760
atgtagcagt tgatattcgt aaatcgtcac ctacatttgg gaaatggatt ggggtgaatt   5820
tgtctgctga gaataagcgt cagttgtgga tacctgaagg atttgcgcat ggattttttgg   5880
tgctgagtga aacggctgag tttgtttata aacaacaaa ctattacaat ccaagttttg   5940
aaaaaagtat ttcatactca gatcctacca ttaaaattca gtgcccaat ttacaggata   6000
tgcattttaa attatcaaat aaggatttga atgctaagaa cttttttaat aacaatagtt   6060
taatgcaatg aagaaaaata tattgctctt gttcttagta catggggcaa attattttgtt   6120
cccgtttata gttcttccat atcaaactcg aatattaagc atcgagacat tcgcagatgt   6180
agcaaaaatt caagccgctg tgatgctttt atctttaatc gtaaattatg gatataactt   6240
atcaagtaca agagctatag ctagggccgt atctcaagca gaaataaata agatctatag   6300
tgagactctt attgtaaaat tattattggc aaccatttgt cttgcacttg gttgcgtaca   6360
tttgatgtat gtcaaagagt actcattgat atatcctttt ataatcagtt cgatatatct   6420
ttatggtagt gcattatttg ctacttggtt attccaagga cttgagaaaa tgaaagcggt   6480
cgttatagca acaacaatcg ctaaactgac tggtgtgata cttacttttta ttttagttaa   6540
gtctccaaat gatatagttg cagctcttttt tacacaaaac attgggatgt ttataagtgg   6600
tataatatct atttatttgg taaggaaaaa caaatatgca accgtaatat gttttcgact   6660
taaaatatt attgtaagct taaagaagc gtggccgttt tttttatcat tagctgcaac   6720
aagtgtatat acatatttta atgtgatttt attatctttt tatgctggcg actatgttgt   6780
ggcaaatttt aatgctgctg ataaattaag aatggctgct caagggttac ttattccaat   6840
aggacaggct gttttcccac gattatctaa actagagggc tatgaatata gttctaaact   6900
taaaatttat gcaataaggt atgctatttt tggtgttttgc attagtgcgg gacttgtatt   6960
tttaggtccc atgttaacta ctatttattt aggcaaagaa tattcgttgt caggagaata   7020
tcttcaaagt atgttttttac tacctgccac tatttcaata tcgactatac tgagtcaatg   7080
gatgttgata cctcaaggca agaaaaaaat attaagcaga atctatattc taggcgccat   7140
tgtccatttta ttatatgcat ttcctttagt ttactattat ggggcttggg gcatggtaat   7200
atcaattttta tttactgaag tcttaattgt attatttatg cttaaggctg tgaaatgact   7260
tactttactg gttttatttt aatattgttt gctattataa ttaaaagatt aactccaagt   7320
caaagcaaga aaaatattgt cttaatagct aatgcgtttt ggggaatatt gttggtaggt   7380
```

-continued

```
tatgctttca atgaacaata tttcgtacca ttaagtgcaa caaccttgtt ttttatactt      7440
gcattcttat ttttctttag tatgacttat attttaattg ctaggagtgg aagggttgtt      7500
ttttctttcg gtactggttt tatagaaagc aaatatattt actggtttgc tgggatgatt      7560
aatattatta gtatctgctt tggcattatc cttttatata ataatcattt ttctttaaaa      7620
gtaatgagag aaggaatttt agatggttct attagtgggt ttggattggg gataagtttg      7680
ccactttcct tctgctgtat gtatttagca agacatgaga ataaaaaaaa ttatttctat      7740
tgttttacac tactttcatt cttgcttgcg gtgttatcaa cttcaaagat cttcttaata      7800
ttattccttg tatatattgt tggaataaat agttatgtaa gcaaaaagaa attgcttatt      7860
tatggagtgt ttgtatttgg actgttcgct ttatcaagta ttatcttggg taagttctct      7920
tcagaccctg aaggcaagat tatttcagca atatttgata cgttaagggg ttatcttttc      7980
tcgggattgg cagcctttaa tctttatgtt gaaaagaatg ccacgctccc cgaaaattta      8040
cttttgtatc catttaagga ggtttggggg acgacaaaag atattcccaa aactgatatt      8100
ttgccttgga tcaacattgg tgtatgggac acgaatgtat atacagcttt tgcaccatgg      8160
tatcagtcat tggattata tgcagctata attattggta ttctcttagg gttttattac      8220
gggatatggt ttagctttcg tcaaaattta gctgtgggtt tttatcaaac attttttgtgt     8280 tttcctcttt taatgttgtt tttccaggag cattatttgt tgtcatggaa aatgcatttt      8340 atttatttt tatgtgcaat tttattagcg atgagaaaag cattagagta tgaataaata      8400
ttgtatctta gtactattta atccagatat aagtgttttt attgataatg tcaaaaagat      8460
tttatctttg gatgtaagtt tatttgtata tgacaattca gcaaataaac atgcattcct      8520
tgctctatcc tcacaagagc aaacaaagat aaattacttt tcgatatgtg aaaatatcgg      8580
attgtcgaaa gctataatg agacactaag gcatattctt gaatttaata agaatgtgaa      8640
aaataaaagc attaatgata gtgtgctttt tctcgaccaa gactctgaag ttgatttaaa      8700
ttccatcaat attttgtttg aaactatatc agcagcagag tctaatgtga tgatagtcgc      8760
ggggaatccc ataaggagag atggactacc gtatatagat taccccaca ctgtaaacaa       8820 tgtaaaattt gtaattagta gttatgctgt gtatcgctta gacgcattta gaaacatcgg      8880
cttgtttcaa gaagattttt ttatagatca tatcgatagt gatttttgtt caaggctgat      8940
aaaaagcaat taccaaattc tccttagaaa agatgccttt ttttatcaac caataggaat      9000
aaaaccattc aatctctgtg gtagatattt attccctatc ccatcacaac accgaacata      9060
ttttcaaatt agaaatgctt ttttaagtta caggcgcaat ggtgttacat ttaattttt       9120 atttagggaa attgtaaata gattgattat gagtatattc tcaggcctta acgagaaaga     9180
cttattgaaa cgattgcatt tatatttaaa aggaataaaa gatggtctta aaatgtaatt      9240
cttggctaga agtgggggcg ttgtgattaa aaaaaagtg gcggcgataa ttataacata      9300
taatccagat ctaacaattc tgcgagaaag ttatacgagt ctatataagc aagtcgataa      9360
aataattctt attgataaca actctacaaa ctatcaagaa cttaagaagt tattcgaaaa      9420 aaagaaaaa ataaaaatag tgcccttgag tgataatata ggactagcag cagctcaaaa      9480
tttaggtttg aacttagcta ttaaaaataa ctatacttat gctattttat tcgatcagga     9540
tagcgtctta caagacaatg gaattaacag tttctttttt gaatttgaga aattagttag      9600
tgaagaaaaa ttaaatatag ttgccattgg gccaagtttt tttgacgaaa agacaggaag      9660
acgctttcgg cctacaaaat ttatcggtcc cttttttatat ccctttcgta aaataaccac     9720
aaaaaatcct ctaacagaag ttgacttctt gattgcttct ggttgtttca taaaattgga     9780
```

-continued

```
gtgtattaaa tcagccggaa tgatgactga atcgttattc atcgattata ttgatgttga    9840
atggtcatat cgtatgcgtt cgtatggcta taagctatat attcataatg atattcacat    9900
gagtcattta gtgggagaat ctcgagttaa tttaggattg aaaactattt ctttacatgg    9960
gccgctaaga cgatattact tatttaggaa ttatatttca attttaaaag tgagatatat   10020
accgttagga tataaaatac gtgagggttt ttttaatatc ggaagatttt tggtaagtat   10080
gattataact aaaaatagaa aaactttaat tttatacact ataaaagcaa ttaaggacgg   10140
aataaataat gaaatgggga aatataaagg ctaa                                10174
```

<210> SEQ ID NO 6
<211> LENGTH: 643
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Lys Lys Ile Trp Leu Ala Leu Ala Gly Leu Val Leu Ala Phe Ser
1               5                   10                  15

Ala Ser Ala Ala Glu Glu Ala Phe Asp Leu Trp Asn Glu Cys Ala Lys
            20                  25                  30

Ala Cys Val Leu Asp Leu Lys Asp Gly Val Arg Ser Ser Arg Met Ser
        35                  40                  45

Val Asp Pro Ala Ile Ala Asp Thr Asn Gly Gln Gly Val Leu His Tyr
    50                  55                  60

Ser Met Val Leu Glu Gly Gly Asn Asp Ala Leu Lys Leu Ala Ile Asp
65                  70                  75                  80

Asn Ala Leu Ser Ile Thr Ser Asp Gly Leu Thr Ile Arg Leu Glu Gly
                85                  90                  95

Gly Val Glu Pro Asn Lys Pro Val Arg Tyr Ser Tyr Thr Arg Gln Ala
            100                 105                 110

Arg Gly Ser Trp Ser Leu Asn Trp Leu Val Pro Ile Gly His Glu Lys
        115                 120                 125

Pro Ser Asn Ile Lys Val Phe Ile His Glu Leu Asn Ala Gly Asn Gln
    130                 135                 140

Leu Ser His Met Ser Pro Ile Tyr Thr Ile Glu Met Gly Asp Glu Leu
145                 150                 155                 160

Leu Ala Lys Leu Ala Arg Asp Ala Thr Phe Phe Val Arg Ala His Glu
                165                 170                 175

Ser Asn Glu Met Gln Pro Thr Leu Ala Ile Ser His Ala Gly Val Ser
            180                 185                 190

Val Val Met Ala Gln Ala Gln Pro Arg Arg Glu Lys Arg Trp Ser Glu
        195                 200                 205

Trp Ala Ser Gly Lys Val Leu Cys Leu Leu Asp Pro Leu Asp Gly Val
    210                 215                 220

Tyr Asn Tyr Leu Ala Gln Gln Arg Cys Asn Leu Asp Asp Thr Trp Glu
225                 230                 235                 240

Gly Lys Ile Tyr Arg Val Leu Ala Gly Asn Pro Ala Lys His Asp Leu
                245                 250                 255

Asp Ile Lys Asp Asn Asn Asn Ser Thr Pro Thr Val Ile Ser His Arg
            260                 265                 270

Leu His Phe Pro Glu Gly Gly Ser Leu Ala Ala Leu Thr Ala His Gln
        275                 280                 285
```

```
Ala Cys His Leu Pro Leu Glu Ala Phe Thr Arg His Arg Gln Pro Arg
        290                 295                 300
Gly Trp Glu Gln Leu Glu Gln Cys Gly Tyr Pro Val Gln Arg Leu Val
305                 310                 315                 320
Ala Leu Tyr Leu Ala Ala Arg Leu Ser Trp Asn Gln Val Asp Gln Val
                325                 330                 335
Ile Arg Asn Ala Leu Ala Ser Pro Gly Ser Gly Gly Asp Leu Gly Glu
            340                 345                 350
Ala Ile Arg Glu Gln Pro Glu Gln Ala Arg Leu Ala Leu Thr Leu Ala
        355                 360                 365
Ala Ala Glu Ser Glu Arg Phe Val Arg Gln Gly Thr Gly Asn Asp Glu
370                 375                 380
Ala Gly Ala Ala Ser Ala Asp Val Val Ser Leu Thr Cys Pro Val Ala
385                 390                 395                 400
Lys Asp Gln Asn Arg Thr Lys Gly Glu Cys Ala Gly Pro Ala Asp Ser
                405                 410                 415
Gly Asp Ala Leu Leu Glu Arg Asn Tyr Pro Thr Gly Ala Glu Phe Leu
            420                 425                 430
Gly Asp Gly Gly Asp Val Ser Phe Ser Thr Arg Gly Thr Gln Asn Trp
        435                 440                 445
Thr Val Glu Arg Leu Leu Gln Ala His Arg Gln Leu Glu Glu Arg Gly
450                 455                 460
Tyr Val Phe Val Gly Tyr His Gly Thr Phe Leu Glu Ala Ala Gln Ser
465                 470                 475                 480
Ile Val Phe Gly Gly Val Arg Ala Arg Ser Gln Asp Leu Asp Ala Ile
                485                 490                 495
Trp Arg Gly Phe Tyr Ile Ala Gly Asp Pro Ala Leu Ala Tyr Gly Tyr
            500                 505                 510
Ala Gln Asp Gln Glu Pro Asp Ala Arg Gly Arg Ile Arg Asn Gly Ala
        515                 520                 525
Leu Leu Arg Val Tyr Val Pro Arg Trp Ser Leu Pro Gly Phe Tyr Arg
530                 535                 540
Thr Gly Leu Thr Leu Ala Ala Pro Glu Ala Ala Gly Glu Val Glu Arg
545                 550                 555                 560
Leu Ile Gly His Pro Leu Pro Leu Arg Leu Asp Ala Ile Thr Gly Pro
                565                 570                 575
Glu Glu Glu Gly Gly Arg Val Thr Ile Leu Gly Trp Pro Leu Ala Glu
            580                 585                 590
Arg Thr Val Val Ile Pro Ser Ala Ile Pro Thr Asp Pro Arg Asn Val
        595                 600                 605
Gly Gly Asp Leu Asp Pro Ser Ser Ile Pro Asp Lys Glu Gln Ala Ile
610                 615                 620
Ser Ala Leu Pro Asp Tyr Ala Ser Gln Pro Gly Lys Pro Pro Arg Glu
625                 630                 635                 640
Asp Leu Lys

<210> SEQ ID NO 7
<211> LENGTH: 624
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 7

```
Ala Glu Glu Ala Phe Asp Leu Trp Asn Glu Cys Ala Lys Ala Cys Val
1               5                   10                  15
Leu Asp Leu Lys Asp Gly Val Arg Ser Ser Arg Met Ser Val Asp Pro
            20                  25                  30
Ala Ile Ala Asp Thr Asn Gly Gln Gly Val Leu His Tyr Ser Met Val
        35                  40                  45
Leu Glu Gly Gly Asn Asp Ala Leu Lys Leu Ala Ile Asp Asn Ala Leu
    50                  55                  60
Ser Ile Thr Ser Asp Gly Leu Thr Ile Arg Leu Glu Gly Gly Val Glu
65                  70                  75                  80
Pro Asn Lys Pro Val Arg Tyr Ser Tyr Thr Arg Gln Ala Arg Gly Ser
                85                  90                  95
Trp Ser Leu Asn Trp Leu Val Pro Ile Gly His Glu Lys Pro Ser Asn
            100                 105                 110
Ile Lys Val Phe Ile His Glu Leu Asn Ala Gly Asn Gln Leu Ser His
        115                 120                 125
Met Ser Pro Ile Tyr Thr Ile Glu Met Gly Asp Glu Leu Leu Ala Lys
    130                 135                 140
Leu Ala Arg Asp Ala Thr Phe Phe Val Arg Ala His Glu Ser Asn Glu
145                 150                 155                 160
Met Gln Pro Thr Leu Ala Ile Ser His Ala Gly Val Ser Val Val Met
                165                 170                 175
Ala Gln Ala Gln Pro Arg Arg Glu Lys Arg Trp Ser Glu Trp Ala Ser
            180                 185                 190
Gly Lys Val Leu Cys Leu Leu Asp Pro Leu Asp Gly Val Tyr Asn Tyr
        195                 200                 205
Leu Ala Gln Gln Arg Cys Asn Leu Asp Asp Thr Trp Glu Gly Lys Ile
    210                 215                 220
Tyr Arg Val Leu Ala Gly Asn Pro Ala Lys His Asp Leu Asp Ile Lys
225                 230                 235                 240
Asp Asn Asn Asn Ser Thr Pro Thr Val Ile Ser His Arg Leu His Phe
                245                 250                 255
Pro Glu Gly Gly Ser Leu Ala Ala Leu Thr Ala His Gln Ala Cys His
            260                 265                 270
Leu Pro Leu Glu Ala Phe Thr Arg His Arg Gln Pro Arg Gly Trp Glu
        275                 280                 285
Gln Leu Glu Gln Cys Gly Tyr Pro Val Gln Arg Leu Val Ala Leu Tyr
    290                 295                 300
Leu Ala Ala Arg Leu Ser Trp Asn Gln Val Asp Gln Val Ile Arg Asn
305                 310                 315                 320
Ala Leu Ala Ser Pro Gly Ser Gly Gly Asp Leu Gly Glu Ala Ile Arg
                325                 330                 335
Glu Gln Pro Glu Gln Ala Arg Leu Ala Leu Thr Leu Ala Ala Ala Glu
            340                 345                 350
Ser Glu Arg Phe Val Arg Gln Gly Thr Gly Asn Asp Glu Ala Gly Ala
        355                 360                 365
Ala Ser Ala Asp Val Val Ser Leu Thr Cys Pro Val Ala Lys Asp Gln
    370                 375                 380
Asn Arg Thr Lys Gly Glu Cys Ala Gly Pro Ala Asp Ser Gly Asp Ala
385                 390                 395                 400
Leu Leu Glu Arg Asn Tyr Pro Thr Gly Ala Glu Phe Leu Gly Asp Gly
                405                 410                 415
```

```
Gly Asp Val Ser Phe Ser Thr Arg Gly Thr Gln Asn Trp Thr Val Glu
            420                 425                 430

Arg Leu Leu Gln Ala His Arg Gln Leu Glu Glu Arg Gly Tyr Val Phe
        435                 440                 445

Val Gly Tyr His Gly Thr Phe Leu Glu Ala Ala Gln Ser Ile Val Phe
    450                 455                 460

Gly Gly Val Arg Ala Arg Ser Gln Asp Leu Asp Ala Ile Trp Arg Gly
465                 470                 475                 480

Phe Tyr Ile Ala Gly Asp Pro Ala Leu Ala Tyr Gly Tyr Ala Gln Asp
                485                 490                 495

Gln Glu Pro Asp Ala Arg Gly Arg Ile Arg Asn Gly Ala Leu Leu Arg
            500                 505                 510

Val Tyr Val Pro Arg Trp Ser Leu Pro Gly Phe Tyr Arg Thr Gly Leu
        515                 520                 525

Thr Leu Ala Ala Pro Glu Ala Ala Gly Glu Val Glu Arg Leu Ile Gly
    530                 535                 540

His Pro Leu Pro Leu Arg Leu Asp Ala Ile Thr Gly Pro Glu Glu Glu
545                 550                 555                 560

Gly Gly Arg Val Thr Ile Leu Gly Trp Pro Leu Ala Glu Arg Thr Val
                565                 570                 575

Val Ile Pro Ser Ala Ile Pro Thr Asp Pro Arg Asn Val Gly Gly Asp
            580                 585                 590

Leu Asp Pro Ser Ser Ile Pro Asp Lys Glu Gln Ala Ile Ser Ala Leu
        595                 600                 605

Pro Asp Tyr Ala Ser Gln Pro Gly Lys Pro Pro Arg Glu Asp Leu Lys
    610                 615                 620

<210> SEQ ID NO 8
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Lys Lys Thr Ala Ile Ala Ile Ala Val Ala Leu Ala Gly Phe Ala
1               5                   10                  15

Thr Val Ala Gln Ala Asp Val Ile Ile Lys Pro Gln Val Ser Gly Val
            20                  25                  30

Ile Val Asn Lys Leu Phe Lys Ala Gly Asp Lys Val Lys Lys Gly Gln
        35                  40                  45

Thr Leu Phe Ile Ile Glu Gln Asp Gln Ala Ser Lys Asp Phe Asn Arg
    50                  55                  60

Ser Lys Ala Leu Phe Ser Gln Leu Asp His Thr Glu Ile Lys Ala Pro
65                  70                  75                  80

Phe Asp Gly Thr Ile Gly Asp Ala Leu Val Asn Ile Gly Asp Tyr Val
                85                  90                  95

Ser Ala Ser Thr Thr Glu Leu Val Arg Val Thr Asn Leu Asn Pro Ile
            100                 105                 110

Tyr Ala Asp Gly Ser His His His His His
        115                 120

<210> SEQ ID NO 9
<211> LENGTH: 126
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 9

Met Lys Lys Thr Ala Ile Ala Ile Ala Val Ala Leu Ala Gly Phe Ala
1               5                   10                  15

Thr Val Ala Gln Ala Asp Val Ile Ile Lys Pro Gln Val Ser Gly Val
            20                  25                  30

Ile Val Asn Lys Leu Phe Lys Ala Gly Asp Lys Val Lys Lys Gly Gln
        35                  40                  45

Thr Leu Phe Ile Ile Glu Gln Asp Gln Phe Asn Arg Ser Lys Ala Leu
50                  55                  60

Phe Ser Gln Ser Ala Ile Ser Gln Lys Glu Leu Asp His Thr Glu Ile
65                  70                  75                  80

Lys Ala Pro Phe Asp Gly Thr Ile Gly Asp Ala Leu Val Asn Ile Gly
                85                  90                  95

Asp Tyr Val Ser Ala Ser Thr Thr Glu Leu Val Arg Val Thr Asn Leu
            100                 105                 110

Asn Pro Ile Tyr Ala Asp Gly Ser His His His His His His
        115                 120                 125

<210> SEQ ID NO 10
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Lys Lys Thr Ala Ile Ala Ile Ala Val Ala Leu Ala Gly Phe Ala
1               5                   10                  15

Thr Val Ala Gln Ala Asp Val Ile Ile Lys Pro Gln Val Ser Gly Val
            20                  25                  30

Ile Val Asn Lys Leu Phe Lys Ala Gly Asp Lys Val Lys Lys Gly Gln
        35                  40                  45

Thr Leu Phe Ile Ile Glu Gln Asp Gln Phe Asn Arg Ser Lys Ala
    50                  55                  60

Leu Asp His Thr Glu Ile Lys Ala Pro Phe Asp Gly Thr Ile Gly Asp
65                  70                  75                  80

Ala Leu Val Asn Ile Gly Asp Tyr Val Ser Ala Ser Thr Thr Glu Leu
                85                  90                  95

Val Arg Val Thr Asn Leu Asn Pro Ile Tyr Ala Asp Gly Ser His His
            100                 105                 110

His His His His
        115

<210> SEQ ID NO 11
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 11

Met Lys Tyr Leu Leu Pro Thr Ala Ala Ala Gly Leu Leu Leu Leu Ala
1               5                   10                  15

Ala Gln Pro Ala Met Ala Met His Met Ser Lys Glu Glu Ala Pro Lys
            20                  25                  30

Ile Gln Met Pro Pro Gln Pro Val Thr Thr Met Ser Ala Lys Ser Glu
        35                  40                  45

Asp Leu Pro Leu Ser Phe Thr Tyr Pro Ala Lys Leu Val Ser Asp Tyr
    50                  55                  60

Asp Val Ile Ile Lys Pro Gln Val Ser Gly Val Ile Val Asn Lys Leu
65                  70                  75                  80

Phe Lys Ala Gly Asp Lys Val Lys Lys Gly Gln Thr Leu Phe Ile Ile
                85                  90                  95

Glu Gln Asp Lys Phe Lys Ala Ser Val Asp Ser Ala Tyr Gly Gln Ala
            100                 105                 110

Leu Met Ala Lys Ala Thr Phe Glu Asn Ala Ser Lys Asp Phe Asn Arg
        115                 120                 125

Ser Lys Ala Leu Phe Ser Lys Ser Ala Ile Ser Gln Lys Glu Tyr Asp
    130                 135                 140

Ser Ser Leu Ala Thr Phe Asn Asn Ser Lys Ala Ser Leu Ala Ser Ala
145                 150                 155                 160

Arg Ala Gln Leu Ala Asn Ala Arg Ile Asp Leu Asp His Thr Glu Ile
                165                 170                 175

Lys Ala Pro Phe Asp Gly Thr Ile Gly Asp Ala Leu Val Asn Ile Gly
            180                 185                 190

Asp Tyr Val Ser Ala Ser Thr Thr Glu Leu Val Arg Val Thr Asn Leu
        195                 200                 205

Asn Pro Ile Tyr Ala Asp Phe Phe Ile Ser Asp Thr Asp Lys Leu Asn
    210                 215                 220

Leu Val Arg Asn Thr Gln Ser Gly Lys Trp Asp Leu Asp Ser Ile His
225                 230                 235                 240

Ala Asn Leu Asn Leu Asn Gly Glu Thr Val Gln Gly Lys Leu Tyr Phe
                245                 250                 255

Ile Asp Ser Val Ile Asp Ala Asn Ser Gly Thr Val Lys Ala Lys Ala
            260                 265                 270

Val Phe Asp Asn Asn Ser Thr Leu Leu Pro Gly Ala Phe Ala Thr
        275                 280                 285

Ile Thr Ser Glu Gly Phe Ile Gln Lys Asn Gly Phe Lys Val Pro Gln
    290                 295                 300

Ile Gly Val Lys Gln Asp Gln Asn Asp Val Tyr Val Leu Leu Val Lys
305                 310                 315                 320

Asn Gly Lys Val Glu Lys Ser Ser Val His Ile Ser Tyr Gln Asn Asn
                325                 330                 335

Glu Tyr Ala Ile Ile Asp Lys Gly Leu Gln Asn Gly Asp Lys Ile Ile
            340                 345                 350

Leu Asp Asn Phe Lys Lys Ile Gln Val Gly Ser Glu Val Lys Glu Ile
        355                 360                 365

Gly Ala Gln Leu Glu His His His His His
    370                 375

<210> SEQ ID NO 12
<211> LENGTH: 132
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 12

Met Lys Lys Thr Ala Ile Ala Ile Ala Val Ala Leu Ala Gly Phe Ala
1               5                   10                  15

Thr Val Ala Gln Ala Thr Pro Gln Asn Ile Thr Asp Leu Cys Ala Glu
            20                  25                  30

Tyr His Asn Thr Gln Ile His Thr Leu Asn Asp Lys Ile Phe Ser Tyr
        35                  40                  45

Thr Glu Ser Leu Ala Gly Lys Arg Glu Met Ala Ile Ile Thr Phe Lys
    50                  55                  60

Asn Gly Ala Thr Phe Gln Val Glu Val Pro Gly Ser Gln His Ile Asp
65                  70                  75                  80

Ser Gln Lys Lys Ala Ile Glu Arg Met Lys Asp Thr Leu Arg Ile Ala
                85                  90                  95

Tyr Leu Thr Glu Ala Lys Val Glu Lys Leu Cys Val Trp Asn Asn Lys
            100                 105                 110

Thr Pro His Ala Ile Ala Ala Ile Ser Met Ala Asn Gly Ser His His
        115                 120                 125

His His His His
    130

<210> SEQ ID NO 13
<211> LENGTH: 288
<212> TYPE: PRT
<213> ORGANISM: Campylobacter jejuni

<400> SEQUENCE: 13

Met Lys Lys Ile Leu Leu Ser Val Leu Thr Thr Phe Val Ala Val Val
1               5                   10                  15

Leu Ala Ala Cys Gly Gly Asn Ser Asp Ser Lys Thr Leu Asn Ser Leu
            20                  25                  30

Asp Lys Ile Lys Gln Asn Gly Trp Arg Ile Gly Val Phe Gly Asp Lys
        35                  40                  45

Pro Pro Phe Gly Tyr Val Asp Glu Lys Gly Asn Asn Gln Gly Tyr Asp
    50                  55                  60

Ile Ala Leu Ala Lys Arg Ile Ala Lys Glu Leu Phe Gly Asp Glu Asn
65                  70                  75                  80

Lys Val Gln Phe Val Leu Val Glu Ala Ala Asn Arg Val Glu Phe Leu
                85                  90                  95

Lys Ser Asn Lys Val Asp Ile Ile Leu Ala Asn Phe Thr Gln Thr Pro
            100                 105                 110

Glu Arg Ala Glu Gln Val Asp Phe Cys Leu Pro Tyr Met Lys Val Ala
        115                 120                 125

Leu Gly Val Ala Val Pro Lys Asp Ser Asn Ile Thr Ser Val Glu Asp
    130                 135                 140

Leu Lys Asp Lys Thr Leu Leu Leu Asn Lys Gly Thr Thr Ala Asp Ala
145                 150                 155                 160

Tyr Phe Thr Gln Asp Tyr Pro Asn Ile Lys Thr Leu Lys Tyr Asp Gln
                165                 170                 175

Asn Thr Glu Thr Phe Ala Ala Leu Met Asp Lys Arg Gly Asp Ala Leu
            180                 185                 190

Ser His Asp Asn Thr Leu Leu Phe Ala Trp Val Lys Asp His Pro Asp
        195                 200                 205
```

```
Phe Lys Met Gly Ile Lys Glu Leu Gly Asn Lys Asp Val Ile Ala Pro
    210                 215                 220

Ala Val Lys Lys Gly Asp Lys Glu Leu Lys Glu Phe Ile Asp Asn Leu
225                 230                 235                 240

Ile Ile Lys Leu Gly Gln Glu Gln Phe Phe His Lys Ala Tyr Asp Glu
                245                 250                 255

Thr Leu Lys Ala His Phe Gly Asp Asp Val Lys Ala Asp Asp Trp Ile
                260                 265                 270

Glu Gly Gly Lys Ile Leu Glu Gln Lys Leu Ile Ser Glu Glu Asp Leu
            275                 280                 285

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aagctagcgc cgccgaggaa gccttcgacc                                      30

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aagaattctc agtggtggtg gtggtggtgc ttcaggtcct cgcgcggcgg                50

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gaaggcgggc gcgtgaccat tctcggc                                         27

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gccgagaatg gtcacgcgcc cgccttc                                         27

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cctgacctgc cccggggaat gcgcgg                                          26
```

```
<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ccgcgcattc cccggggcag gtcagg                                           26

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gtcgccaaag atcaaaatag aactaaa                                          27

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tttagttcta ttttgatctt tggcgac                                          27

<210> SEQ ID NO 22
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
catgacctgg acatcaagga taataataat tctactccca cggtcatcag tcatc           55

<210> SEQ ID NO 23
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gatgactgat gaccgtggga gtagaattat tattatcctt gatgtccagg tcatg           55

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 24

His His His His His His
1               5
```

```
<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Ser Asn Ile Thr
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

His Phe Gly Asp Asp
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Phe Asn Asn Ser
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Asn Asn Ser Thr
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Asn Asn Lys Thr
1               5
```